(12) United States Patent
Lou et al.

(10) Patent No.: US 8,853,180 B2
(45) Date of Patent: Oct. 7, 2014

(54) METHODS AND MATERIALS FOR MODULATING DEUBIQUITINASES AND UBIQUITINATED POLYPEPTIDES

(75) Inventors: Zhenkun Lou, Rochester, MN (US); Jian Yuan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 258 days.

(21) Appl. No.: 13/394,786

(22) PCT Filed: Sep. 9, 2010

(86) PCT No.: PCT/US2010/048302
§ 371 (c)(1),
(2), (4) Date: Mar. 7, 2012

(87) PCT Pub. No.: WO2011/031884
PCT Pub. Date: Mar. 17, 2011

(65) Prior Publication Data
US 2012/0171192 A1    Jul. 5, 2012

Related U.S. Application Data

(60) Provisional application No. 61/241,152, filed on Sep. 10, 2009, provisional application No. 61/260,637, filed on Nov. 12, 2009.

(51) Int. Cl.
| | | |
|---|---|---|
| *C12N 15/11* | (2006.01) | |
| *A61K 31/7105* | (2006.01) | |
| *G01N 33/50* | (2006.01) | |
| *C12Q 1/00* | (2006.01) | |
| *A61K 38/48* | (2006.01) | |

(52) U.S. Cl.
CPC .... *A61K 38/4873* (2013.01); *G01N 2333/4748* (2013.01); *G01N 2500/00* (2013.01); *A61K 31/7105* (2013.01); *G01N 33/5011* (2013.01); *C12Q 1/005* (2013.01)
USPC ...................................... 514/44 A

(58) Field of Classification Search
USPC ....................................... 514/44 A
See application file for complete search history.

(56) References Cited

U.S. PATENT DOCUMENTS

| | | | | |
|---|---|---|---|---|
| 7,001,980 | B1 * | 2/2006 | Parker et al. ............... | 530/388.8 |
| 2008/0038768 | A1 | 2/2008 | Filipuzzi et al. | |
| 2008/0167229 | A1 | 7/2008 | D'Andrea | |
| 2009/0017006 | A1 | 1/2009 | Freissmuth et al. | |
| 2009/0093430 | A1 | 4/2009 | Lockstone et al. | |
| 2011/0177054 | A1 * | 7/2011 | Gibbings et al. ............. | 424/94.4 |
| 2012/0258975 | A1 * | 10/2012 | Yuan et al. ............... | 514/264.11 |

FOREIGN PATENT DOCUMENTS

| | | |
|---|---|---|
| CN | 1445228 | 10/2003 |
| WO | WO99/64576 | * 12/1999 |
| WO | WO 2007/002972 | 1/2007 |
| WO | WO 2007/149484 | 12/2007 |
| WO | WO2009/099991 A2 * | 8/2009 |

OTHER PUBLICATIONS

Fellman et al. Mol. Cell 2011, 41:733-746.*
International Search Report and Written Opinion in International Application No. PCT/US2010/048302, mailed May 31, 2011, 11 pages.
International Preliminary Report on Patentability in International Application No. PCT/US2010/048302, mailed Mar. 22, 2012, 6 pages.
Chinese Office Action and Search Report for Application No. 201080051581.1 mailed Jun. 21, 2013, 13 pages.
European Office Action in European Application No. 10816095.3, dated Jan. 17, 2013, 7 pages.
European Search Report in European Application No. 10816095.3, dated Jan. 4, 2013, 6 pages.
Abraham, "Cell cycle checkpoint signaling through the ATM and ATR kinases," *Genes Dev.*, 2001, 15:2177-2196.
Anonymous: "Principles of cancer therapy," *The Merck Manual of Diagnosis and Therapy*, 18th Edition, 2006, 1157-1171.
Appella and Anderson, "Post-translational modifications and activation of p53 by genotoxic stresses," *Eur J Biochem*, 2001, 268:2764-2772.
Berglind et al., "Analysis of p53 mutation status in human cancer cell lines: a paradigm for cell line cross-contamination," *Cancer Biol. Ther.*, 2008, 7(5):699-708.
Beroud and Soussi, "The UMD-p53 database: New mutations and analysis tools," *Human Mutation*, 2003, 21:176-181
Bomberger et al., "The deubiquitinating enzyme USP10 regulates the post-endocytic sorting of CFTR in airway epithelial cells," *J Biol Chem.*, 2009, 284:18778-18789.

(Continued)

*Primary Examiner* — Brian Whiteman
(74) *Attorney, Agent, or Firm* — Fish & Richardson P.C.

(57) ABSTRACT

This document relates to methods and materials involved in modulating deubiquitinases (e.g., USP10 polypeptides) and/or ubiquitinated polypeptides (e.g., tumor suppressor polypeptides or mutant versions of tumor suppressor polypeptides). For example, methods and materials for increasing deubiquitinase (e.g., a USP10 polypeptide) expression or activity, methods and materials for decreasing deubiquitinase (e.g., a USP10 polypeptide) expression or activity, methods and materials for stabilizing tumor suppressor polypeptides (e.g., wild-type p53 polypeptides), methods and materials for de-stabilizing mutant versions of tumor suppressor polypeptides (e.g., mutant p53 polypeptides), and methods and materials for reducing cancer cell proliferation, increasing cancer cell apoptosis, and/or treating cancer (e.g., cancers having reduced levels of wild-type p53 polypeptides or cancers having increased levels of mutant p53 polypeptides) are provided. This document also provides methods and materials for identifying agonists or antagonists of USP10 polypeptide mediated stabilization of p53 polypeptides.

7 Claims, 43 Drawing Sheets

(56) References Cited

OTHER PUBLICATIONS

Boulkroun et al., "Vasopressin induced ubiquitin specific protease 10 increases ENaC cell surface expression by deubiquitylating and stabilizing sorting nexin 3," *Am J Physiol Renal Physiol.*, 2008, 295:F889-F900.

Boyd et al., "An intact HDM2 RING-finger domain is required for nuclear exclusion of p53," *Nat Cell Biol.*, 2000, 2:563-568.

Brooks and Gu, "Ubiquitination, phosphorylation and acetylation: the molecular basis for p53 regulation," *Curr Opin Cell Biol.*, 2003, 15:164-171.

Brooks et al., "The p53—Mdm2—HAUSP complex is involved in p53 stabilization by HAUSP," *Oncogene*, 2007, 26:7262-7266.

Canman et al., "Activation of the ATM kinase by ionizing radiation and phosphorylation of p53," *Science*, 1998, 281:1677-1679.

Chehab et al., "Chk2/hCds1 functions as a DNA damage checkpoint in G(1) by stabilizing p53," *Genes Dev.*, 2000, 14:278-288.

Chen et al., "ARF-BP1/Mule is a critical mediator of the ARF tumor suppressor," *Cell*, 2005, 121:1071-1083.

Colland et al., "Small-molecule inhibitor of USP7/HAUSP ubiquitin protease stabilizes and activates p53 in cells," *Molecular Cancer Therapeutics*, Aug. 2009, 8(8):2286-2295.

Cummins and Vogelstein, "HAUSP is required for p53 destabilization," *Cell Cycle*, 2004, 3:689-692.

Cummins et al., "Tumour suppression: disruption of HAUSP gene stabilizes p53," *Nature*, 2002, 416:648-653.

Dang et al., "Kinetic and Mechanistic Studies on the Hydrolysis of Ubiquitin C-Terminal 7-Amido-4-Methylcoumarin by Deubiquitinating Enzymes," *Biochemistry*, 1998, 37:1868-1879.

Deng et al., "Over-expression of genes and proteins of ubiquitin specific peptidases (USPs) and proteasome subunits (PSs) in breast cancer tissue observed by the methods of RFDD-PCR and proteomics," *Breast Cancer Res. Treatment*, 2007, 104(1):21-30.

Dornan et al., "The ubiquitin ligase COP1 is a critical negative regulator of p53," *Nature*, 2004, 429:86-92.

Duca, "Cancer biology: The missing link," *Cell*, 2011, 147:223-234 (Abstract Only).

el-Deiry et al., "Topological control of p21WAF1/CIP1 expression in normal and neoplastic tissues," *Cancer Res.*, 1995, 55:2910-2919.

Everett et al., "A novel ubiquitin-specific protease is dynamically associated with the PML nuclear domain and binds to a herpes virus regulatory protein," *Embo J*, 1997, 16:1519-1530.

Freedman and Levine, "Nuclear export is required for degradation of endogenous p53 by MDM2 and human papillomavirus E6," *Mol Cell Biol.*, 1998, 18:7288-7293.

GenBank NM_198395.1 (GI No. 38327551), 2009, 4 pages.

GenBank® Accession Nos. NM_005754.2 (Gi No. 38327550), 2009, 4 pages.

GenBank® Accession Nos. NM_013716.2, 2009, 4 pages.

GenBank® Accession Nos. NM_133565.1, 2009, 3 pages.

Geyer et al., "The MDM2 RING-finger domain is required to promote p53 nuclear export," *Nat Cell Biol.*, 2000, 2:569-573.

Gjoerup et al., "Induction of p53-independent apoptosis by simian virus 40 small t antigen," *J Virol.*, 2001, 75:9142-9155.

Godar et al. "Growth-inhibitory and tumorsuppressive functions of p53 depend on its repression of CD44 expression," *Cell*, 2008, 134:62-73.

Grossman et al., "Polyubiquitination of p53 by a ubiquitin ligase activity of p300," *Science*, 2003, 300:342-344.

Grunda et al., "Increased Expression of Thymidylate Synthetase (TS), Ubiquitin Specific Protease 10 (USP10) and Survivin is Associated with Poor Survival in Glioblastoma Multiforme (GBM)," *J Neurooncol.*, 2006, 80(3):261-274.

Haupt et al., "Mdm2 promotes the rapid degradation of p53," *Nature*, 1997, 387:296-299.

Hickson et al., "Identification and characterization of a novel and specific inhibitor of the ataxia-telangiectasia mutated kinase ATM," *Cancer Res.*, 2004, 64:9152-9159.

Hirao et al., "DNA damage-induced activation of p53 by the checkpoint kinase Chk2," *Science*, 2000, 287:1824-1827.

Honda et al., "Oncoprotein MDM2 is a ubiquitin ligase E3 for tumor suppressor p53," *FEBS Lett.*, 1997, 420:25-27.

Hu et al., "Structural basis of competitive recognition of p53 and MDM2 by HAUSP/USP7: implications for the regulation of the p53 and MDM2 pathway," *PLoS Biol.*, 2006, 4(2):e27, pp. 0228-0239.

Huibregtse et al., "A cellular protein mediates association of p53 with the E6 oncoprotein of human papillomavirus types 16 or 18," *Embo J.*, 1991, 10:4129-4135.

Irvine et al., "Rasputin, more promiscuous than ever: a review of G3BP," *Int J Dev Biol.*, 2004, 48:1065-1077.

Jimenez et al., "p53 regulation by post-translational modification and nuclear retention in response to diverse stresses," *Oncogene*, 1999, 18:7656-7665.

Jochemesen and Shiloh, "USP10: Friend and Foe," *Cell*, 2010, 140:308-310.

Kim et al., "Modulation of p53 and MDM2 activity by novel interaction with Ras-GAP binding proteins (G3BP)," *Oncogene*, 2007, 26:4209-4215.

Kruse and Gu, "MSL2 promotes MDM2 independent cytoplasmic localization of p53," *J Biol Chem.*, 2009, 284:3250-3263.

Kubbutat and Vousden, "Proteolytic cleavage of human p53 by calpain: a potential regulator of protein stability," *Mol Cell Biol.*, 1997, 17:460-468.

Lane, "Cancer. p53, guardian of the genome," *Nature*, 1992, 358:15-16.

Leng et al., "Pirh2, a p53-induced ubiquitin-protein ligase, promotes p53 degradation," *Cell*, 2003, 112:779-791.

Li et al., "A dynamic role of HAUSP in the p53-Mdm2 pathway," *Mol Cell.*, 2004, 13:879-886.

Li et al., "Deubiquitination of p53 by HAUSP is an important pathway for p53 stabilization," *Nature*, 2002, 416:648-653.

Li et al., "Monoversus polyubiquitination: differential control of p53 fate by Mdm2," *Science*, 2003, 302:1972-1975.

Liu et al., "Beclin1 Controls the Levels of p53 by Regulating the Deubiquitination Activity of USP10 and USP13," *Cell*, 2011, 147:223-234.

Meulmeester et al., "Loss of HAUSP-mediated deubiquitination contributes to DNA damage-induced destabilization of Hdmx and Hdm2," *Mol Cell*, 2005, 18:565-576.

Moffat et al., "A Lentiviral RNAi Library for Human and Mouse Genes Applied to an Arrayed Viral High-Content Screen," *Cell*, 2006, 124:1283-1298.

Moll et al., "Transcription-independent pro-apoptotic functions of p53," *Curr Opin Cell Biol.*, 2005, 17:631-636.

Nikolaev et al., "Parc: a cytoplasmic anchor for p53," *Cell*, 2003, 112:29-40.

Reece and Figg, "A novel regulator (USP10) of p53: Implications of tumor suppression and therapeutic targeting," *Cancer Biol. Therapy*, 2010, 9(8):583-584.

Riley et al., "Transcriptional control of human p53-regulated genes," *Nat Rev Mol Cell Biol.*, 2008, 9:402-412.

Sarkaria et al., "Inhibition of ATM and ATR kinase activities by the radiosensitizing agent, caffeine," *Cancer Res.*, 1999, 59:4375-4382.

Sheng et al., "Molecular recognition of p53 and MDM2 by USP7/HAUSP," *Nat Struct Mol Biol.*, 2006, 13:285-291.

Shieh et al., "The human homologs of checkpoint kinases Chk1 and Cds1 (Chk2) phosphorylate p53 at multiple DNA damage-inducible sites," *Genes Dev.*, 2000, 14:289-300.

Shim et al., "c-Myc transactivation of LDH-A: implications for tumor metabolism and growth," *Proc Natl Acad Sci USA*, 1997, 94:6658-6663.

Siliciano et al., "DNA damage induces phosphorylation of the amino terminus of p53," *Genes Dev.*, 1997, 11:3471-3481.

Soncini et al., "Ras—GAP SH3 domain binding protein (G2BP) is a modulator of USP10, a novel human ubiquitin specific protease," *Oncogene*, 2001, 20:3869-3879.

Song et al., "The deubiquitinylation and localization of PTEN are regulated by a HAUSP-PML network," *Nature*, 2008, 455:813-817.

Soussi et al., "p53 website and analysis of p53 gene mutations in human cancer: forging a link between epidemiology and carcinogenesis," *Hum Mutat*, 2000, 15:105-113.

Stewart et al., "Lentivirus-delivered stable gene silencing by RNAi in primary cells," *RNA*, 2003, 9:493-501.

(56) References Cited

OTHER PUBLICATIONS

Stommel et al., "A leucine-rich nuclear export signal in the p53 tetramerization domain: regulation of subcellular localization and p53 activity by NES masking," *Embo J.*, 1999, 18:1660-1672.

Terzian et al., "The inherent instability of mutant p53 is alleviated by Mdm2 or p16INK4a loss," *Genes Dev.*, 2008, 22:1337-1344.

Vikis and Guan, "Glutathione-STransferase-Fusion Based Assays for Studying Protein-Protein Interactions. In Protein-Protein Interactions," *Methods and Applications, Methods in Molecular Biology*, 261, Fu, H. Ed. Humana Press, Totowa, N.J., pp. 175-186 (2004).

Vogelstein et al., "Surfing the p53 network," *Nature*, 2000, 408:307-310.

Vousden, "Activation of the p53 tumor suppressor protein," *Biochim Biophys Acta*, 2002 1602:47-59.

Yamamoto and Tsunetsugu-Yokota, "Prospects for the Therapeutic Application of Lentivirus-Based Gene Theraphy to HIV-1 Infection," *Curro Gene Ther.*, 2008, 8(1):1-8.

Yuan et al., "USP10 Regulates p53 Localization and Stability by Deubiquitinating p53," *Cell*, 2010, 140(3):384-396.

Zhang and Xiong, "A p53 amino-terminal nuclear export signal inhibited by DNA damage-induced phosphorylation," *Science*, 2001, 292:1910-1915.

Zufferey et al., "Multiply attenuated lentiviral vector achieves efficient gene delivery in vivo," *Nat Biotechnol.*, 1997, 15:871-85.

Zufferey et al., "Self-Inactivating Lentivirus Vector for Safe and Efficient in Vivo Gene Delivery," *J. Virol.*, 1998, 72:9873-80.

Chinese office action and search report in Chinese App. No. 201050051581.1 mailed Jun. 21, 2013, 16 pages.

Nomura et al., "Antiteratogenic effects of tumor inhibitors, caffeine, antipain, and retinoic acid in mice," *Cancer Res.*, 43(11):5156-5162, Nov. 1983.

European Office Action in European Application No. 10816095.3 dated Jul. 17, 2014, 11 pages.

* cited by examiner

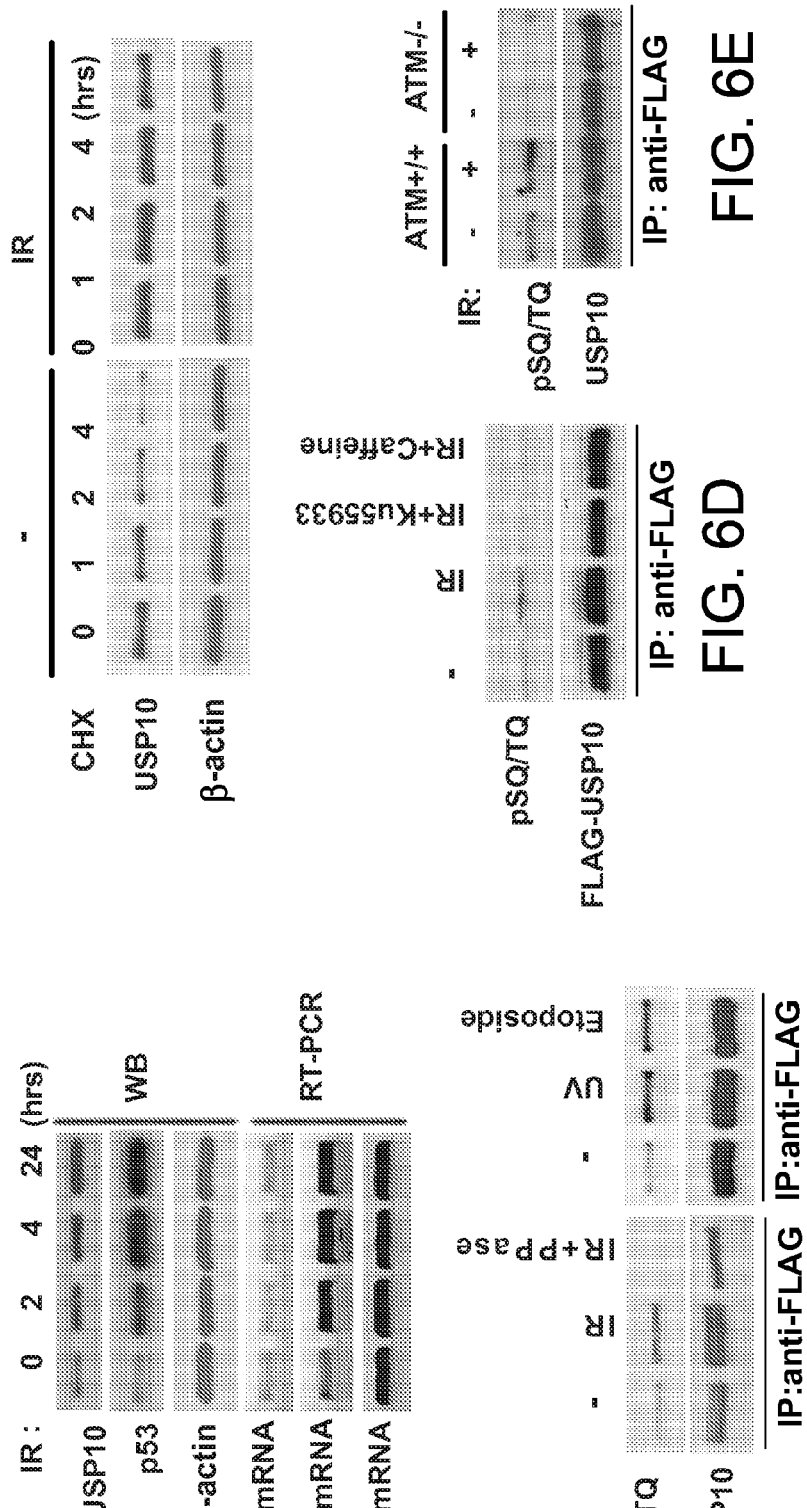

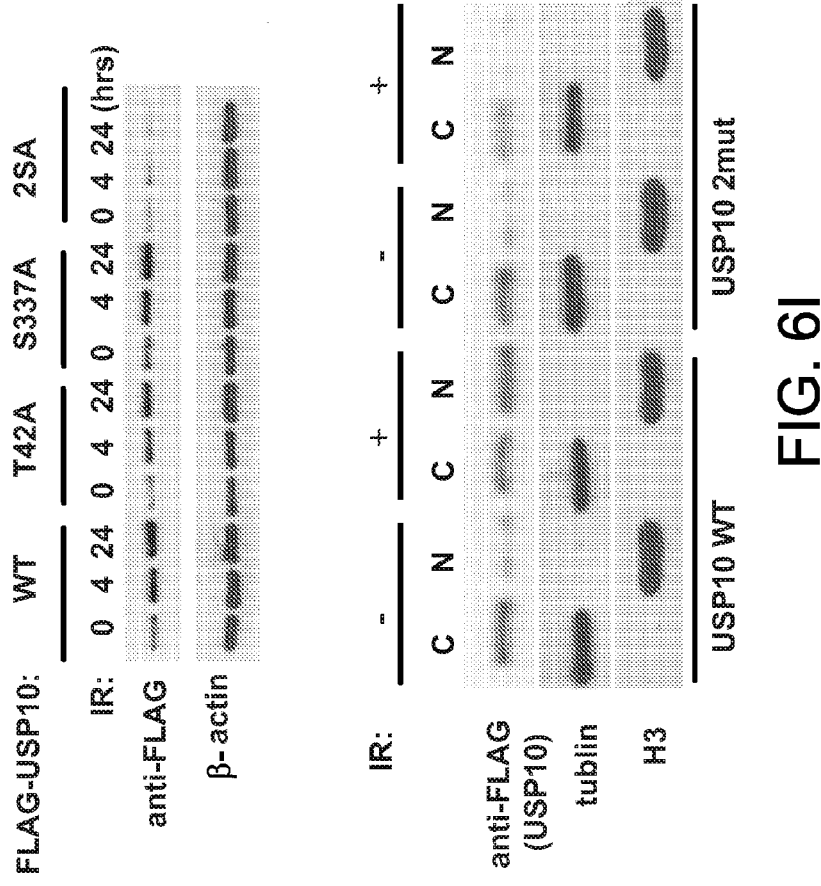
FIG. 6G
FIG. 6I
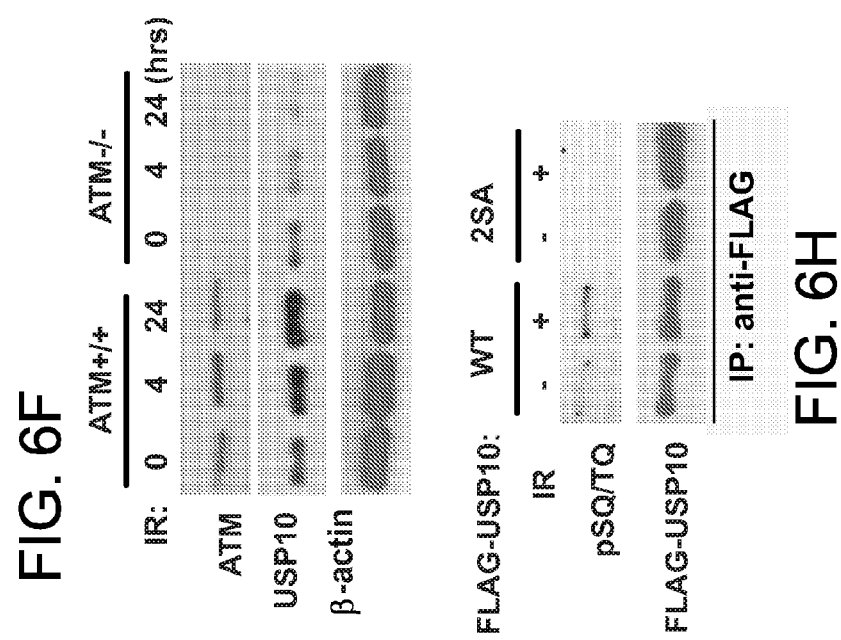
FIG. 6F
FIG. 6H

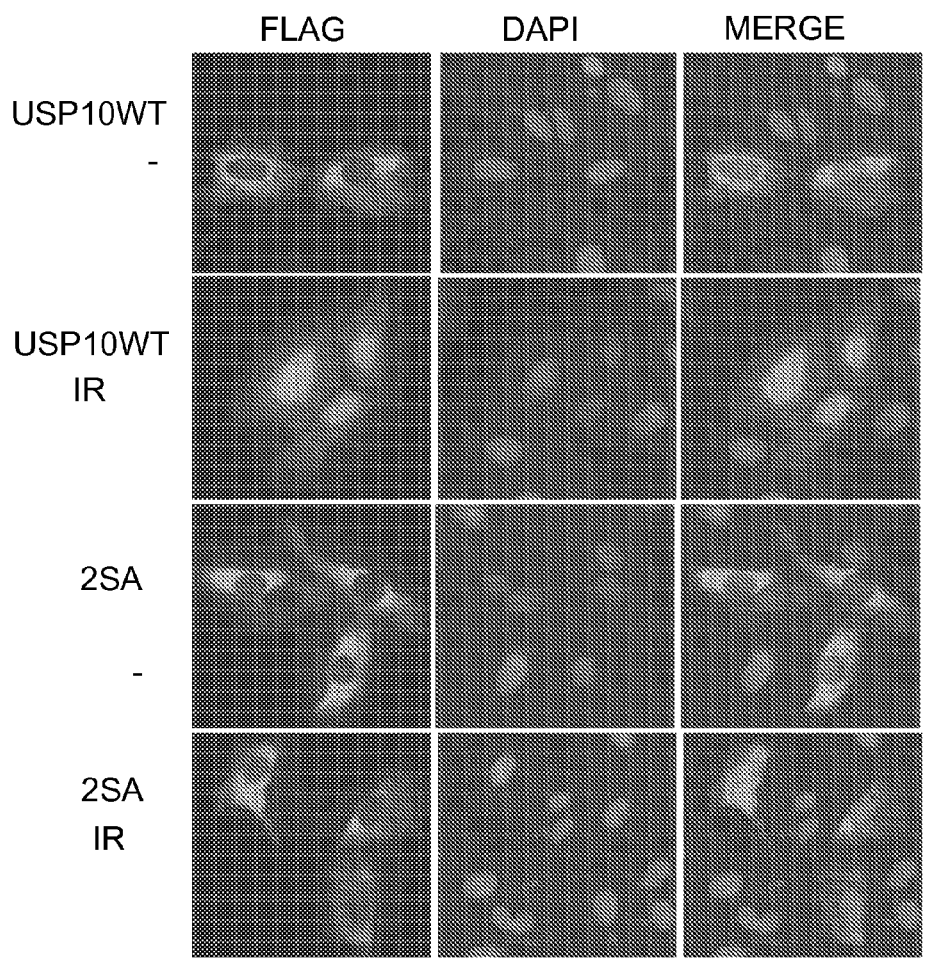
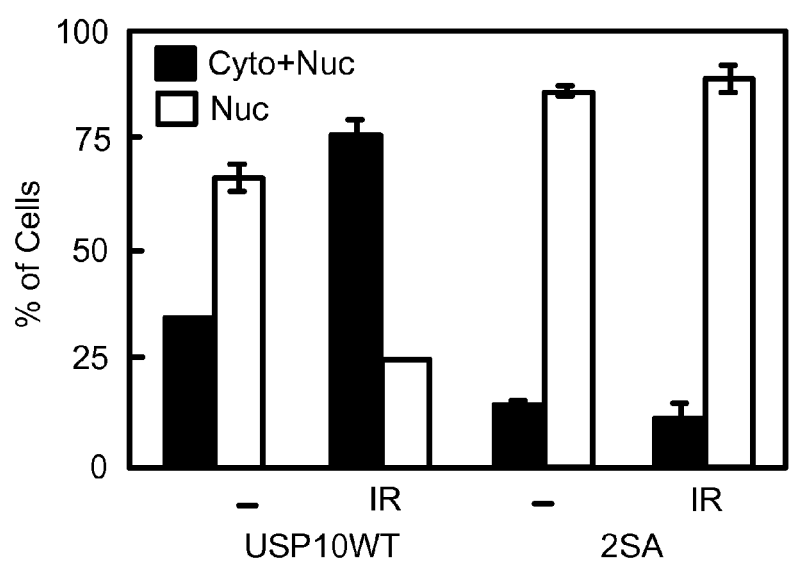
FIG. 8B

| | | | | | |
|---|---|---|---|---|---|
|    1 | ctccccgcgc | cccgcggcgc | gcggccagtg | cgcaggcgcg | gcggccgatg | cgagtgtgta |
|   61 | tgtgcgggcg | agaagatggc | ggcggcgggg | gaagcagcgt | gagcagccgg | aggatccgcg |
|  121 | agtcccaatg | aaacgggcag | ccatggccct | ccacagcccg | cagtatattt | ttggagattt |
|  181 | tagccctgat | gaattcaatc | aattctttgt | gactcctcga | tcttcagttg | agcttcctcc |
|  241 | atacagtgga | acagttctgt | gtggcacaca | ggctgtggat | aaactacctg | atggacaaga |
|  301 | atatcagaga | attgagtttg | gtgtcgatga | agtcattgaa | cccagtgaca | ctttgccgag |
|  361 | aaccccagct | tacagtattt | caagcacact | gaaccctcag | gccctgaat | ttattctcgg |
|  421 | ttgtacagct | tccaaaataa | cccctgatgg | tatcactaaa | gaagcaagct | atggctccat |
|  481 | cgactgccag | tacccaggct | ctgcctcgc | tttggatgga | agttctaatg | tggaggcgga |
|  541 | agtttttgaa | aatgatgtgt | tctcaggtgg | tcttggacaa | agggagcgta | aaaagaagaa |
|  601 | aaagcggcca | cctggatatt | acagctattt | gaaagatggt | ggcgatgata | gtatctccac |
|  661 | agaagccctg | gtcaatggcc | atgccccgtc | agttacgcgc | aacagttgta | gtgcagagga |
|  721 | tgcagaattt | atgggtgaca | gtgacactgt | gcctgacagt | gcctgacagt | ctttcccg | gagcactcgg |
|  781 | gaactccaca | gactctgtca | gtcctgtca | gtgacattgt | ccttcccg | ggggctgatt | ttggtcagtc |
|  841 | cagtgacacc | aggactgcag | ggcagccaga | tgcccccgtc | agttacgcgc | gagcactcgg |
|  901 | ctgcttccct | gcagaggctg | gcagagacac | cctgtcaagg | acagctgggg | ctcagcctg |
|  961 | cgttggtacc | gatactacta | aaaacggttg | agttgctaat | gacacacc | tgaatctc |
| 1021 | gggtgagggc | acagctacca | acggggtgga | gttgcacac | acgggctctg | tagacttgga |
| 1081 | cccaaccaaa | cccgagagtg | catcacctcc | tgctgacggc | catgattcta | catcaggcac |
| 1141 | ccttcctcgc | agccagccca | agtcctgggc | cagcctcttt | ccgccatat | ctccccggt |
| 1201 | ctctgaaaag | gtgttgctat | tggaaactaa | gcttgttccg | gtttcagagg | atcctgtagc |
| 1261 | ttctgaaaag | caggttgaag | tcaaagaagg | aacctaatc | cataaaccag | tgtcgttgca |
| 1321 | cataaagatt | gcagagttgc | tggagaatgt | gtgctacatt | aatgctacac | tgtcaggcatt |
| 1381 | acccgtggg | ctgatcaata | ccaccgatat | gaagttcatt | cctctgtatt | ccaagtgca |
| 1441 | ggttgcttgc | ccgtcaacac | accccgatga | cagctttgtt | cggctaatga | atgagttcac |
| 1501 | aaggcctgt | acgtcaacaa | ccaccccgata | cagctttgtt | cggctaatga | atgagttcac |
| 1561 | taatatgcca | gtacctccaa | aacccgaca | agctcttgga | gataaaatcg | tgaggatat |
| 1621 | tcgccctgga | gctgccttg | agcccacata | tatttacaga | ctcctgacag | ttaacaagtc |
| 1681 | aagcctgtct | gaaaagggtc | gacaagaaga | tgctgaggaa | tacttaggct | tcattctaaa |
| 1741 | tggacttcat | gaggaaatgt | tgaacctaaa | gaagctcctc | tcaccaagta | atgaaaaact |

FIG. 9

```
1801  tacgatttcc  aacggcccca  aaaaccactc  ggtcaatgaa  gaagagcagg  aagaacaagg
1861  tgaaggaagc  gaggatgaat  gggaacaagt  gggcccccgg  aacaagactt  cgtcacccg
1921  ccaggcggat  tttgttcaga  ctccaatcac  cggcatttt   ggtggacaca  tcaggtctgt
1981  ggtttaccag  cagagttcaa  aagaatctgc  cactttgca   ccattttca   cgttgcagtt
2041  ggatatccag  tcagacaaga  tacgcacagt  ccaggatgca  ctggagagct  tggtggcaag
2101  agaatctgtc  caaggttata  ccacaaaaac  caaacaagag  gttgagataa  gtcgaagagt
2161  gactctgaa   aaactccctc  ctgtcctcgt  gctgcacctg  aaacgattcg  tttatgagaa
2221  gactggtggg  tgccagaagc  tattgaatat  cctgtggact  tgaaattag   tgaaattag
2281  taagaactg   ctttctccag  ttatcaaaaa  taagaatttt  aaatgccacc  gaacctatcg
2341  gctctttgca  gtggtctacc  gggttaaaaa  cagtgcgacg  gcgggccatt  acactacaga
2401  cgtcttccag  atcggtctga  atcacggcaa  gcgcatcgat  gaccagacag  tcaaggtgat
2461  caaccagtac  caggtggtga  atgcctgcga  tgaacgcaca  gcctacctcc  tgtattaccg
2521  ccgagtggac  ctgctgtaaa  cccccgcctc  gctgtgtgtg  cgcccagtgc  ccgcttcgta
2581  ggacaccacc  tcacactcac  ttctttagtgg ctcttagag   agaaactctt
2641  tctcccttg   caaaatggg   ctagaatgaa  aaggagatgc  cttgggttc   gtcacaaca
2701  cagcttctgt  tgactctaac  ttccaaatca  aaatcatttg  gttgaaacag  actgttgctt
2761  gattagaa    aatacacaaa  acccatatt   tctgaaataa  tgctgattcc  tgagataaga
2821  aagtggattt  gatcccagt   ctcattgctt  agtagaataa  atcctgcacc  agcaacaaca
2881  cttgtaaatt  tgtgaaaatg  aatttattct  ttccttaaaa  aagaaatttt  ttaatccatc
2941  acacttttct  tccctaccct  ttagtttttg  ataaatgata  aaaatgagcc  agttatcaaa
3001  gaagaactag  ttcttacttc  aaaagaaaaa  taaacataaa  aaataagttg  ctggttccta
3061  acaggaaaaa  ttttaataat  tgtactgaga  gaaactgctt  acgtacacat  tgcagatcaa
3121  atatttggag  ttaaaatgtt  agtctacata  gatgggtgat  tgtaacttta  ttgccattaa
3181  aagatttcaa  attgcattca  tgcttctgtg  tacacataat  gaaaaatggg  caaataatga
3241  agatctctcc  ttcagtctgc  tctgttaat   tctgctgtct  gctcttctct  aatgctgcgt
3301  ccctaattgt  acacagttta  gtgatatcta  ggagtataaa  gttgtcgccc  atcaataaaa
3361  atcacaaagt  tggtttaaaa  aaaaaaaaaa
```

FIG. 9 (CONTINUED)

MALHSPQYIFGDFSPDEFNQFFVTPRSSVELPPYSGTVLCGTQAVDKLPDGQEYQ
RIEFGVDEVIEPSDTLPRTPSYSISSTLNPQAPEFILGCTASKITPDGITKEASYGSID
CQYPGSALALDGSSNVEAEVLENDGVSGGLGQRERKKKKKRPPGYYSYLKDGG
DDSISTEALVNGHANSAVPNSVSAEDAEFMGDMPPSVTPRTCNSPQNSTDSVSDI
VPDSPFPGALGSDTRTAGQPEGGPGADFGQSCFPAEAGRDTLSRTAGAQPCVGT
DTTENLGVANGQILESSGEGTATNGVELHTTESIDLDPTKPESASPPADGTGSAG
TLPVSQPKSWASLFHDSKPSSSSPVAYVETKYSPPAISPLVSEKQVEVKEGLVPVS
EDPVAIKIAELLENVTLIHKPVSLQPRGLINKGNWCYINATLQALVACPPMYHLM
KFIPLYSKVQRPCTSTPMIDSFVRLMNEFTNMPVPPKPRQALGDKIVRDIRPGAAF
EPTYIYRLLTVNKSSLSEKGRQEDAEEYLGFILNGLHEEMLNLKKLLSPSNEKLTI
SNGPKNHSVNEEEQEEQGEGSEDEWEQVGPRNKTSVTRQADFVQTPITGIFGGHI
RSVVYQQSSKESATLQPFFTLQLDIQSDKIRTVQDALESLVARESVQGYTTKTKQ
EVEISRRVTLEKLPPVLVLHLKRFVYEKTGGCQKLIKNIEYPVDLEISKELLSPGV
KNKNFKCHRTYRLFAVVYHHGNSATGGHYTTDVFQIGLNGWLRIDDQTVKVIN
QYQVVKPTAERTAYLLYYRRVDLL

FIG. 10 shRNA-1: GCCTCTCTTTAGTGGCTCTTT (SEQ ID NO:7)
shRNA-2: CCTATGTGGAAACTAAGTATT (SEQ ID NO:8)
shRNA-3: CCCATGATAGACAGCTTTGTT (SEQ ID NO:9)
shRNA-4: GCTGTGGATAAACTACCTGAT (SEQ ID NO:10)
shRNA-5: CGACAAGCTCTTGGAGATAAA (SEQ ID NO:11)

FIG. 11

```
   1 gattgggtt ttcccctccc atgtgctcaa gactggcgct aaaagttttg agcttctcaa
  61 aagtctagag ccaccgtcca gggagcaggt agctgctggg ctccgggac actttgcgtt
 121 cgggctggga gcgtgctttc cacgacggtg cacgcttcc acacgcttcc agccagactg
 181 ccttccgggt cactgccatg gaggagccgc agtcagatcc tagcgtcgag cccctctga
 241 gtcaggaaac atttcagac ctatggaaac aaacaacgtt ctgtccccct
 301 tgccgtccca agcaatggat gatttgatgc tgtcccgga cgatattgaa caatggttca
 361 ctgaagaccc aggtccagat gaagctccca gaatgccaga ggctgctccc cccgtgcc
 421 ctgcaccagc agctcctaca ccggcggcc ctgcaccagc cccctcctgg ccctgtcat
 481 cttctgtccc ttcccagaaa acctaccagg gcagctacgg tttccgtctg ggcttcttgc
 541 attctggga gccaagtct gtgacttgca cgtactcccc tgccctcaac aagatgtttt
 601 gccaactggc caagacctgc cctgtgcagc tgtgggttga ttccacaccc ccgcccggca
 661 cccgcgtccg cgccatgccc atctacaagc agtcacagca catgacggag gttgtgaggc
 721 gctgccccca ccatgagcgc tgctcagata gcgatggtct gcccctcct cagcatctta
 781 tccgagtgga aggaaatttg cgtgtggagt atttggatga cagaaacact tttcgacata
 841 gtgtgtgtgt gccctatgag ccgcctgagg ttggctctga cctgtaccac ctccactaca
 901 actacatgtg taacagttcc tgcatgggcg gcatgaaccg gaggcccatc ctcaccatca
 961 tcacactgga agactccagt ggtaatctac tgggacggaa cagctttgag gtgcgtgttt
1021 gtgcctgtcc tgggagagac cggcgcacag aggaagagaa tctccgcaag aaaggggagc
1081 ctcaccacga gctgccccca gggagcacta agcgagcact gccaacaac accccttcag
1141 ctcccccgca aagaagaaa ccactggatg gagaatattt cacccttcag atccgtgggc
1201 gtgagcgctt cgagatgttc cgagagctga atgaggcctt ggaactcaag gatgcccagg
1261 ctgggaagga gccagggggg agcaggggtc cctgaagtcc cctgaagtcc aaaagggtc
1321 agtctacctc ccgccataaa aactcatgt tcaagacaga agggcctgac tcccctgcca
1381 attctccact tctgttccc cactgacagc ctcccaccc catctctccc tccccaccag
1441 ttttgggttt aaccctttg tgcaataggt tgcattcaga agcaccagg
```

FIG. 12

```
1501  acttccattt gctttgtccc ggggctccac tgaacaagtt ggcctgcact ggtgttttgt
1561  tgtgggagg aggatgggga gtaggacata ccagcttaga ttttaaggtt tttactgtga
1621  gggatgtttg ggagatgtaa gaaatgttct tgcagttaag ggttagttta caatcagcca
1681  cattctaggt agggcccac ttcaccgtac agctgtccct cactgttgaa
1741  tttctctaa cttcaaggcc catatctgtg aaatgctggc atttgcacct acctcacaga
1801  gtgcattgtg agggttaatg aaataatgta catctggcct tgaaaccacc tttattaca
1861  tggggtctag aacttgaccc cctgagggt gcttgttccc tctccctgtt ggtcggtggg
1921  ttgtagttt ctacagttgg gcagctggtt agtagaggg agttgtcaag tctctgctgg
1981  cccagccaaa cccctgtctga caacctcttg gtgaaccta gtacctaaaa ggaaatctca
2041  cccatccca cttgttcatct cttgtatatg cttgtatttt tctttttctt
2101  cttgttttat gctcaggtc aattctctt ttctttttt tggcgtgatc ttggcttact
2161  tgagactggg tctcgctttg ttgcccaggc tcgagcagtc ctgcctcagc gctggacca
2221  gcagcctttg cctccccggc ccaccaactt cagccaactt ttgcgtgttt gggtctcaca
2281  caggttcatg ccaccatggc cgctgtctc aaactcctgg gctcaggcga tccacctgtc tcagcctccc
2341  gtgttgccca ggctgtctc gattacaatt gtgagccacc acgtccagct ggaagggtca acatctttta
2401  agagtgctgg gattacaatt gcacatctgc atttttccac caccccctcc ctcctctcc ctttttatat
2461  cattctgcaa gcacatctgc atttttccac caccccctcc ctcctctcc ctttttatat
2521  cccatttta tatcgatctc ttatttaca ataaacttt gctgccacct gtgtgtctga
2581  ggggtg
```

FIG. 12 (CONTINUED)

MEEPQSDPSVEPPLSQETFSDLWKLLPENNVLSPLPSQAMDDLMLSPDDIEQWFT
EDPGPDEAPRMPEAAPPVAPAPAAPTPAAPAPAPSWPLSSSVPSQKTYQGSYGFR
LGFLHSGTAKSVTCTYSPALNKMFCQLAKTCPVQLWVDSTPPPGTRVRAMAIYK
QSQHMTEVVRRCPHHERCSDSDGLAPPQHLIRVEGNLRVEYLDDRNTFRHSVVV
PYEPPEVGSDCTTIHYNYMCNSSCMGGMNRRPILTIITLEDSSGNLLGRNSFEVRV
CACPGRDRRTEEENLRKKGEPHHELPPGSTKRALPNNTSSSPQPKKKPLDGEYFT
LQIRGRERFEMFRELNEALELKDAQAGKEPGGSRAHSSHLKSKKGQSTSRHKKL
MFKTEGPDSD

FIG. 13

```
   1  gattgggtt ttcccctccc atgtgctcaa gactggcgct aaaagttttg agcttctcaa
  61  aagtctagag ccaccgtcca gggagcaggt agctgctggg ctccggggac actttgcgtt
 121  cggctggga gcgtgctttc cacgacggtg aggagcttcc ctgattggc agccagactg
 181  ccttccgggt cactgccatg gaggagccgc agtcgtcgag tacttcctga aaacaacgtt cccctctga
 241  gtcaggaaac attttcagac ctatgaaac ctatcctga tagcgtcgag aaacaacgtt ctgtcccct
 301  tgccgtccca agcaatggat gatttgatgc tgtccccgga cgatatttgaa caatggttca
 361  ctgaagaccc aggtccagat gaagctccca gaatgccaga ggctgctccc cccgtgcccc
 421  ctgcaccagc agctcctaca ccggcggcag acctaccagc cccctcctgg ccctgtcat
 481  cttctgtccc ttcccagaaa acctaccagg gcagctacgg tttccgtctg gcttcttgc
 541  attctggac agccaagtct gtgacttgca cgtactcccc tgctactccc caagatgttt
 601  gccaactggc caagacctgc cctgtgcagc cctgtgcagc tgtgggttga ttccacaccc ccgcccgca
 661  cccgcgtcc cgcccatggc atctacaagc agtcacagca catgacggag gttgtgaggc
 721  gctgccca aggaaatttg tgctcagata gcgatggtct ggccctcct cagcatcta
 781  tccgagtgga aggaaatttg cgtgtggagt atttggagt cagaacact tttcgacata
 841  gtgtgtggt gcccatgag ccgcctcagg tttggctctga ctgtaccacc atccactaca
 901  actacatgtg taacagttcc tgcatgggcg gcatgaaccg gaggcccatc ctcaccatca
 961  tcacactga agactctcca ggtaatctac tgggacggaa aggaagagaa cagcttttgag gtgcgtgttt
1021  gtgcctgtcc tgggagagac cggcgcacag cggagcact agcgagcact tctccgcaag aaagggagc
1081  ctcaccacga gctgccccca gggaccccca ccactggatg gagaatattt gcccaacaac accagctcct
1141  ctccccagcc aaagaagaaa ctgcccttag gagaatattt caccttcag atccgtgggc
1201  gtgagcgctt cgagatgttc cgagagctga atgaggcctt ggaactcaag gatgccagg
1261  ctgggaagga gccaggggg agcagggctc actccagcca cctgaagtcc aaaagggtc
```

FIG. 14

```
1321  agtctacctc  cgccataaa   aaactcatgt  tcaagacaga  agggcctgac  tcagactgac
1381  attctccact  tcttgttccc  cactgacagc  ctcccaccc   catctctccc  tccctgcca
1441  tttggttt    tgggtctttg  aaccctgct   tgcaataggt  gtgcgtcaga  agcaccagg
1501  acttccattt  gctttgtccc  gggctccac   tgaacaagtt  ggcctgcact  ggtgttttgt
1561  tgtggggagg  aggatgggga  gtaggacata  ttttaaggtt  tttaaggttt  tttactgtga
1621  gggatgtttg  ggagatgtaa  gaaatgttct  tgcagttaag  ggttagttta  caatcagcca
1681  cattctaggt  agggcccac   ttcaccgtac  taaccaggga  agctgtccct  cactgttgaa
1741  tttctctaa   cttcaaggcc  catatctgtg  aaatgctggc  atttgcacct  acctcacaga
1801  gtgcattgtg  agggttaatg  aaataatgta  catctggcct  tgaaccacc   ttttattaca
1861  tggggtctag  aacttgaccc  ccttgaggt   gcttgttccc  tctccctgtt  ggtcggtggg
1921  ttggtagttt  ctacagttgg  gcagctggtt  agtagaggg   agttgtcaag  tctctgctgg
1981  cccagccaaa  ccctgtctga  caacctcttg  gtgaaccta   gtacctaaaa  ggaaatctca
2041  cccatccca   cagcgttctt  gattcatct   cttgtatatg  atgatctgga  tccaccaaga
2101  cttgttttat  gctcagggtc  aattttcttt  ttcttttttt  tttttttt    tcttttcttt
2161  tgagactggg  tctcgctttg  ttgcccaggc  tggagtggag  tggcgtgatc  ttggcttact
2221  gcaccttg    cctcccccggc  tcgagcagtc  ctgcctcagc  ctccggagta  gctggacca
2281  caggttcatg  ccaccatggc  cagccaactt  tgcatgttt   tgtagagatg  gggtctcaca
2341  gtgttgccca  ggctggtctc  aaactcctgg  gctcaggcga  tccacctgtc  tcagcctccc
2401  agagtgctgg  gattacaatt  gtgagccagc  acgtccagct  ggaagggtca  acatctttta
2461  cattctgcaa  gcacatctgc  atttccaccc  cacccctccc  ctcctctcc   ctttttatat
2521  cccattttta  tatcgatctc  ttattttaca  ataaactt    gctgccacct  gtgtgtctga
2581  ggggtg
```

FIG. 14 (CONTINUED)

MEEPQSDPSVEPPLSQETFSDLWKLLPENNVLSPLPSQAMDDLMLSPDDIEQWFT
EDPGPDEAPRMPEAAPPVAPAPAAPTPAAPAPAPSWPLSSSVPSQKTYQGSYGFR
LGFLHSGTAKSVTCTYSPALNKMFCQLAKTCPVQLWVDSTPPPGTRVRAMAIYK
QSQHMTEVVRRCPHHERCSDSDGLAPPQHLIRVEGNLRVEYLDDRNTFRHSVVV
PYEPPQVGSDCTTIHYNYMCNSSCMGGMNRRPILTIITLEDSSGNLLGRNSFEVRV
CACPGRDRRTEEENLRKKGEPHHELPPGSTKRALPNNTSSSPQPKKKPLDGEYFT
LQIRGRERFEMFRELNEALELKDAQAGKEPGGSRAHSSHLKSKKGQSTSRHKKL
MFKTEGPDSD

FIG. 15

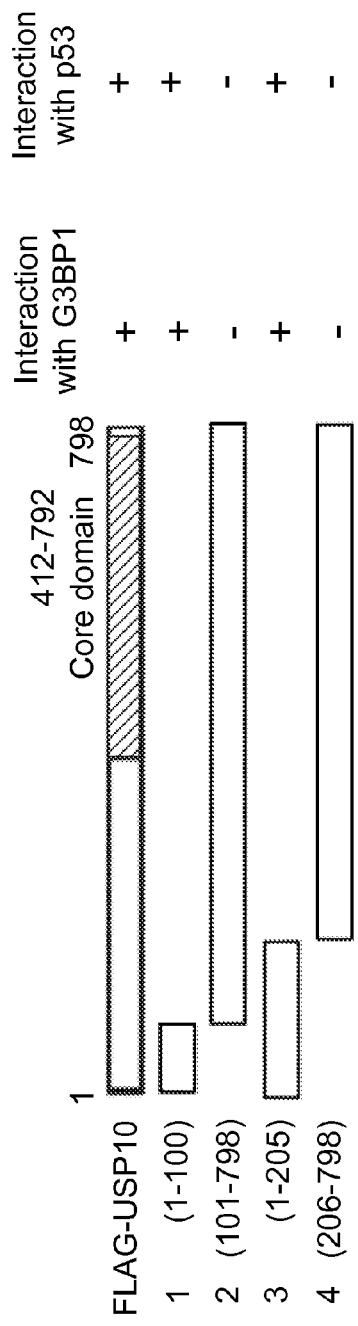
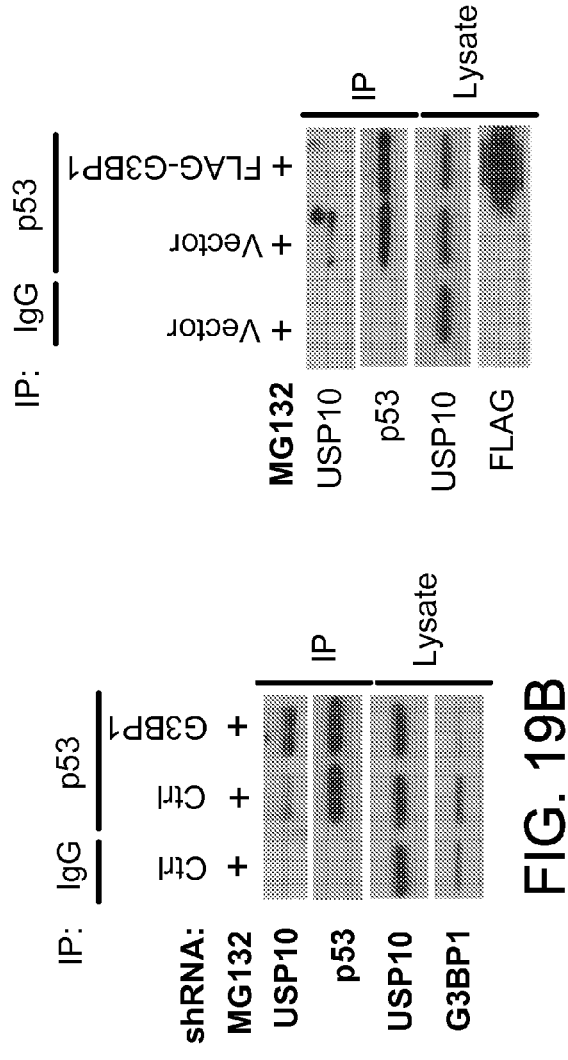
FIG. 19A
FIG. 19B
FIG. 19C

SEQUENCE LISTING

<160> NUMBER OF SEQ ID NOS: 13

<210> SEQ ID NO 1
<211> LENGTH: 3399
<212> TYPE: DNA
<213> ORGANISM: Homo sapiens

<400> SEQUENCE: 1

```
ctccccgcgc cccgcggcgc gcggccagtg cgcaggcgcg gcggccgatg cgagtgtgta        60
tgtgcgggcg agaagatggc ggcggcgggg gaagcagcgt gagcagccgg aggatcgcgg       120
agtcccaatg aaacgggcag ccatggccct ccacagcccg cagtatattt ttggagattt       180
tagccctgat gaattcaatc aattctttgt gactcctcga tcttcagttg agcttcctcc       240
atacagtgga acagttctgt gtggcacaca ggctgtggat aaactacctg atggacaaga       300
atatcagaga attgagtttg gtgtcgatga agtcattgaa cccagtgaca ctttgccgag       360
aacccccagc tacagtattt caagcacact gaaccctcag gcccctgaat ttattctcgg       420
ttgtacagct tccaaaataa cccctgatgg tatcactaaa gaagcaagct atggctccat       480
cgactgccag tacccaggct ctgccctcgc tttggatgga agttctaatg tggaggcgga       540
agttttggaa aatgatggtg tctcaggtgg tcttggacaa agggagcgta aaaagaagaa       600
aaagcggcca cctggatatt acagctattt gaaagatggt ggcgatgata gtatctccac       660
agaagccctg gtcaatggcc atgccaattc agcagtcccg aacagtgtca gtgcagagga       720
tgcagaattt atgggtgaca tgcccccgtc agttacgccc aggacttgta acagccccca       780
gaactccaca gactctgtca gtgacattgt gcctgacagt cctttccccg gagcactcgg       840
cagtgacacc aggactgcag ggcagccaga gggggcccc ggggctgatt ttggtcagtc       900
ctgcttccct gcagaggctg gcagagacac cctgtcaagg acagctgggg ctcagccctg       960
cgttggtacc gatactactg aaaaccttgg agttgctaat ggacaaatac ttgaatcctc      1020
gggtgagggc acagctacca acggggtgga gttgcacacc acgaaagca tagacttgga      1080 cccaaccaaa cccgagagtg catcacctcc tgctgacggc acgggctctg catcaggcac      1140
ccttcctgtc agccagccca gtcctgggc cagcctcttt catgattcta gccctcttc      1200 ctcctcgccg gtggcctatg tggaaactaa gtattcccct ccgccatat ctcccctggt      1260 ttctgaaaag caggttgaag tcaaagaagg gcttgttccg gtttcagagg atcctgtagc      1320
cataaagatt gcagagttgc tggagaatgt aaccctaatc cataaaccag tgtcgttgca      1380
accccgtggg ctgatcaata aagggaactg gtgctacatt aatgctacac tgcaggcatt      1440
ggttgcttgc ccgccgatgt accacctgat gaagttcatt cctctgtatt ccaaagtgca      1500
aaggccttgt acgtcaacac ccatgataga cagctttgtt cggctaatga atgagttcac      1560
taatatgcca gtacctccaa aaccccgaca agctcttgga gataaaatcg tgagggatat      1620
tcgccctgga gctgcctttg agcccacata tatttacaga ctcctgacag ttaacaagtc      1680
aagcctgtct gaaaagggtc gacaagaaga tgctgaggaa tacttaggct tcattctaaa      1740
tggacttcat gaggaaatgt tgaacctaaa gaagcttctc tcaccaagta atgaaaaact      1800 tacgattttcc aacggcccca aaaaccactc ggtcaatgaa gaagagcagg aagaacaagg      1860
tgaaggaagc gaggatgaat gggaacaagt gggcccccgg aacaagactt ccgtcacccg      1920
ccaggcggat tttgttcaga ctccaatcac cggcatttt ggtggacaca tcaggtctgt      1980
```

```
ggtttaccag cagagttcaa aagaatctgc cactttgcag ccattttca cgttgcagtt      2040 ggatatccag tcagacaaga tacgcacagt ccaggatgca ctggagagct tggtggcaag      2100
agaatctgtc caaggttata ccacaaaaac caaacaagag gttgagataa gtcgaagagt      2160
gactctggaa aaactccctc ctgtcctcgt gctgcacctg aaacgattcg tttatgagaa      2220
gactggtggg tgccagaagc ttatcaaaaa tattgaatat cctgtggact tggaaattag      2280
taaagaactg ctttctccag gggttaaaaa taagaatttt aaatgccacc gaacctatcg      2340
gctctttgca gtggtctacc atcacggcaa cagtgcgacg ggcggccatt acactacaga      2400
cgtcttccag atcggtctga atggctggct gcgcatcgat gaccagacag tcaaggtgat      2460
caaccagtac caggtggtga accaactgc tgaacgcaca gcctacctcc tgtattaccg      2520
ccgagtggac ctgctgtaaa ccctgtgtgc gctgtgtgtg cgcccagtgc cgcttcgta      2580 ggacaccacc tcacactcac ttcccgcctc tctttagtgg ctctttagag agaaactctt      2640
tctccctttg caaaaatggg ctagaatgaa aaggagatgc cttggggttc gtgcacaaca      2700
cagcttctgt tgactctaac ttccaaatca aaatcatttg gttgaaacag actgttgctt      2760
gattttagaa aatacacaaa aacccatatt tctgaaataa tgctgattcc tgagataaga      2820
aagtggattt gatccccagt ctcattgctt agtagaataa atcctgcacc agcaacaaca      2880
cttgtaaatt tgtgaaaatg aattttatct ttccttaaaa aagaaatttt ttaatccatc      2940
acacttttct tccctacccct ttagttttg ataaatgata aaaatgagcc agttatcaaa      3000
gaagaactag ttcttacttc aaaagaaaaa taaacataaa aaataagttg ctggttccta      3060
acaggaaaaa ttttaataat tgtactgaga gaaactgctt acgtacacat tgcagatcaa      3120
atatttggag ttaaaatgtt agtctacata gatgggtgat tgtaacttta ttgccattaa      3180
aagatttcaa attgcattca tgcttctgtg tacacataat gaaaaatggg caaataatga      3240
agatctctcc ttcagtctgc tctgtttaat tctgctgtct gctcttctct aatgctgcgt      3300
ccctaattgt acacagttta gtgatatcta ggagtataaa gttgtcgccc atcaataaaa      3360
atcacaaagt tggtttaaaa aaaaaaaaaa aaaaaaaaa                             3399
```

<210> SEQ ID NO 2
<211> LENGTH: 798
<212> TYPE: PRT
<213> ORGANISM: Homo sapiens

<400> SEQUENCE: 2

```
Met Ala Leu His Ser Pro Gln Tyr Ile Phe Gly Asp Phe Ser Pro Asp
 1               5                  10                  15

Glu Phe Asn Gln Phe Phe Val Thr Pro Arg Ser Ser Val Glu Leu Pro
                20                  25                  30

Pro Tyr Ser Gly Thr Val Leu Cys Gly Thr Gln Ala Val Asp Lys Leu
            35                  40                  45

Pro Asp Gly Gln Glu Tyr Gln Arg Ile Glu Phe Gly Val Asp Glu Val
        50                  55                  60

Ile Glu Pro Ser Asp Thr Leu Pro Arg Thr Pro Ser Tyr Ser Ile Ser
 65                  70                  75                  80

Ser Thr Leu Asn Pro Gln Ala Pro Glu Phe Ile Leu Gly Cys Thr Ala
                85                  90                  95

Ser Lys Ile Thr Pro Asp Gly Ile Thr Lys Glu Ala Ser Tyr Gly Ser
            100                 105                 110

Ile Asp Cys Gln Tyr Pro Gly Ser Ala Leu Ala Leu Asp Gly Ser Ser
        115                 120                 125
```

-continued

```
Asn Val Glu Ala Glu Val Leu Glu Asn Asp Gly Val Ser Gly Gly Leu
    130                 135                 140
Gly Gln Arg Glu Arg Lys Lys Lys Lys Arg Pro Pro Gly Tyr Tyr
145                 150                 155                 160
Ser Tyr Leu Lys Asp Gly Gly Asp Ser Ile Ser Thr Glu Ala Leu
                165                 170                 175
Val Asn Gly His Ala Asn Ser Ala Val Pro Asn Ser Val Ser Ala Glu
            180                 185                 190
Asp Ala Glu Phe Met Gly Asp Met Pro Pro Ser Val Thr Pro Arg Thr
        195                 200                 205
Cys Asn Ser Pro Gln Asn Ser Thr Asp Ser Val Ser Asp Ile Val Pro
210                 215                 220
Asp Ser Pro Phe Pro Gly Ala Leu Gly Ser Asp Thr Arg Thr Ala Gly
225                 230                 235                 240
Gln Pro Glu Gly Gly Pro Gly Ala Asp Phe Gly Gln Ser Cys Phe Pro
                245                 250                 255
Ala Glu Ala Gly Arg Asp Thr Leu Ser Arg Thr Ala Gly Ala Gln Pro
            260                 265                 270
Cys Val Gly Thr Asp Thr Thr Glu Asn Leu Gly Val Ala Asn Gly Gln
        275                 280                 285
Ile Leu Glu Ser Ser Gly Glu Gly Thr Ala Thr Asn Gly Val Glu Leu
290                 295                 300
His Thr Thr Glu Ser Ile Asp Leu Asp Pro Thr Lys Pro Glu Ser Ala
305                 310                 315                 320
Ser Pro Pro Ala Asp Gly Thr Gly Ser Ala Ser Gly Thr Leu Pro Val
                325                 330                 335
Ser Gln Pro Lys Ser Trp Ala Ser Leu Phe His Asp Ser Lys Pro Ser
            340                 345                 350
Ser Ser Ser Pro Val Ala Tyr Val Glu Thr Lys Tyr Ser Pro Pro Ala
        355                 360                 365
Ile Ser Pro Leu Val Ser Glu Lys Gln Val Glu Val Lys Glu Gly Leu
370                 375                 380
Val Pro Val Ser Glu Asp Pro Val Ala Ile Lys Ile Ala Glu Leu Leu
385                 390                 395                 400
Glu Asn Val Thr Leu Ile His Lys Pro Val Ser Leu Gln Pro Arg Gly
                405                 410                 415
Leu Ile Asn Lys Gly Asn Trp Cys Tyr Ile Asn Ala Thr Leu Gln Ala
            420                 425                 430
Leu Val Ala Cys Pro Pro Met Tyr His Leu Met Lys Phe Ile Pro Leu
        435                 440                 445
Tyr Ser Lys Val Gln Arg Pro Cys Thr Ser Thr Pro Met Ile Asp Ser
450                 455                 460
Phe Val Arg Leu Met Asn Glu Phe Thr Asn Met Pro Val Pro Pro Lys
465                 470                 475                 480
Pro Arg Gln Ala Leu Gly Asp Lys Ile Val Arg Asp Ile Arg Pro Gly
                485                 490                 495
Ala Ala Phe Glu Pro Thr Tyr Ile Tyr Arg Leu Leu Thr Val Asn Lys
            500                 505                 510
Ser Ser Leu Ser Glu Lys Gly Arg Gln Glu Asp Ala Glu Glu Tyr Leu
        515                 520                 525
Gly Phe Ile Leu Asn Gly Leu His Glu Glu Met Leu Asn Leu Lys Lys
530                 535                 540
```

```
Leu Leu Ser Pro Ser Asn Glu Lys Leu Thr Ile Ser Asn Gly Pro Lys
545                 550                 555                 560

Asn His Ser Val Asn Glu Glu Gln Glu Gln Gly Glu Gly Ser
            565                 570                 575

Glu Asp Glu Trp Glu Gln Val Gly Pro Arg Asn Lys Thr Ser Val Thr
                580                 585                 590

Arg Gln Ala Asp Phe Val Gln Thr Pro Ile Thr Gly Ile Phe Gly Gly
            595                 600                 605

His Ile Arg Ser Val Val Tyr Gln Gln Ser Ser Lys Glu Ser Ala Thr
            610                 615                 620

Leu Gln Pro Phe Phe Thr Leu Gln Leu Asp Ile Gln Ser Asp Lys Ile
625                 630                 635                 640

Arg Thr Val Gln Asp Ala Leu Glu Ser Leu Val Ala Arg Glu Ser Val
            645                 650                 655

Gln Gly Tyr Thr Thr Lys Thr Lys Gln Glu Val Glu Ile Ser Arg Arg
            660                 665                 670

Val Thr Leu Glu Lys Leu Pro Pro Val Leu Val Leu His Leu Lys Arg
            675                 680                 685

Phe Val Tyr Glu Lys Thr Gly Gly Cys Gln Lys Leu Ile Lys Asn Ile
690                 695                 700

Glu Tyr Pro Val Asp Leu Glu Ile Ser Lys Glu Leu Leu Ser Pro Gly
705                 710                 715                 720

Val Lys Asn Lys Asn Phe Lys Cys His Arg Thr Tyr Arg Leu Phe Ala
            725                 730                 735

Val Val Tyr His His Gly Asn Ser Ala Thr Gly Gly His Tyr Thr Thr
            740                 745                 750

Asp Val Phe Gln Ile Gly Leu Asn Gly Trp Leu Arg Ile Asp Asp Gln
            755                 760                 765

Thr Val Lys Val Ile Asn Gln Tyr Gln Val Val Lys Pro Thr Ala Glu
            770                 775                 780

Arg Thr Ala Tyr Leu Leu Tyr Tyr Arg Arg Val Asp Leu Leu
785                 790                 795

<210> SEQ ID NO 3
<211> LENGTH: 2586
<212> TYPE: DNA
<213> ORGANISM: Homo sapiens

<400> SEQUENCE: 3
gattggggtt tccccctccc atgtgctcaa gactggcgct aaaagttttg agcttctcaa      60
aagtctagag ccaccgtcca gggagcaggt agctgctggg ctccggggac actttgcgtt     120
cgggctggga gcgtgctttc cacgacggtg acacgcttcc ctggattggc agccagactg     180
ccttccgggt cactgccatg gaggagccgc agtcagatcc tagcgtcgag ccccctctga     240
gtcaggaaac attttcagac ctatggaaac tacttcctga aaacaacgtt ctgtccccct     300
tgccgtccca agcaatggat gatttgatgc tgtccccgga cgatattgaa caatggttca     360
ctgaagaccc aggtccagat gaagctccca gaatgccaga ggctgctccc cccgtggccc     420
ctgcaccagc agctcctaca ccggcggccc ctgcaccagc ccctcctgg ccctgtcat      480 cttctgtccc ttcccagaaa acctaccagg gcagctacgg tttccgtctg ggcttcttgc     540
attctgggac agccaagtct gtgacttgca cgtactcccc tgccctcaac aagatgtttt     600
gccaactggc caagacctgc cctgtgcagc tgtgggttga ttccacaccc ccgcccggca     660
cccgcgtccg cgccatggcc atctacaagc agtcacagca catgacggag gttgtgaggc     720
```

```
gctgccccca ccatgagcgc tgctcagata gcgatggtct ggcccctcct cagcatctta      780
tccgagtgga aggaaatttg cgtgtggagt atttggatga cagaaacact tttcgacata      840
gtgtggtggt gccctatgag ccgcctgagg ttggctctga ctgtaccacc atccactaca      900
actacatgtg taacagttcc tgcatgggcg gcatgaaccg gaggcccatc ctcaccatca      960
tcacactgga agactccagt ggtaatctac tgggacggaa cagctttgag gtgcgtgttt     1020
gtgcctgtcc tgggagagac cggcgcacag aggaagagaa tctccgcaag aaagggagc     1080
ctcaccacga gctgccccca gggagcacta agcgagcact gcccaacaac accagctcct     1140
ctccccagcc aaagaagaaa ccactggatg agaatatttt cacccttcag atccgtgggc     1200
gtgagcgctt cgagatgttc cgagagctga atgaggcctt ggaactcaag gatgcccagg     1260
ctgggaagga gccagggggg agcagggctc actccagcca cctgaagtcc aaaaagggtc     1320
agtctaccte ccgccataaa aaactcatgt tcaagacaga agggcctgac tcagactgac     1380
attctccact tcttgttccc cactgacagc ctcccacccc catctctccc tcccctgcca     1440
ttttgggttt tgggtctttg aacccttgct tgcaataggt gtgcgtcaga agcacccagg     1500
acttccattt gctttgtccc ggggctccac tgaacaagtt ggcctgcact ggtgttttgt     1560
tgtggggagg aggatgggga gtaggacata ccagcttaga ttttaaggtt tttactgtga     1620
gggatgtttg ggagatgtaa gaaatgttct tgcagttaag ggttagttta caatcagcca     1680
cattctaggt aggggcccac ttcaccgtac taaccaggga agctgtccct cactgttgaa     1740
ttttctctaa cttcaaggcc catatctgtg aaatgctggc atttgcacct acctcacaga     1800
gtgcattgtg agggttaatg aaataatgta catctggcct tgaaaccacc ttttattaca     1860
tggggtctag aacttgaccc ccttgagggt gcttgttccc tctccctgtt ggtcggtggg     1920
ttggtagttt ctacagttgg gcagctggtt aggtagaggg agttgtcaag tctctgctgg     1980
cccagccaaa ccctgtctga caacctcttg gtgaacctta gtacctaaaa ggaaatctca     2040
ccccatccca caccctggag gatttcatct cttgtatatg atgatctgga tccaccaaga     2100
cttgttttat gctcagggtc aatttctttt ttcttttttt tttttttttt tctttttctt     2160
tgagactggg tctcgctttg ttgcccaggc tggagtggag tggcgtgatc ttggcttact     2220
gcagcctttg cctccccggc tcgagcagtc ctgcctcagc ctccggagta gctgggacca     2280
caggttcatg ccaccatggc cagccaactt ttgcatgttt tgtagagatg ggtctcaca     2340
gtgttgccca ggctggtctc aaactcctgg gctcaggcga tccacctgtc tcagcctccc     2400
agagtgctgg gattacaatt gtgagccacc acgtccagct ggaagggtca acatcttta     2460
cattctgcaa gcacatctgc attttcaccc caccttccc ctccttctcc ctttttatat     2520
cccattttta tatcgatctc ttattttaca ataaaacttt gctgccacct gtgtgtctga     2580
ggggtg                                                                2586

<210> SEQ ID NO 4
<211> LENGTH: 393
<212> TYPE: PRT
<213> ORGANISM: Homo sapiens

<400> SEQUENCE: 4

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30
```

```
Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
 210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
 290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
 370                 375                 380

Phe Lys Thr Glu Gly Pro Asp Ser Asp
385                 390

<210> SEQ ID NO 5
<211> LENGTH: 2586
<212> TYPE: DNA
<213> ORGANISM: Homo sapiens
```

```
<400> SEQUENCE: 5
gattggggtt tccccctccc atgtgctcaa gactggcgct aaaagttttg agcttctcaa        60
aagtctagag ccaccgtcca gggagcaggt agctgctggg ctccggggac actttgcgtt       120
cgggctggga gcgtgctttc cacgacggtg acacgcttcc ctggattggc agccagactg       180
ccttccgggt cactgccatg gaggagccgc agtcagatcc tagcgtcgag cccctctga        240
gtcaggaaac attttcagac ctatggaaac tacttcctga aaacaacgtt ctgtcccct        300
tgccgtccca agcaatggat gatttgatgc tgtccccgga cgatattgaa caatggttca       360
ctgaagaccc aggtccagat gaagctccca gaatgccaga ggctgctccc ccgtggccc        420
ctgcaccagc agctcctaca ccggcggccc ctgcaccagc ccctcctgg ccctgtcat         480
cttctgtccc ttcccagaaa acctaccagg gcagctacgg tttccgtctg gcttcttgc        540
attctgggac agccaagtct gtgacttgca cgtactcccc tgccctcaac aagatgtttt       600
gccaactggc caagacctgc cctgtgcagc tgtgggttga ttccacaccc ccgcccggca       660
cccgcgtccg cgccatggcc atctacaagc agtcacagca catgacggag gttgtgaggc       720
gctgcccca ccatgagcgc tgctcagata gcgatggtct ggcccctcct cagcatctta       780
tccgagtgga aggaaatttg cgtgtggagt atttggatga cagaaacact ttcgacata        840
gtgtggtggt gccctatgag ccgcctcagg ttggctctga ctgtaccacc atccactaca       900
actacatgtg taacagttcc tgcatgggcg gcatgaaccg gaggcccatc ctcaccatca       960
tcacactgga agactccagt ggtaatctac tgggacggaa cagctttgag gtgcgtgttt      1020
gtgcctgtcc tgggagagac cggcgcacag aggaagagaa tctccgcaag aaaggggagc      1080
ctcaccacga gctgccccca gggagcacta gcgagcact gcccaacaac accagctcct      1140
ctccccagcc aaagaagaaa ccactggatg agaatattt cacccttcag atccgtgggc      1200
gtgagcgctt cgagatgttc cgagagctga atgaggcctt ggaactcaag gatgcccagg      1260
ctgggaagga gccaggggg agcagggctc actccagcca cctgaagtcc aaaaagggtc      1320
agtctacctc ccgccataaa aaactcatgt tcaagacaga agggcctgac tcagactgac      1380
attctccact tcttgttccc cactgacagc ctcccacccc catctctccc tccctgcca     1440
ttttgggttt tgggtctttg aacccttgct tgcaataggt gtgcgtcaga agcacccagg      1500
acttccattt gctttgtccc ggggctccac tgaacaagtt ggcctgcact ggtgttttgt     1560
tgtggggagg aggatgggga gtaggacata ccagcttaga ttttaaggtt tttactgtga      1620
gggatgtttg ggagatgtaa gaaatgttct tgcagttaag ggttagttta caatcagcca      1680
cattctaggt aggggcccac ttcaccgtac taaccaggga agctgtccct cactgttgaa      1740
ttttctctaa cttcaaggcc catatctgtg aaatgctggc atttgcacct acctcacaga      1800
gtgcattgtg agggttaatg aaataatgta catctggcct tgaaaccacc ttttattaca      1860
tggggtctag aacttgaccc ccttgagggt gcttgttccc tctccctgtt ggtcggtggg      1920
ttggtagttt ctacagttgg gcagctggtt aggtagaggg agttgtcaag tctctgctgg      1980
cccagccaaa ccctgtctga caacctcttg gtgaacctta gtacctaaaa ggaaatctca      2040
ccccatccca caccctggag gatttcatct cttgtatatg atgatctgga tccaccaaga      2100
cttgttttat gctcagggtc aatttctttt ttcttttttt ttttttttt tcttttttctt      2160
tgagactggg tctcgctttg ttgcccaggc tggagtggag tggcgtgatc ttggcttact      2220
gcagcctttg cctcccggc tcgagcagtc ctgcctcagc ctccgagta gctgggacca      2280
caggttcatg ccaccatggc cagccaactt ttgcatgttt tgtagagatg gggtctcaca      2340
```

```
gtgttgccca ggctggtctc aaactcctgg gctcaggcga tccacctgtc tcagcctccc    2400
agagtgctgg gattacaatt gtgagccacc acgtccagct ggaagggtca acatctttta    2460
cattctgcaa gcacatctgc attttcaccc cacccttccc ctccttctcc ctttttatat    2520
cccattttta tatcgatctc ttattttaca ataaaacttt gctgccacct gtgtgtctga    2580
ggggtg                                                              2586

<210> SEQ ID NO 6
<211> LENGTH: 393
<212> TYPE: PRT
<213> ORGANISM: Homo sapiens

<400> SEQUENCE: 6
```

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Gln
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

```
Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 7
<211> LENGTH: 21
<212> TYPE: DNA
<213> ORGANISM: Homo sapiens

<400> SEQUENCE: 7
gcctctcttt agtggctctt t                                           21

<210> SEQ ID NO 8
<211> LENGTH: 21
<212> TYPE: DNA
<213> ORGANISM: Homo sapiens

<400> SEQUENCE: 8
cctatgtgga aactaagtat t                                           21

<210> SEQ ID NO 9
<211> LENGTH: 21
<212> TYPE: DNA
<213> ORGANISM: Homo sapiens

<400> SEQUENCE: 9
cccatgatag acagctttgt t                                           21

<210> SEQ ID NO 10
<211> LENGTH: 21
<212> TYPE: DNA
<213> ORGANISM: Homo sapiens

<400> SEQUENCE: 10
gctgtggata aactacctga t                                           21

<210> SEQ ID NO 11
<211> LENGTH: 21
<212> TYPE: DNA
<213> ORGANISM: Homo sapiens

<400> SEQUENCE: 11
cgacaagctc ttggagataa a                                           21

<210> SEQ ID NO 12
<211> LENGTH: 19
<212> TYPE: DNA
<213> ORGANISM: Homo sapiens

<400> SEQUENCE: 12
atgtttcatt cattggaat                                              19
```

```
<210> SEQ ID NO 13
<211> LENGTH: 21
<212> TYPE: DNA
<213> ORGANISM: Homo sapiens

<400> SEQUENCE: 13
gcctctcttt agtggctctt t                                              21
```

METHODS AND MATERIALS FOR MODULATING DEUBIQUITINASES AND UBIQUITINATED POLYPEPTIDES

CROSS-REFERENCE TO RELATED APPLICATIONS

This application is a National Stage application under 35 U.S.C. 371 and claims benefit under 35 U.S.C. 119(a) of International Application No. PCT/US2010/048302, having an International Filing Date of Sep. 9, 2010, which claims the benefit of U.S. Provisional Application Ser. No. 61/260,637, filed Nov. 12, 2009 and U.S. Provisional Application Ser. No. 61/241,152, filed Sep. 10, 2009. The disclosures of the prior applications are considered part of (and are incorporated by reference in) the disclosure of this application.

BACKGROUND

1. Technical Field

This document relates to methods and materials involved in modulating deubiquitinases and ubiquitinated polypeptides (e.g., tumor suppressors such as wild-type p53 polypeptides). For example, this document relates to methods and materials for increasing or decreasing deubiquitinase expression or activity, methods and materials for stabilizing or de-stabilizing ubiquitinated polypeptides, and methods and materials for treating cancer.

2. Background Information p53 is a tumor suppressor that is mutated in more than 50% of human cancers and whose major function is regulating cell fate following cellular stress and repressing the propagation of damaged cells (Lane, 1992; Riley et al., 2008; Vogelstein et al., 2000). p53 functions as a transcription factor, and through its target genes regulates a variety of cellular functions, from cellular senescence, to energy metabolism, DNA repair, cell differentiation, cell cycle progression and apoptosis. In addition to the activation of transcription, p53 can also act as a repressor of transcription, as it does in the suppression of CD44, a protein implicated in tumorigenesis (Godar et al., 2008). Finally, p53 also has transcription-independent functions, such as regulating apoptosis through protein-protein interactions (Moll et al., 2005).

SUMMARY

This document relates to methods and materials involved in modulating deubiquitinases (e.g., USP10 polypeptides) and/or ubiquitinated polypeptides (e.g., tumor suppressor polypeptides or mutant versions of tumor suppressor polypeptides). For example, this document provides methods and materials for increasing deubiquitinase (e.g., a USP10 polypeptide) expression or activity, methods and materials for decreasing deubiquitinase (e.g., a USP10 polypeptide) expression or activity, methods and materials for stabilizing tumor suppressor polypeptides (e.g., wild-type p53 polypeptides), methods and materials for de-stabilizing mutant versions of tumor suppressor polypeptides (e.g., mutant p53 polypeptides), and methods and materials for reducing cancer cell proliferation, increasing cancer cell apoptosis, and/or treating cancer (e.g., cancers having reduced levels of wild-type p53 polypeptides or cancers having increased levels of mutant p53 polypeptides). This document also provides methods and materials for identifying agonists or antagonists of USP10 mediated stabilization of p53 polypeptides.

Some cancer cells can express reduced levels of p53 polypeptides, while other cancer cells can express average or elevated levels of a mutant version of a p53 polypeptide. As described herein, USP10 polypeptides can interact with and deubiquinate wild-type or mutant p53 polypeptides, thereby increasing their stability. In the cases of cancer cells having reduced levels of wild-type p53 polypeptides, the methods and materials provided herein can be used to increase USP10 polypeptide expression or activity, thereby increasing the stability of the wild-type p53 polypeptides. This can result in an increased level of wild-type p53 polypeptides within the cancer cells, thereby resulting in reduced cancer cell proliferation and increased cancer cell apoptosis. In the cases of cancer cells that express mutant p53 polypeptides, the methods and materials provided herein can be used to decrease USP10 polypeptide expression or activity, thereby decreasing the stability of the mutant p53 polypeptides. This can result in a decreased level of mutant p53 polypeptides within the cancer cells, thereby resulting in reduced cancer cell proliferation and increased cancer cell apoptosis.

In general, one aspect of this document features a method for reducing cancer cell proliferation in a mammal having cancer cells. The method comprises, or consists essentially of, administering a composition to the mammal under conditions wherein the composition modulates USP10 polypeptide expression or activity within the cancer cells, thereby reducing cancer cell proliferation. The cancer cells can have a reduced level of wild-type p53 polypeptide expression, and the composition can increase USP10 polypeptide expression or activity. The composition can comprise nucleic acid encoding a USP10 polypeptide. The composition can comprise nucleic acid encoding a polypeptide having the amino acid sequence set forth in SEQ ID NO:2. The cancer cells can express a mutant version of a p53 polypeptide, and the composition can decrease USP10 polypeptide expression or activity. The composition can comprise an antagonist of USP10 polypeptide mediated stabilization of p53 polypeptides. The antagonist can comprise nucleic acid having the ability to induce RNA interference against expression of the USP10 polypeptide. The USP10 polypeptide can be a human USP10 polypeptide.

In another aspect, this document features a method for treating cancer in a mammal. The method comprises, or consists essentially of, (a) identifying a mammal as having cancer cells that express a reduced level of wild-type p53 polypeptides or that express a mutant p53 polypeptide, (b) administering a USP10 polypeptide or a composition that increases USP10 polypeptide expression or activity within the cancer cells if the mammal is identified as having cancer cells that express the reduced level of wild-type p53 polypeptides, and (c) administering a composition that decreases USP10 polypeptide expression or activity within the cancer cells if the mammal is identified as having cancer cells that express the mutant p53 polypeptide.

In another aspect, this document features a method for identifying an antagonist of USP10 polypeptide mediated stabilization of p53 polypeptides. The method comprises, or consists essentially of, determining if the stabilization level of a ubiquinated p53 polypeptide contacted with a USP10 polypeptide in the presence of a test agent is less than the stabilization level of the ubiquinated p53 polypeptide contacted with the USP10 polypeptide in the absence of the test agent, wherein the presence of the stabilization level of the ubiquinated p53 polypeptide contacted with the USP10 polypeptide in the presence of the test agent that is less than the stabilization level of the ubiquinated p53 polypeptide contacted with the USP10 polypeptide in the absence of the test agent indicates that the test agent is the antagonist.

In another aspect, this document features a method for identifying an agonist of USP10 polypeptide mediated stabilization of p53 polypeptides. The method comprises, or consists essentially of, determining if the stabilization level of a ubiquinated p53 polypeptide contacted with a USP10 polypeptide in the presence of a test agent is greater than the stabilization level of the ubiquinated p53 polypeptide contacted with the USP10 polypeptide in the absence of the test agent, wherein the presence of the stabilization level of the ubiquinated p53 polypeptide contacted with the USP10 polypeptide in the presence of the test agent that is greater than the stabilization level of the ubiquinated p53 polypeptide contacted with the USP10 polypeptide in the absence of the test agent indicates that the test agent is the agonist.

In another aspect, this document features a method for assessing the p53 genotype of a cancer cell. The method comprises, or consists essentially of, determining the level of USP10 polypeptide expression in the cancer cell, diagnosing the cancer cell as having wild-type p53 if the cancer cell contains a reduced level of USP10 polypeptide expression, and diagnosing the cancer cell as having mutant p53 if the cancer cell contains an increased level of USP10 polypeptide expression.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 9 is a listing of a nucleic acid sequence (SEQ ID NO:1) that encodes a human USP10 polypeptide.

FIG. 10 is a listing of an amino acid sequence of a human USP10 polypeptide (SEQ ID NO:2).

FIG. 11 contains a list of shRNAs that can target nucleic acid encoding a human USP10 polypeptide.

FIG. 12 is a listing of a nucleic acid sequence (SEQ ID NO:3) that encodes a human p53 polypeptide.

FIG. 13 is a listing of an amino acid sequence of a human p53 polypeptide (SEQ ID NO:4).

FIG. 14 is a listing of a nucleic acid sequence (SEQ ID NO:5) that encodes a mutant version of a human p53 polypeptide.

FIG. 15 is a listing of an amino acid sequence of a mutant version of a human p53 polypeptide (SEQ ID NO:6).

FIG. 19A is a schematic diagram of USP10 polypeptides (e.g., full length and fragments of full length USP10 polypeptides) with a table indicating that both G3BP1 polypeptides and p53 polypeptides interact with the N-terminal region (e.g., 1-100 amino acids) of USP10 polypeptides. FIG. 19B is a photograph of an immunoprecipitation of HCT116 cell lysates with an anti-p53 polypeptide antibody (or control antibody, IgG) and immunoblotted with anti-USP10 polypeptide antibodies, anti-p53 polypeptide antibodies, or anti-G3BP1 polypeptide antibodies. The HCT116 cell lysates were obtained from cells treated with MG132 and either control shRNA (Ctrl) or shRNA designed to reduce G3BP1 polypeptide expression (G3BP1). FIG. 19C is a photograph of an immunoprecipitation of HCT116 cell lysates with an anti-p53 polypeptide antibody (or control antibody, IgG) and immunoblotted with anti-USP10 polypeptide antibodies, anti-p53 polypeptide antibodies, or anti-FLAG antibodies. The HCT116 cell lysates were obtained from cells treated with MG132 and either a control vector (Vector) or a vector designed to overexpress G3BP1 polypeptides (FLAG-G3BP1).

DETAILED DESCRIPTION

Figure 1A:
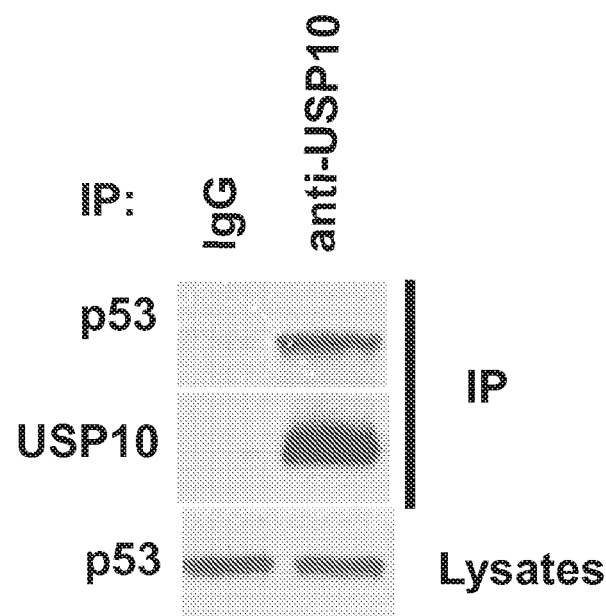
FIG. 1. USP10 interacts with p53. (A and D) U2OS cell lysates were subjected to immunoprecipitation with control IgG or anti-USP10 antibodies. The immunoprecipitates were then blotted with anti-p53, anti-Mdm2, or anti-USP10 antibodies. (B and C) HCT116 p53$^{+/+}$ and p53$^{-/-}$ cell lysates were subjected to immunoprecipitation with control IgG or anti-USP10 antibodies (B) or anti-p53 antibodies (C). The immunoprecipitates were then blotted with anti-p53 or anti-USP10 antibodies. (HC: Heavy Chain). (E). Purified FLAG-tagged USP10 was incubated with GST or GST-p53 coupled to GSH-Sepharose. Proteins retained on Sepharose were then blotted with indicated antibodies. (F) Constructs encoding FLAG-tagged full-length (FL) or deletion mutations of USP10 were transfected into H1299 cells. Forty-eight hours after transfection, cells were lysed, and cell lysates were incubated with GST or GST-p53 coupled to GSH-Sepharose. Proteins retained on Sepharose were analyzed with the indicated antibody.

This document relates to methods and materials involved in modulating deubiquitinases (e.g., USP10 polypeptides) and/or ubiquitinated polypeptides (e.g., tumor suppressor polypeptides or mutant versions of tumor suppressor polypeptides). For example, this document provides methods and materials for increasing deubiquitinase (e.g., a USP10 polypeptide) expression or activity, methods and materials for decreasing deubiquitinase (e.g., a USP10 polypeptide) expression or activity, methods and materials for stabilizing tumor suppressor polypeptides (e.g., wild-type p53 polypeptides), methods and materials for de-stabilizing mutant versions of tumor suppressor polypeptides (e.g., mutant p53 polypeptides), and methods and materials for reducing cancer cell proliferation, increasing cancer cell apoptosis, and/or treating cancer (e.g., cancers having reduced levels of wild-type p53 polypeptides or cancers having increased levels of mutant p53 polypeptides). This document also provides methods and materials for identifying agonists or antagonists of USP10 mediated stabilization of p53 polypeptides.

In one embodiment, this document provides methods and materials related to treating mammals (e.g., humans) having cancer. Examples of mammals that can be treated as described herein include, without limitation, humans, monkeys, dogs, cats, cows, horses, pigs, rats, and mice. Examples of cancers that can be treated as described herein include, without limitation, renal cancers (e.g., renal cell carcinomas), pancreatic cancers, breast cancers, and glioma. A mammal can be identified as having cancer using any appropriate cancer diagnostic techniques. In some cases, a cancer can be assessed to determine if the cancer is a cancer with a reduced level of p53 polypeptides (e.g., wild-type p53 polypeptides). Any appropriate method can be used to assess the level of p53 polypeptides within cancer cells. For example, nucleic acid detection techniques such as RT-PCR or microarray assays can be used to assess the level of p53 mRNA within cancer cells or polypeptide detection techniques such as immunohistochemistry or ELISAs can be used to assess the level of p53 polypeptides within cancer cells.

As described herein, cancer having a reduced level of wild-type p53 polypeptides can be treated by increasing the level of USP10 polypeptide expression or activity. The increased level of USP10 polypeptide expression or activity can stabilize wild-type p53 polypeptides within the cancer cells, thereby resulting in reduced cancer cell proliferation and increased cancer cell apoptosis. In some cases, the level of USP10 polypeptide within cancer cells can be increased by administering a composition containing USP10 polypeptides. In some cases, the level of USP10 polypeptide expression or activity within cancer cells can be increased by administering a USP10 polypeptide agonist or a nucleic acid encoding a USP10 polypeptide to the cancer cells. Such a nucleic acid can encode a full-length USP10 polypeptide such as a human USP10 polypeptide having the amino acid sequence set forth in SEQ ID NO:2, or a biologically active fragment of a USP10 polypeptide having amino acid residues 520 to 793 of the sequence set forth in SEQ ID NO:2. A nucleic acid encoding a USP10 polypeptide or fragment thereof can be administered to a mammal using any appropriate method. For example, a nucleic acid can be administered to a mammal using a vector such as a viral vector.

Vectors for administering nucleic acids (e.g., a nucleic acid encoding a USP10 polypeptide or fragment thereof) to a mammal are known in the art and can be prepared using standard materials (e.g., packaging cell lines, helper viruses, and vector constructs). See, for example, *Gene Therapy Protocols (Methods in Molecular Medicine)*, edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). Virus-based nucleic acid delivery vectors are typically derived from animal viruses, such as adenoviruses, adeno-associated viruses, retroviruses, lentiviruses, vaccinia viruses, herpes viruses, and papilloma viruses. Lentiviruses are a genus of retroviruses that can be used to infect cells (e.g., cancer cells). Adenoviruses contain a linear double-stranded DNA genome that can be engineered to inactivate the ability of the virus to replicate in the normal lytic life cycle. Adenoviruses and adeno-associated viruses can be used to infect cancer cells.

Vectors for nucleic acid delivery can be genetically modified such that the pathogenicity of the virus is altered or removed. The genome of a virus can be modified to increase infectivity and/or to accommodate packaging of a nucleic acid, such as a nucleic acid encoding a USP10 polypeptide or fragment thereof. A viral vector can be replication-competent or replication-defective, and can contain fewer viral genes than a corresponding wild-type virus or no viral genes at all.

In addition to nucleic acid encoding a USP10 polypeptide or fragment thereof, a viral vector can contain regulatory elements operably linked to a nucleic acid encoding a USP10 polypeptide or fragment thereof. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding a USP10 polypeptide or fragment thereof. A promoter can be constitutive or inducible (e.g., in the presence of tetracycline), and can affect the expression of a nucleic acid encoding a USP10 polypeptide or fragment thereof in a general or tissue-specific manner. Tissue-specific promoters include, without limitation, enolase promoter, prion protein (PrP) promoter, and tyrosine hydroxylase promoter.

As used herein, "operably linked" refers to positioning of a regulatory element in a vector relative to a nucleic acid in such a way as to permit or facilitate expression of the encoded polypeptide. For example, a viral vector can contain a neuronal-specific enolase promoter and a nucleic acid encoding a USP10 polypeptide or fragment thereof. In this case, the enolase promoter is operably linked to a nucleic acid encoding a USP10 polypeptide or fragment thereof such that it drives transcription in neuronal tumor cells.

A nucleic acid encoding a USP10 polypeptide or fragment thereof also can be administered to cancer cells using non-viral vectors. Methods of using non-viral vectors for nucleic acid delivery are known to those of ordinary skill in the art. See, for example, *Gene Therapy Protocols (Methods in Molecular Medicine)*, edited by Jeffrey R. Morgan, Humana Press, Totowa, N.J. (2002). For example, a nucleic acid encoding a USP10 polypeptide or fragment thereof can be administered to a mammal by direct injection (e.g., an intra-tumoral injection) of nucleic acid molecules (e.g., plasmids) comprising nucleic acid encoding a USP10 polypeptide or fragment thereof, or by administering nucleic acid molecules complexed with lipids, polymers, or nanospheres.

A nucleic acid encoding a USP10 polypeptide or fragment thereof can be produced by standard techniques, including, without limitation, common molecular cloning, polymerase chain reaction (PCR), chemical nucleic acid synthesis techniques, and combinations of such techniques. For example PCR or RT-PCR can be used with oligonucleotide primers designed to amplify nucleic acid (e.g., genomic DNA or RNA) encoding a USP10 polypeptide or fragment thereof.

In some cases, a nucleic acid encoding a USP10 polypeptide or fragment thereof can be isolated from a healthy mammal or a mammal having cancer. For example, a nucleic acid that encodes a wild type USP10 polypeptide having the amino acid sequence set forth in SEQ ID NO:2 can be isolated from a human containing that nucleic acid. The isolated nucleic acid can then be used to generate a viral vector, for example, which can be administered to a mammal so that the level of a USP10 polypeptide or fragment thereof in cancer cells within the mammal is increased.

In some cases, a cancer can be assessed to determine if the cancer is a cancer that expresses a mutant version of a p53 polypeptide. Examples of mutant p53 polypeptide include, without limitation, those having the amino acid sequence as set forth elsewhere ("The UMD-p53 database: New mutations and analysis tools," Christophe Béroud and Thierry Soussi, Human Mutation, Volume 21: p. 176-181; and Berglind et al., *Cancer Biol. Ther.*, 7(5):699-708 (2008)). Any appropriate method can be used to assess cancer cells for a mutant version of a p53 polypeptide. For example, nucleic acid detection techniques such as RT-PCR or microarray assays can be used to assess cancer cells for a mutant version of a p53 polypeptide or polypeptide detection techniques such as immunohistochemistry or ELISAs can be used to assess cancer cells for a mutant version of a p53 polypeptide.

As described herein, cancers that express a mutant version of a p53 polypeptide can be treated by decreasing the level of USP10 polypeptide expression or activity. The decreased level of USP10 polypeptide expression or activity can destabilize mutant p53 polypeptides within the cancer cells, thereby resulting in reduced cancer cell proliferation and increased cancer cell apoptosis. In some cases, the level of USP10 polypeptide expression or activity within cancer cells can be decreased by administering a USP10 polypeptide antagonist to the cancer cells. Examples of USP10 polypeptide antagonists that can have the ability to decrease or inhibit the level of USP10 polypeptide activity within a cell include, without limitation, N-ethylmaleimide, Z-phe-ala fluoromethyl ketone, chymostatin, E-64 (trans-Epoxysuccinyl-L-leucylamido (4-guanidino)butane, E-64d ((2S, 3S)-trans-Epoxysuccinyl-L-leuclamido-3-methylbutane ethyl ester), antipain dihydrochloride, cystatin, and cyano-indenopyrazine derivatives. In some cases, a USP10 polypeptide antagonist can be a nucleic acid molecule designed to induce RNA interference (e.g., an RNAi molecule or a shRNA molecule). Examples of such shRNA molecules include, without limitation, those set forth in FIG. 11. Nucleic acid molecules designed to induce RNA interference against USP10 polypeptide expression can be administered to a mammal using any appropriate method including, without limitation, those methods described herein. For example, a nucleic acid designed to induce RNA interference against USP10 polypeptide expression can be administered to a mammal using a vector such as a viral vector.

In some cases, a USP10 polypeptide inhibitor such as a G3BP1 polypeptide (also known as a RasGap Sh3 domain Binding Protein 1) can be used to decrease or inhibit the level of USP10 polypeptide activity within a cell. Examples of G3BP1 polypeptides include, without limitation, human G3BP1 polypeptides (e.g., a human G3BP1 polypeptide encoded by the nucleic acid sequence set forth in GenBank® Accession Nos. NM_005754.2 (GI No. 38327550) or NM_198395.1 (GI No. 38327551), rat G3BP1 polypeptides (e.g., a rat G3BP1 polypeptide encoded by the nucleic acid sequence set forth in GenBank® Accession Nos. NM_133565.1 (GI No. 281306780), and mouse G3BP1 polypeptides (e.g., a mouse G3BP1 polypeptide encoded by the nucleic acid sequence set forth in GenBank® Accession Nos. NM_013716.2 (GI No. 118130851).

In some cases, an USP10 polypeptide antagonist can be a non-polypeptide molecule (e.g., a nucleic acid-based molecule such as an shRNA or RNAi molecule). In some cases, an USP10 polypeptide antagonist can be a non-G3BP1 polypeptide molecule (e.g., a nucleic acid-based molecule such as an shRNA or RNAi molecule).

This document also provides methods and materials related to identifying agonists or antagonists of USP10 polypeptide mediated stabilization of p53 polypeptides. For example, this document provides methods and materials for using USP10 polypeptides and p53 polypeptides (e.g., ubiquinated p53 polypeptides) to identify agents that increase or decrease the ability of the USP10 polypeptides to stabilize the p53 polypeptides. In some cases, the stability of ubiquinated p53 polypeptides treated with USP10 polypeptides in the presence and absence of a test agent can be assessed to determine whether or not the test agent increases or decreases the stability of the ubiquinated p53 polypeptides. An agent that increases the stability of the ubiquinated p53 polypeptides in a manner dependent on the USP10 polypeptide can be an agonist of USP10 polypeptide mediated stabilization of p53 polypeptides, and an agent that decreases the stability of the ubiquinated p53 polypeptides in a manner dependent on the USP10 polypeptide can be an antagonist of USP10 polypeptide mediated stabilization of p53 polypeptides. The stability of ubiquinated p53 polypeptides can be assessed using polypeptide assays capable of detecting intact full-length polypeptide or degraded polypeptides. USP10 polypeptide agonists and antagonists can be identified by screening test agents (e.g., from synthetic compound libraries and/or natural product libraries). Test agents can be obtained from any commercial source and can be chemically synthesized using methods that are known to those of skill in the art. Test agents can be screened and characterized using in vitro cell-based assays, cell free assays, and/or in vivo animal models.

USP10 agonists or antagonists can be identified using an in vitro screen that includes using purified His-tagged USP10 polypeptide together with ubiquitin-AMC (BIOMOL) as the substrate. Ubiquitin-AMC is a fluorogenic substrate for a wide range of deubiquitinylating enzymes (Dang et al., Biochemistry, 37:1868 (1998)). This fluorescence can allow high-throughput screen of USP10 agonists and antagonists in vitro.

In some cases, the expression level of USP10 polypeptides can be used to assess the p53 genotype of a cancer cell. For example, identification of cancer cells having an increased level of USP10 polypeptide expression can indicate that the cancer cells contain mutant p53, while identification of cancer cells having a decreased level of USP10 polypeptide expression can indicate that the cancer cells contain wild-type p53.

The invention will be further described in the following examples, which do not limit the scope of the invention described in the claims.

EXAMPLES

Example 1

USP10 Regulates p53 Localization and Stability by Deubiquitinating p53

Cell Culture, Plasmids, and Antibodies

H1299, HCT116 p53$^{+/+}$, HCT116 p53$^{-/-}$, U2OS, and HEK293 cells were cultured in RPMI supplemented with 10% FBS. Caki-1 and Caki-2 cells were cultured in McCoy's 5A supplemented with 10% FBS. A-498 cells was cultured in MEM supplemented with 10% FBS. 786-O and 769-P cells were cultured in DMEM supplemented with 10% FBS. ATM$^{+/+}$ and ATM$^{-/-}$ MEFs were culture in DMEM supplemented with 15% FBS.

USP10 was cloned into the p3xFLAG-CMV vector (Sigma) and the pET-28a vector (Novagen). Mdm2 was cloned into the pCMV-HA vector (Clontech). p53 was cloned into the pCMV-Myc vector (Clontech). pBABE-S/FLAG/SBP (streptavidin binding peptide)-tagged USP10 was constructed using Invitrogen's Gateway System. pcDNA3-FLAG-p53 (Addgene plasmid 10838, provided by Dr. T. Roberts) (Gjoerup et al., J. Virol., 75:9142-9155 (2001)), GFP-p53 (Addgene plasmid 12091, provided by Dr. T. Jacks) (Boyd et al., Nat. Cell Biol., 2:563-568 (2000)), GST-p53 (Addgene plasmid 10852, provided by Dr. P M Howley) (Huibregtse et al., Embo J., 10:4129-4135 (1991)), p21 promoter A (Addgene plasmid 16462, provided by Dr. B. Vogelstein) (el-Deiry et al., Cancer Res., 55:2910-2919 (1995)) and pCI-neo Flag HAUSP (Addgene plasmid 16655, provided by Dr. B. Vogelstein) (Cummins and Vogelstein, Cell Cycle, 3:689-692 (2004)) were obtained from Addgene. Deletion mutants were generated by site-directed mutagenesis (Stratagene).

Rabbit anti-USP10 antibodies were raised by immunizing rabbits with GST-USP10 (amino acids 1-200). The antisera were affinity-purified with AminoLink Plus immobilization and purification kit (Pierce). Anti-FLAG (m2) and anti-HA antibodies were purchased from Sigma. Anti-p53 (DO-1) antibodies were purchased from SantaCruz. Anti-MDM2 monoclonal antibody was purchased from Calbiochem.

RNA Interference

USP10 shRNAs having the sequences set forth in SEQ ID NOs: 7 and 8 were purchased from Openbiosystems (RHS4533-NM_005153). Lentivirus USP10 shRNAs were made using a commercially available protocol provided by OpenBiosystems as described elsewhere (Moffat et al., Cell, 124:1283-1298 (2006); Stewart et al., RNA, 9:493-501 (2003); Zufferey et al., Nat. Biotechnol., 15:871-85 (1997); Zufferey et al., J. Virol., 72:9873-80 (1998); and Yamamoto and Tsunetsugu-Yokota, Curr. Gene Ther., 8(1):1-8 (2008)). Briefly, 293T cells (80% confluency) were transfected with the pLKO.1 vector (3 μg) together with packaging plasmid (1.5 μg) and envelope plasmid (1.5 μg) using lipofectamine 2000. Media were changed after 20 hour (RPMI media with 30% FBS). Supernatants containing viruses were collected an additional 24 hours and 48 hours later and filleted (0.45 μm low-protein binding filter). Cells were infected with virus in the presence of 8 μg/mL polybrene.

Co-Immunoprecipitation Assay

Cells were lysed with NETN buffer (20 mM Tris-HCl, pH 8.0, 100 mM NaCl, 1 mM EDTA, 0.5% Nonidet P-40) containing 50 mM β-glycerophosphate, 10 mM NaF, and 1 mg/mL each of pepstatin A, and aprotinin. Whole cell lysates obtained by centrifugation were incubated with 2 μg of antibody and protein A or protein G Sepharose beads (Amersham Biosciences) for 2 hours at 4° C. The immunocomplexes were then washed with NETN buffer three times and separated by SDS-PAGE. Immunoblotting was performed following standard procedures.

GST Pull-Downs

GST fusion proteins were prepared following a standard protocol as described elsewhere (Einarson and Orlinick, Identification of Protein-Protein Interactions with Glutathione S-Transferase Fusion Proteins. In Protein-Protein Interactions: A Molecular Cloning Manual, Cold Spring Harbor Laboratory Press, pp. 37-57 (2002); Einarson, Detection of Protein-Protein Interactions Using the GST Fusion Protein Pulldown Technique. In Molecular Cloning: A Laboratory Manual, 3rd Edition, Cold Spring Harbor Laboratory Press, pp. 18.55-18.59 (2001); and Vikis and Guan, Glutathione-S-Transferase-Fusion Based Assays for Studying Protein-Protein Interactions. In Protein-Protein Interactions, Methods and Applications, Methods in Molecular Biology, 261, Fu, H. Ed. Humana Press, Totowa, N.J., pp. 175-186 (2004)). For in vitro binding assays, p53 GST fusion proteins bound to the GSH Sepharose were incubated with cell lysates. After washing, the bound proteins were separated by SDS-PAGE and immunoblotted with the indicated antibodies.

Protein Stability Assay

Cycloheximide was purchased from Sigma. For protein turnover analysis, cycloheximide was added to cell culture medium at the final concentration of 0.1 mg/mL, and cells were harvested at the indicated time points. Cells were then lysed, and cell lysates were resolved by SDS-PAGE and analyzed by Western blot.

Ubiquitination of p53 In Vivo and In Vitro

The ubiquitination levels of p53 were detected essentially as described elsewhere (Li et al., Nature, 416:648-653 (2002)). For the in vivo deubiquitination assay, H1299 cells were transfected with FLAG-p53 or in combination with different expression vectors as indicated. After 48 hours, cells were treated for 4 hour with a proteasome inhibitor MG132 (50 μM) before being harvested. The cell extracts were subjected to immunoprecipitation with anti-FLAG antibody and blotted with anti-p53 antibodies.

For the preparation of a large amount of ubiquitinated p53 as the substrate for the deubiquitination assay in vitro, HEK293 cells were transfected together with the FLAG-p53, pCMV-Mdm2, and HA-UB expression vectors. After treatment as described above, ubiquitinated p53 was purified from the cell extracts with anti-FLAG-affinity column in FLAG-lysis buffer (50 mM Tris-HCl pH 7.8, 137 mM NaCl, 10 mM NaF, 1 mM EDTA, 1% Triton X-100, 0.2% Sarkosyl, 1 mM DTT, 10% glycerol and fresh proteinase inhibitors). After extensive washing with the FLAG-lysis buffer, the proteins were eluted with FLAG-peptides (Sigma). The recombinant His-USP10 and USP10CA were expressed in BL21 cells and purified on the His-tag purification column (Novagen). For the deubiquitination assay in vitro, ubiquitinated p53 protein was incubated with recombinant USP10 in a deubiquitination buffer (50 mM Tris-HCl pH 8.0, 50 mM NaCl, 1 mM EDTA, 10 mM DTT, 5% glycerol) for 2 hours at 37° C.

Cell Fractionation

H1299 cells were transfected with the indicated constructs. Forty-eight hours later, cells were treated for 4 hours with a proteasome inhibitor, MG132 (50 µM) before being harvested. Cytoplasmic and unclear fractions were separated by using Paris Kit (Ambion).

Immunofluorescence

For the p53 translocation assay, H1299 cells were plated on glass coverslips and transfected with the indicated plasmid. Forty-eight hours after transfection, 50 µM of proteasome inhibitors (MG132) was added for 4 hours before fixation. Cells were then fixed in 4% paraformaldehyde for 10 minutes at room temperature and stained using standard protocols.

Luciferase Assay

HCT116 p53$^{+/+}$ and HCT116 p53$^{-/-}$ cells were seeded at $8\times10^4$ cells/well on 24-well plates. The next day, cells were transfected with 200 ng of p21 reporter construct and other indicated plasmids. pRL-TK (50 ng) was included as an internal control. Luciferase assays were carried out according to the manufacturer's instructions (Dual-Luciferase Reporter Assay System; Promega). Results were normalized for expression of pRL-TK as measured by Renilla luciferase activity.

Cell Growth Assay

Cell growth was analyzed using MTS reagent (Promega) according to the manufacturer's directions. HCT116 p53$^{+/+}$ and HCT116 p53$^{-/-}$ cells stably infected with lentivirus encoding control shRNA or USP10 shRNA (1,000 cells/well) were plated on 96-well plates and grown on 10% serum containing media. Cell proliferation was estimated after 1, 2, 3, 4, 8, and 10 days.

Colony and Soft Agar Colony-Formation Assays

The soft agar colony-formation assay was performed as described elsewhere (Shim et al., *Proc. Natl. Acad. Sci. USA*, 94:6658-6663 (1997)). Briefly, cells were infected with lentivirus encoding control, USP10shRNA, or USP10shRNA together with FLAG-tagged USP10. Cells were then plated in 0.3% top agarose in 35 mm dishes and cultured for two weeks. Colonies were counted at room temperature under a light microscope (ECLIPSE 80i; Nikon) using a 4x NA 0.10 objective lens (Nikon). Images were captured with a camera (SPOT 2 Megasample; Diagnostic Instruments) and processed using SPOT 4.6 software (Diagnostic Instruments). Adobe Photoshop and Illustrator were used to generate figures.

Apoptosis Assay

Cells were washed with PBS and fixed in 4% paraformaldehyde at room temperature for 15 minutes. For DAPI staining, cells were stained with 50 µg/mL DAPI. The number of apoptotic cells with nuclear morphology typical of apoptosis was scored in at least 400 cells in each sample by using fluorescence microscopy. The reader was blinded to the actual groups in the fluorescence microscopy.

Tissue Microarray

The tissue array of kidney cancer samples was purchased from US Biomax (KD 2083, KD991t, KD804, KD241, KD208t) Immunohistochemical staining against USP10 (dilution 1:500) was carried out with a IHC Select® HRP/DAB kit (Cat. DAB50, Millipore). The degree of immunostainining was determined by board certified pathologists using a four-tier grading system (0=negative, 1=weak, 2=moderate, and 3=strong staining intensity) in a blinded manner.

Results

USP10 Interacts with p53 and Stabilizes p53

Figure 1B:
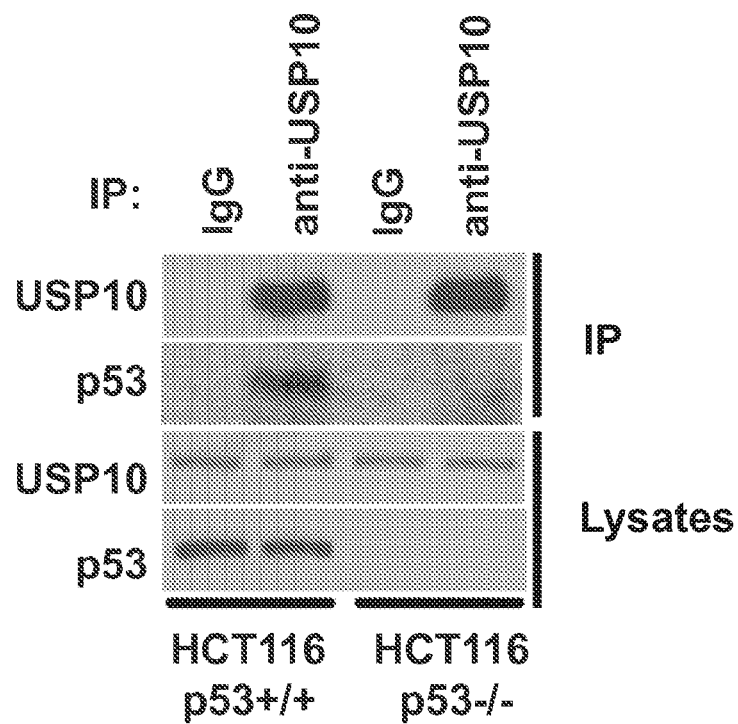
Figure 1C:
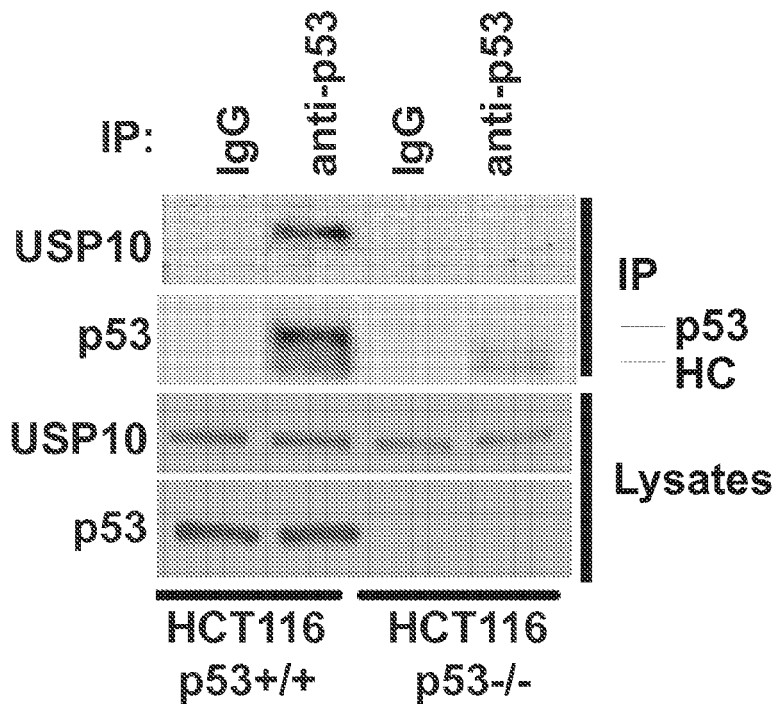
Figure 1D:
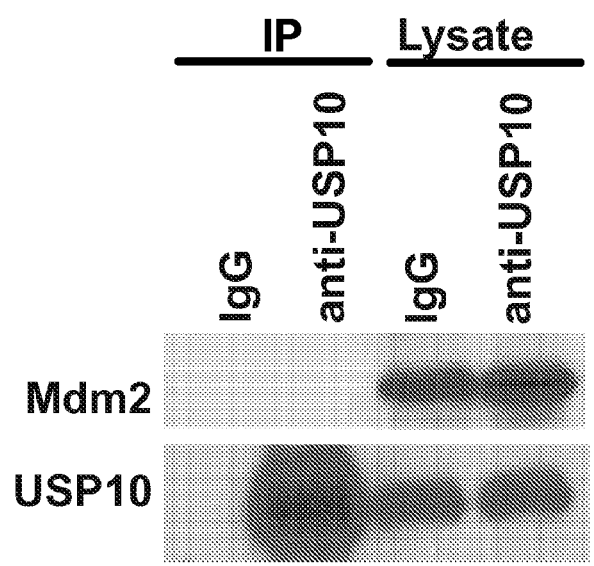
Figure 1E:
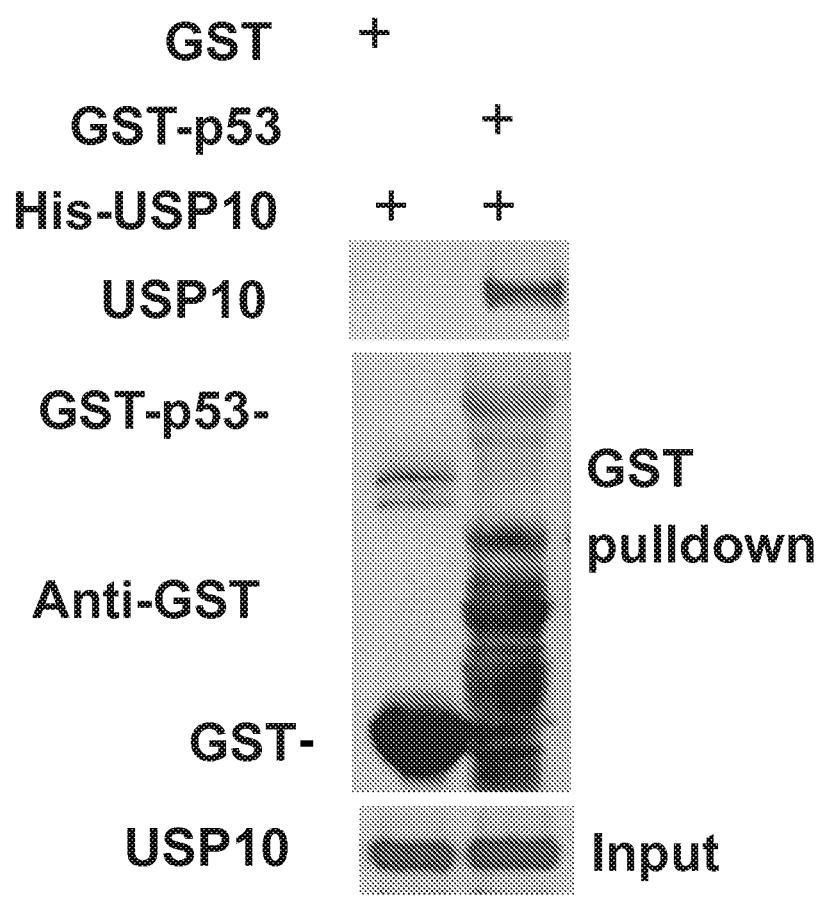
Figure 1F:
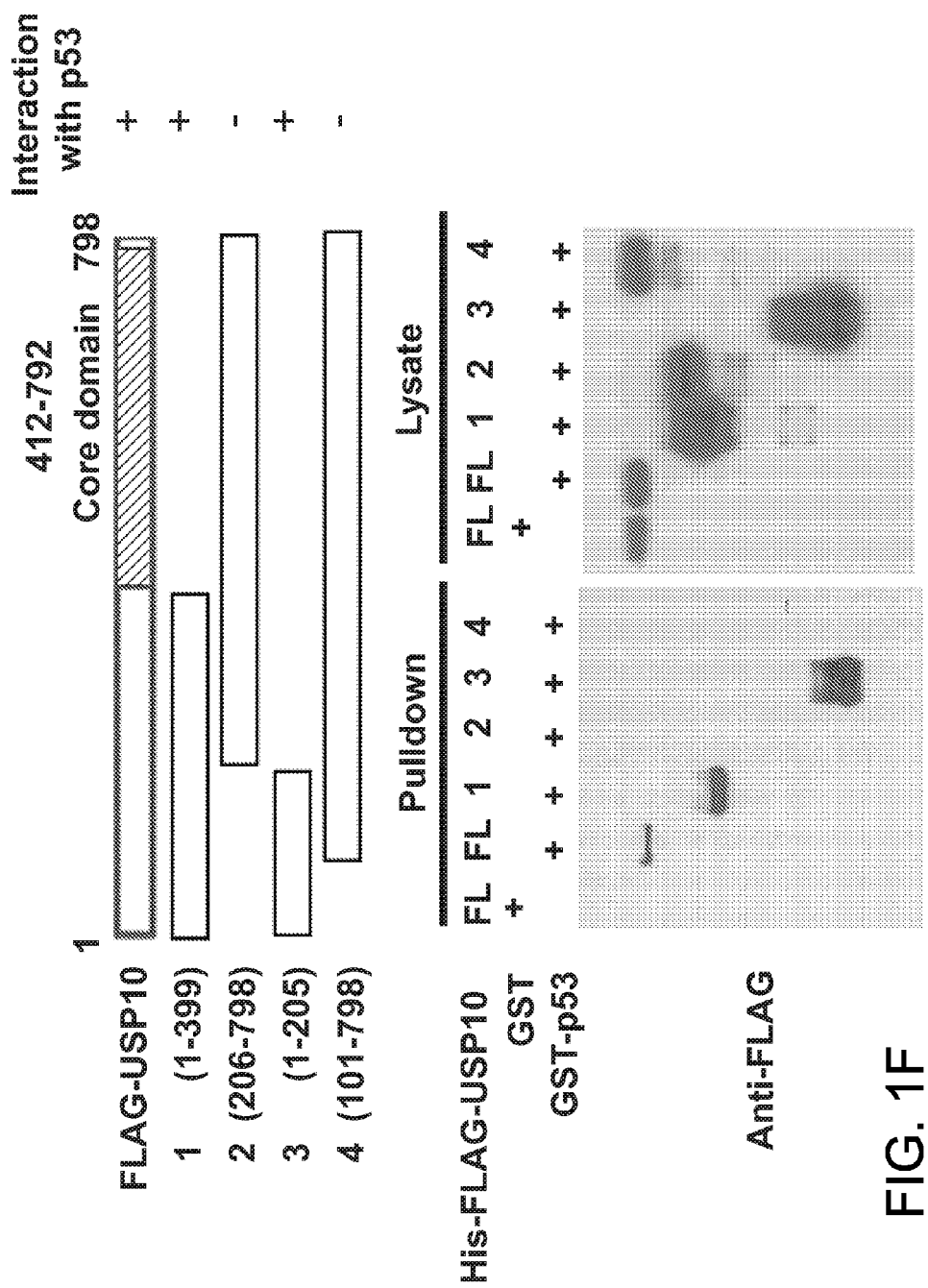

As shown in FIG. 1A-B, USP10 coimmunoprecipitated with p53 in U2OS and HCT116 p53$^{+/+}$ cells, but not HCT116 p53$^{-/-}$ cells. Reciprocal immunoprecipitation with anti-p53 also brought down USP10 in HCT116 p53$^{+/+}$, but not in HCT116 p53$^{-/-}$ cells (FIG. 1C). Unlike HAUSP, USP10 did not interact with Mdm2 (FIG. 1D). These results suggest a specific interaction between USP10 and p53 in vivo. However, it is not clear whether the USP10-p53 interaction is direct. To test this, recombinant USP10 and p53 were generated and purified. Purified USP10 was able to interact with p53 under cell-free conditions, suggesting a direct interaction between USP10 and p53 (FIG. 1E). Further mapping of the USP10-p53 interaction revealed that the N-terminal region (AA1-AA101), but not the enzymatic domain of USP10, is required for the interaction between USP10 and p53 (FIG. 1F).

Figure 2A:
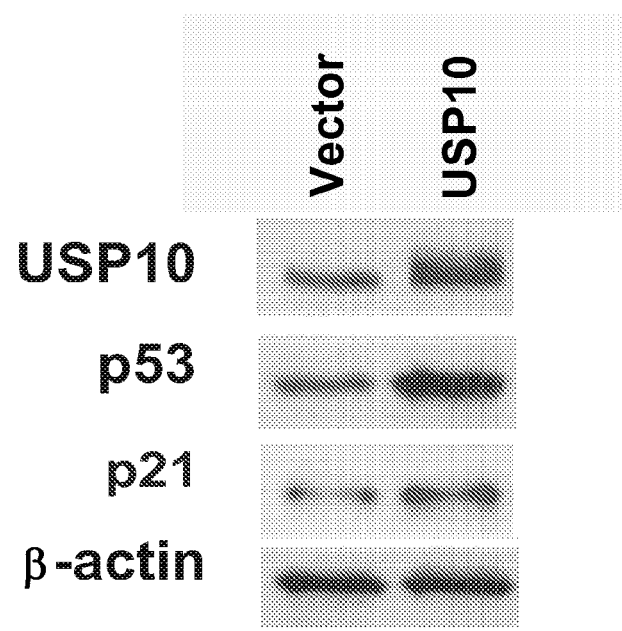
FIG. 2. USP10 stabilizes and deubiquitinates p53. (A) HCT116 cells were transfected with vectors or constructs encoding FLAG-tagged USP10. Forty-eight hours later, cells were lysed, and cell lysates were blotted with indicated antibody. (B) HCT116 cells were infected with lentivirus encoding indicated shRNAs. 72 hours later, cells were lysed, and cell lysates were blotted with indicated antibody. (C) HCT116 cells were stably expressing control shRNA, USP10 shRNA, or USP10 shRNA together with shRNA-resistant USP10. Cells were treated with cycloheximide (0.1 mg/mL) and harvested at the indicated time. The upper panels show immunoblots of p53 and USP10. β-actin was included as a control. Lower panel: quantification of the p53 protein levels relative to β-actin. (D) HCT116 cells were transfected with indicated plasmids. Forty-eight hours later, cells were lysed, and cell lysates were blotted with indicated antibody. (E-G) Regulation of p53 ubiquitination levels in vivo by USP10. H1299 cells transfected with indicated constructs (E) or stably expressing control or USP10 shRNA (F) were transfected with FLAG-p53. Forty-eight hours later, cells were treated with MG132 for 4 hours before harvest. p53 was immunoprecipitated with anti-FLAG antibodies and immunoblotted with anti-p53 antibodies. (G) Deubiquitination of p53 in vitro by USP10. Ubiquitinated p53 was incubated with purified USP10 or USP10CA in vitro and then blotted with anti-p53 antibodies.
Figure 2B:
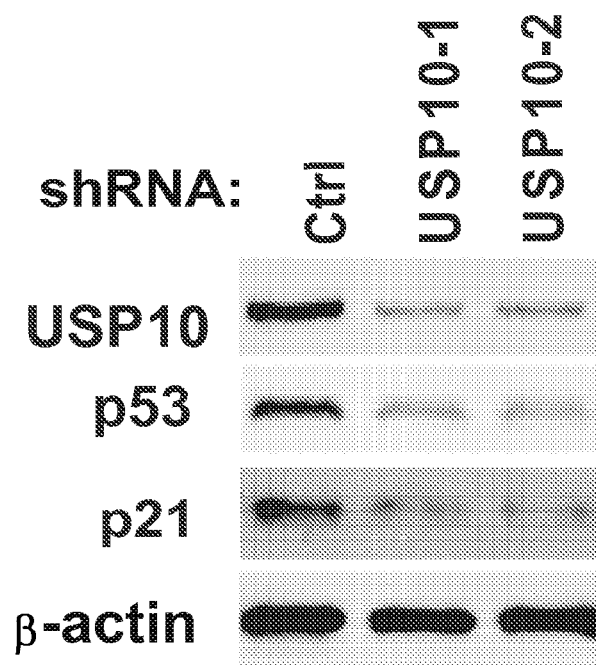
Figure 2C:
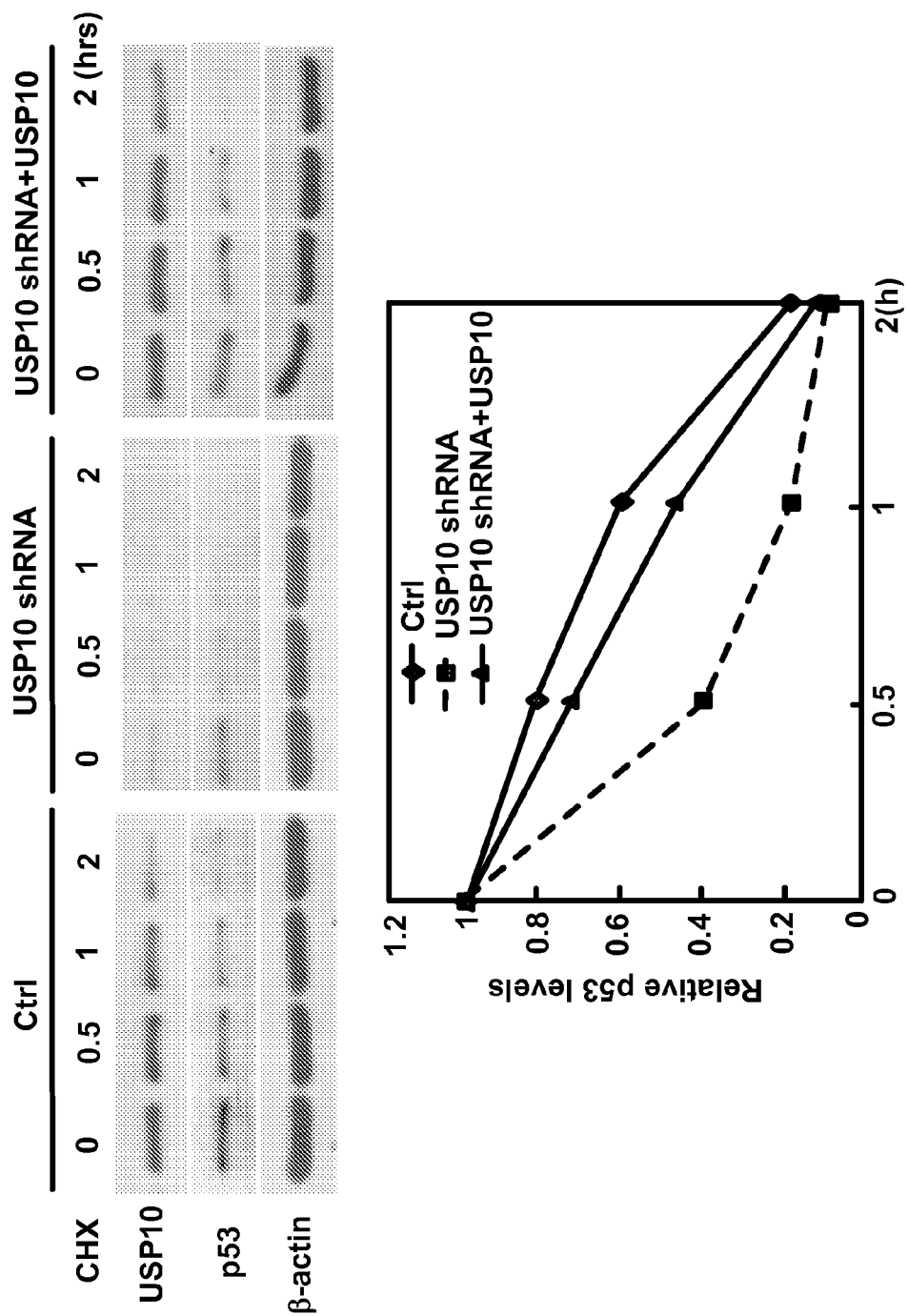

USP10 was overexpressed in cells to determine if USP10 could function to stabilize p53. As shown in FIG. 2A, overexpression of USP10 significantly increased the levels of endogenous p53 and the p53 target p21. To confirm these results, USP10 expression was knocked-down using USP10 specific shRNA. The downregulation of USP10 decreased p53 and p21 levels (FIG. 2B). A second USP10 shRNA also exhibited similar effects (FIG. 2B). These results indicate that USP10 can upregulate p53 levels, most likely by deubiquitinating and consequently stabilizing p53. To further confirm that USP10 affects p53 stability, control cells or cells stably expressing USP10 shRNA were treated with cycloheximide (CHX), and p53 stability was examined. p53 stability was decreased in cells stably expressing USP10 shRNA, while reconstitution with shRNA-resistant USP10 restored p53 stability (FIG. 2C). These results demonstrate that USP10 stabilizes p53 in cells.

USP10 Deubiquitinates p53

Figure 2D:
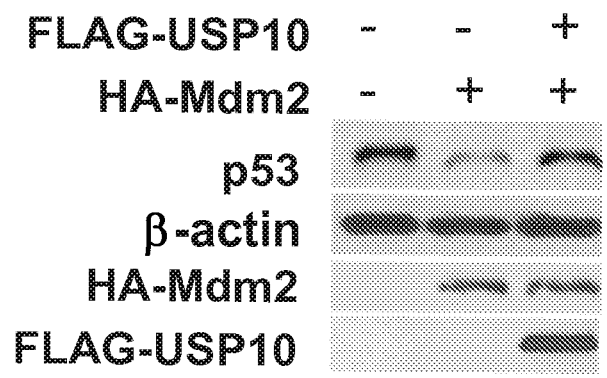
Figure 2E:
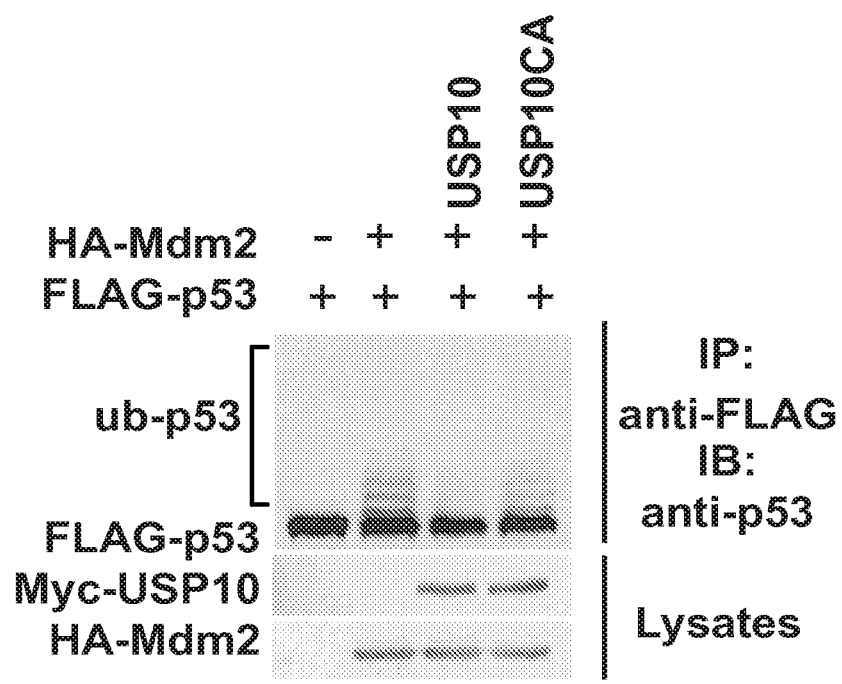
Figure 2F:
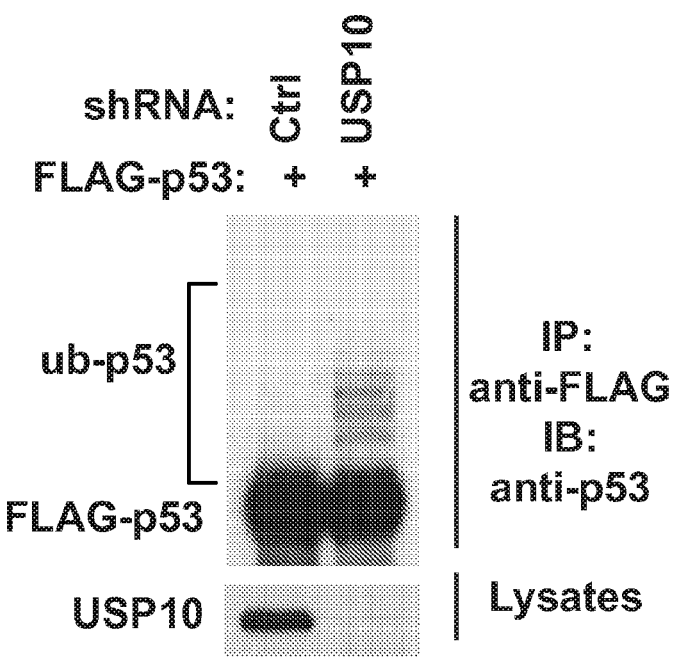
Figure 2G:
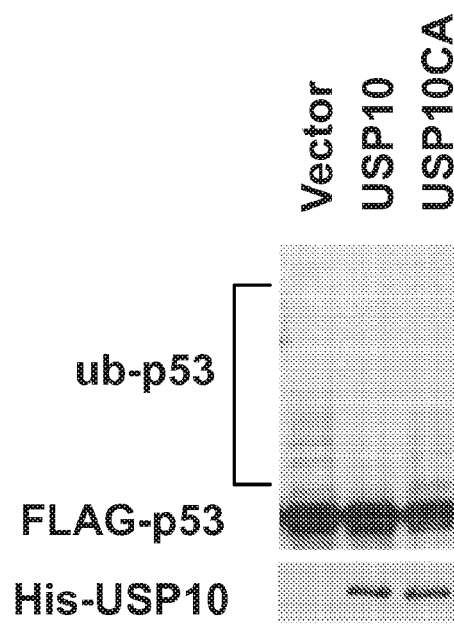

USP10 may function to deubiquitinate p53 to counteract the action of E3 ubiquitin ligases such as Mdm2. Indeed, as shown in FIG. 2D, although overexpression of Mdm2 significantly induced the degradation of p53, coexpression of USP10 effectively rescued p53 from Mdm2-induced degradation. Whether USP10 regulates the levels of p53 ubiquitination in cells was also examined. As shown in FIG. 2E, Mdm2 induced the ubiquitination of p53; however, p53 ubiquitination was significantly diminished by coexpression of USP10. On the other hand, coexpression of USP10-C488A (USP10CA), a catalytic-inactive USP10 mutant containing a mutation at the core enzymatic domain (Soncini et al., *Oncogene*, 20:3869-3879 (2001)), lost the ability to reverse p53 ubiquitination induced by Mdm2 (FIG. 2E). Conversely, downregulation of USP10 increased p53 ubiquitination (FIG. 2F). These results indicate that USP10 negatively regulates p53 ubiquitination induced by Mdm2 in cells. However, from this data alone it is not clear whether USP10's effect on p53 is direct, since it is possible that USP10 affects another protein, which in turn affects p53 ubiquitination. To directly examine the deubiquitination activity of USP10 toward p53, it was determined whether USP10 could deubiquitinate p53 in a cell free system. USP10 and USP10CA were purified from bacteria, and ubiquitinated p53 was purified from cells expressing FLAG-p53, pCMV-Mdm2, and HA-ub. USP10 and ubiquitinated p53 were then incubated in a cell-free system. As shown in FIG. 2G, purified wild-type USP10, but not the catalytically inactive USP10CA, effectively deubiquitinated p53 in vitro. These results demonstrate that USP10 deubiquitinates p53 both in vitro and in vivo.

USP10 Localizes in the Cytoplasm and Counteracts Mdm2 Action

Figure 3A:
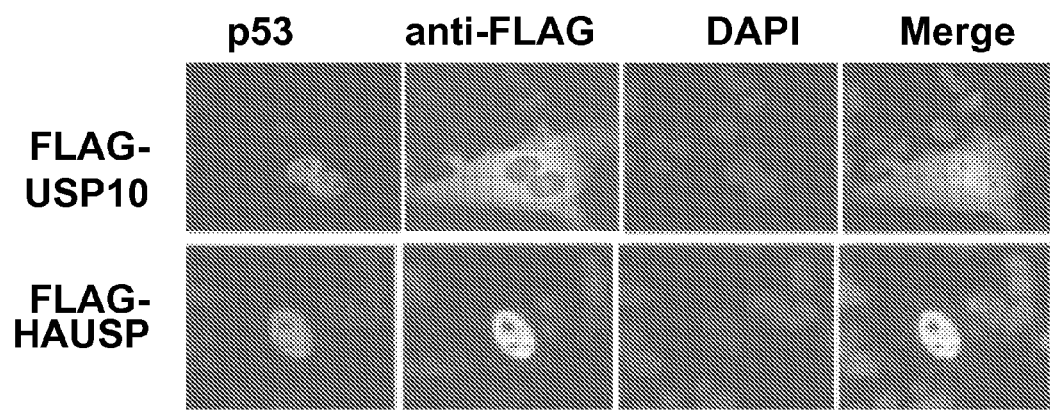
FIG. 3. Regulation of the subcellular localization of p53 by USP10. (A) Subcellular localization of USP10 and a ubiquitin-specific protease, HAUSP. U2OS cells were transfected with constructs encoding FLAG-USP10 or FLAG-HAUSP. Forty-eight hours later, cells were fixed and stained with indicated antibodies and DAPI. (B) H1299 cells were cotransfected with indicated constructs. Forty-eight hours later, cells were treated with MG132, harvested, and fractionated as described herein. Cellular fractions were then blotted with indicated antibodies. (C, cytoplasmic; N, nuclear). A cytoplasmic marker protein (GAPDH) and a nuclear marker protein (Histone3) were used as controls to confirm the quality of fractionations. (C) H1299 cells were transfected with indicated constructs. Forty-eight hours later, the cells were treated with MG132, fixed, and stained with the indicated antibodies and DAPI. (D) U2OS cells were infected with lentivirus encoding control shRNA or USP10 shRNA. 72 hours later, cells were treated with MG132, fixed, and stained with the indicated antibodies or DAPI. (C-D) Right panels: Quantification of cells with different p53 subcellular localization. Nuc: Nucleus only; Cyto+Nuc: both cytoplasm and nucleus. The data represent the average of three experiments, and 150 cells were monitored in each experiment.
Figure 3B:
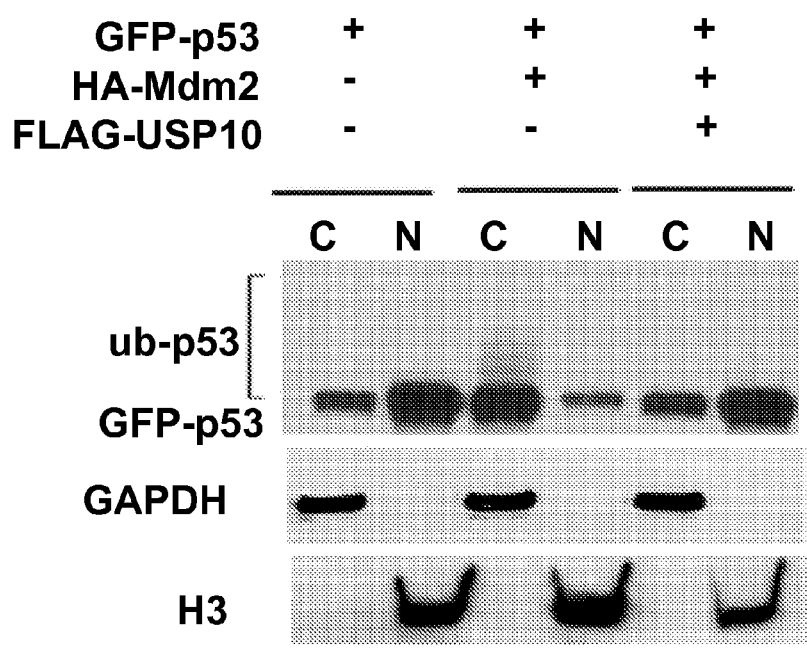
Figure 3C:
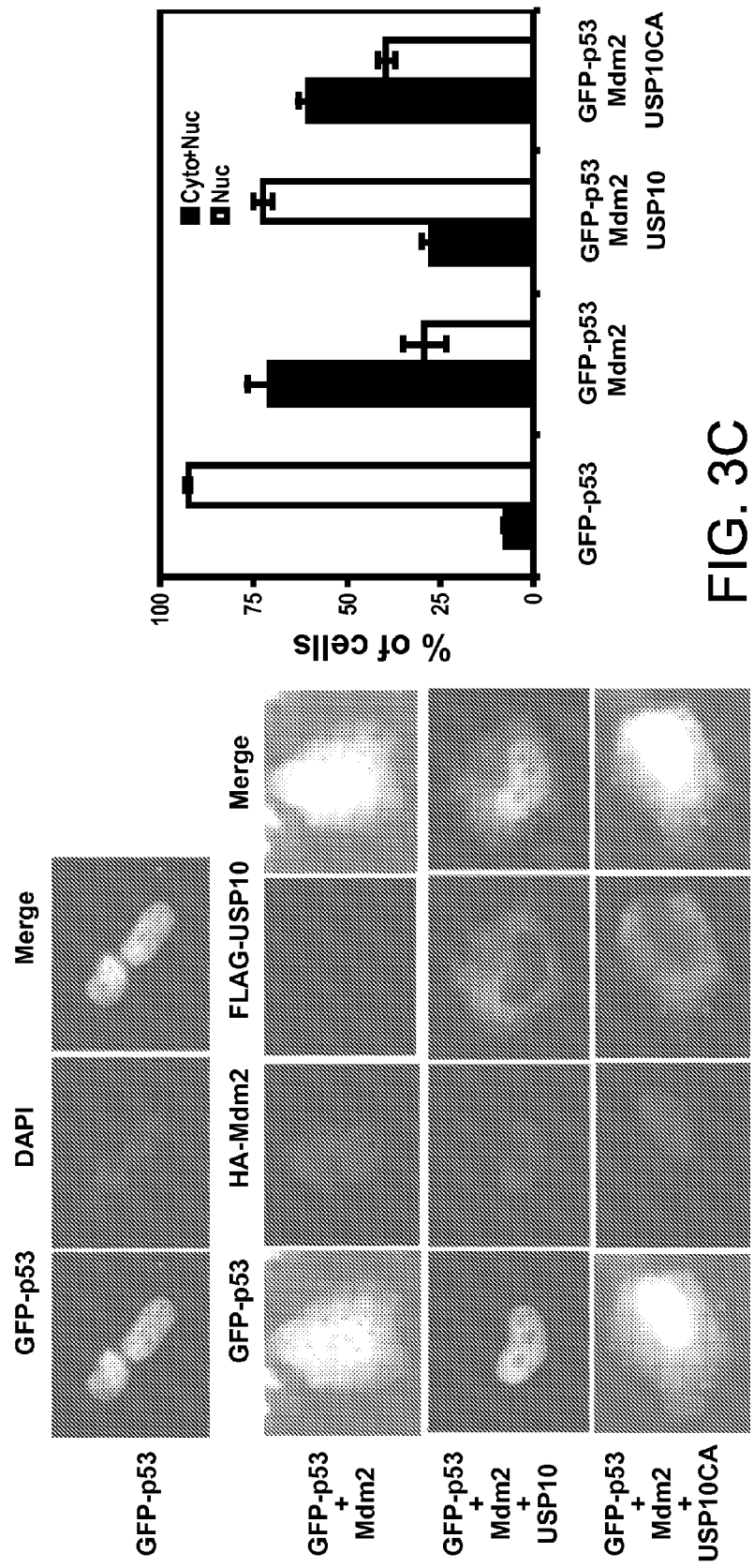
Figure 3D:
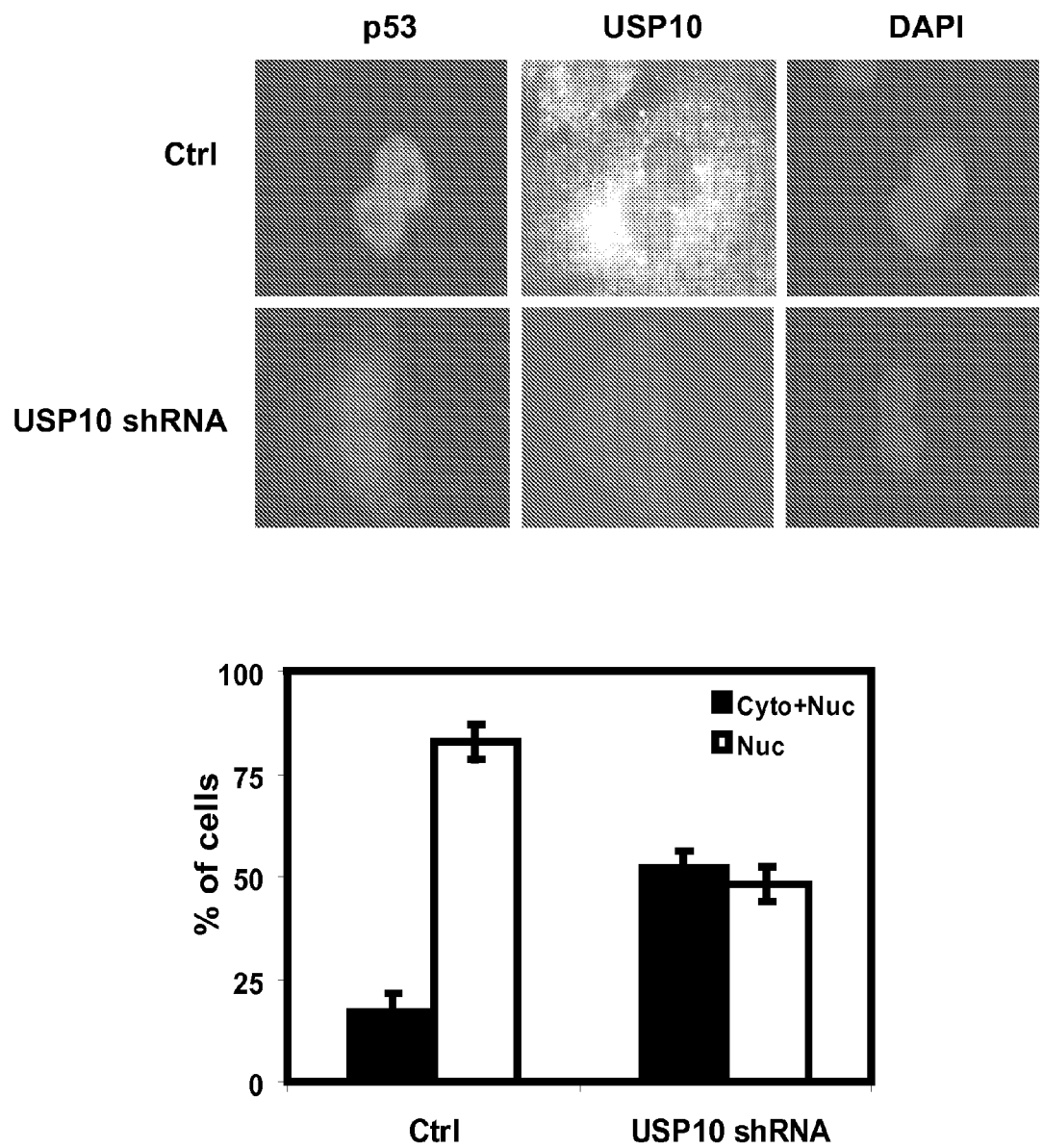
Figure 8A:
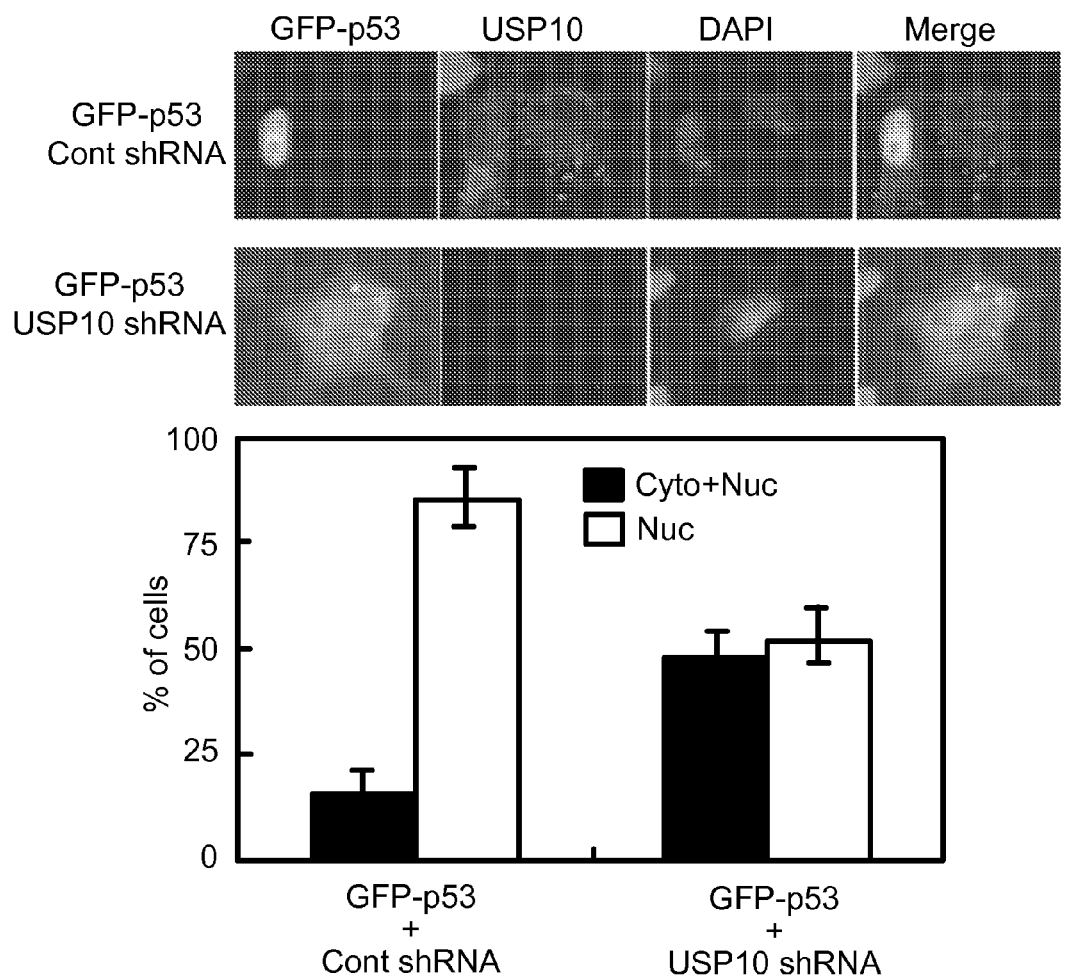
FIG. 8. (A) H1299 cells stably transfected with control or USP10 shRNA were transfected with GFP-p53. Forty-eight hours later, the cells were treated with MG132, fixed, and stained with the indicated antibodies and DAPI. Right panels: Quantification of cells with different p53 subcellular localization. Nuc: Nucleus only; Cyto+nuc: both cytoplasm and nucleus. The data represent the average of three experiments, and 150 cells were monitored in each experiment. (B) Cells the same as FIG. 6H were left untreated or treated with 10 Gy radiation. After four hours, the cells were fixed and stained with anti-FLAG antibody or DAPI. Right panels: Quantification of cells with different USP10 subcellular localization. Cyto: cytoplasm only; Cyto+Nuc: cytoplasm and nucleus. The data represent the average of three experiments, and 150 cells were monitored in each experiment. (C) Cells the same as FIG. 7D-E were lysed, and cell lysates were blotted with the indicated antibodies.

Previous studies suggest that ubiquitination of p53 by Mdm2 could induce p53 translocation from nucleus to cytoplasm (Boyd et al., Nat. Cell. Biol., 2:563-568 (2000); Geyer et al., Nat. Cell. Biol., 2:569-573 (2000); Li et al., Science, 302:1972-1975 (2003); and Stommel et al., Embo J., 18:1660-1672 (1999)). In addition, the cytoplasmic ubiquitin ligase Parc can ubiquitinate p53 and trap p53 in the cytoplasm (Nikolaev et al., Cell, 112:29-40 (2003). However, it is not clear whether the cytoplasmic p53 can be deubiquitinated and returned to the nucleus, since HAUSP is mainly localized in the nucleus and no cytoplasmic ubiquitin-specific protease against p53 has been identified. Unlike HAUSP, USP10 is predominantly localized to the cytoplasm (FIG. 3A). This result suggests that USP10 is the cytoplasmic deubiquitinase for p53. Thus, it is possible that USP10 could reverse Mdm2-induced nuclear export of p53. To test this, cell fractionation experiments were performed. Expression of Mdm2 was found to induce ubiquitination and nuclear export of p53, which was reversed by USP10 coexpression (FIG. 3B). To confirm this result, immunofluorescence assays were performed to detect the subcellular localization of p53. When H1299 cells were transfected with GFP-tagged p53, GFP-p53 was readily detected in the nucleus. As previously demonstrated, when cells were cotransfected with Mdm2, Mdm2 induced cytoplasmic translocation of p53 (Boyd et al., Nat. Cell. Biol., 2:563-568 (2000); Geyer et al., Nat. Cell. Biol., 2:569-573 (2000); Li et al., Science, 302:1972-1975 (2003); and Stommel et al., Embo J., 18:1660-1672 (1999)). However, coexpression of wild-type USP10, but not catalytically inactive USP10 (USP10CA), reversed Mdm2-induced cytoplasmic translocation of p53 (FIG. 3C). These results demonstrate that USP10 counteracts Mdm2 by deubiquitinating p53 and inducing p53 translocation from the cytoplasm back to the nucleus. Therefore, a balance between USP10 and Mdm2 could determine p53 localization. If so, downregulation of USP10 could have a similar effect as Mdm2 overexpression. Consistent with this finding, downregulation of USP10 itself induced nuclear export of endogenous p53 (FIG. 3D). Similar results were obtained using GFP-p53 (FIG. 8A). These results support a role of USP10 in regulating homeostasis of p53 in cells.

USP10 Regulates p53 Function

Figure 4A:
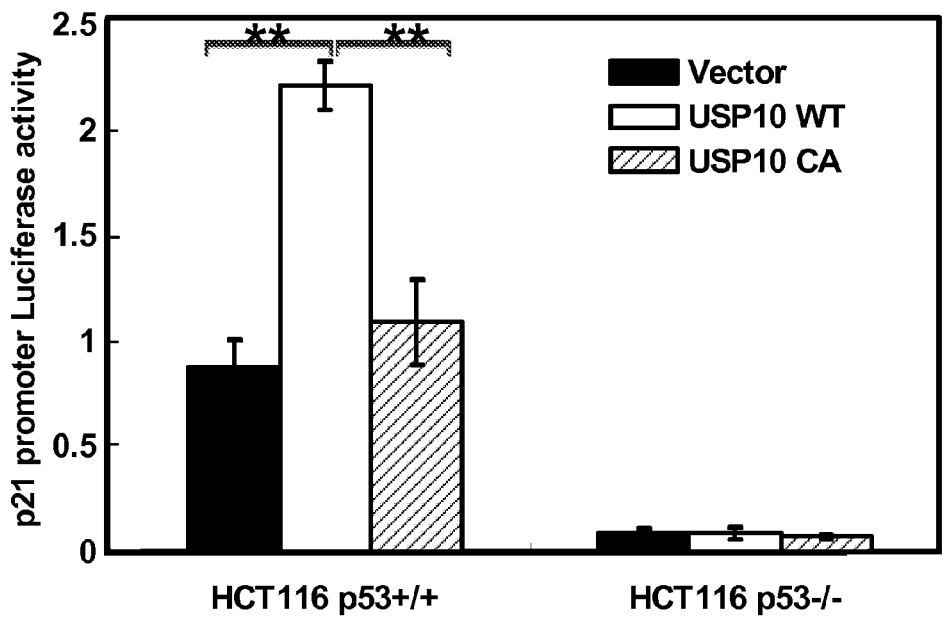
FIG. 4. Effects of USP10 on p53-mediated transcriptional activity, cell growth repression, and apoptosis. (A) p53 reporter constructs for the p21 promoter were cotransfected with indicated constructs into HCT116 p53$^{+/+}$ and HCT116 p53$^{-/-}$ cells. Reporter activity was then determined as described herein. (B) p53 reporter assay was performed in HCT116 p53$^{+/-}$ and HCT116 p53$^{-/-}$ cells stably expressing control shRNA or USP10 shRNA. (C) H1299 cells were transfected with the indicated constructs. Forty-eight hours later, apoptotic cells were determined as described herein. (D) HCT116 p53$^{-/+}$ and HCT116 p53$^{-/-}$ cells stably expressing control shRNA or USP10 shRNA were plated, and cell proliferation was then quantified at the indicated time. (E) Soft agar colony-formation assay was performed using HCT116 p53$^{+/+}$ and HCT116 p53$^{-/-}$ cells stably expressing control shRNA, USP10 shRNA, or USP10 shRNA together with shRNA-resistant USP10. Right panel: quantification of colonies formed in soft agar. Bars, 400 μm. (A-E). Error bar represents the mean±SEM of triplicate experiments. ** represents P<0.01 two tailed student's t test.
Figure 4B:
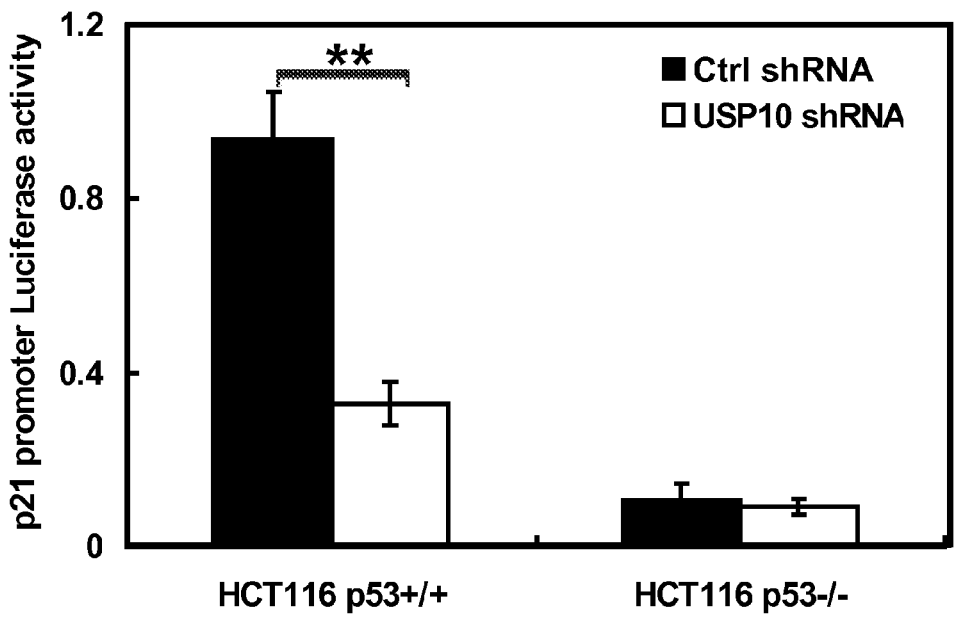
Figure 4C:
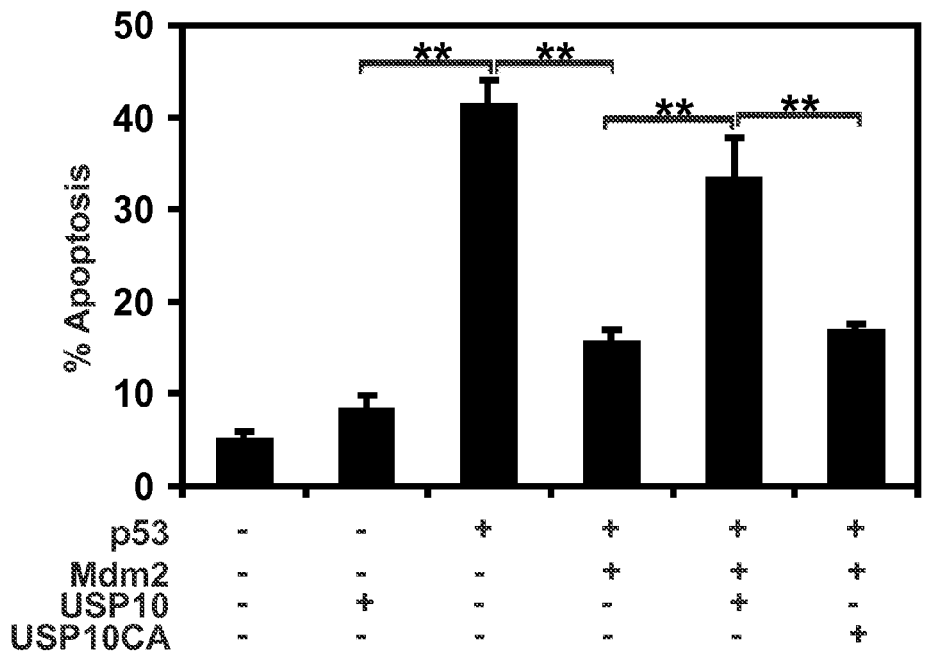
Figure 4D:
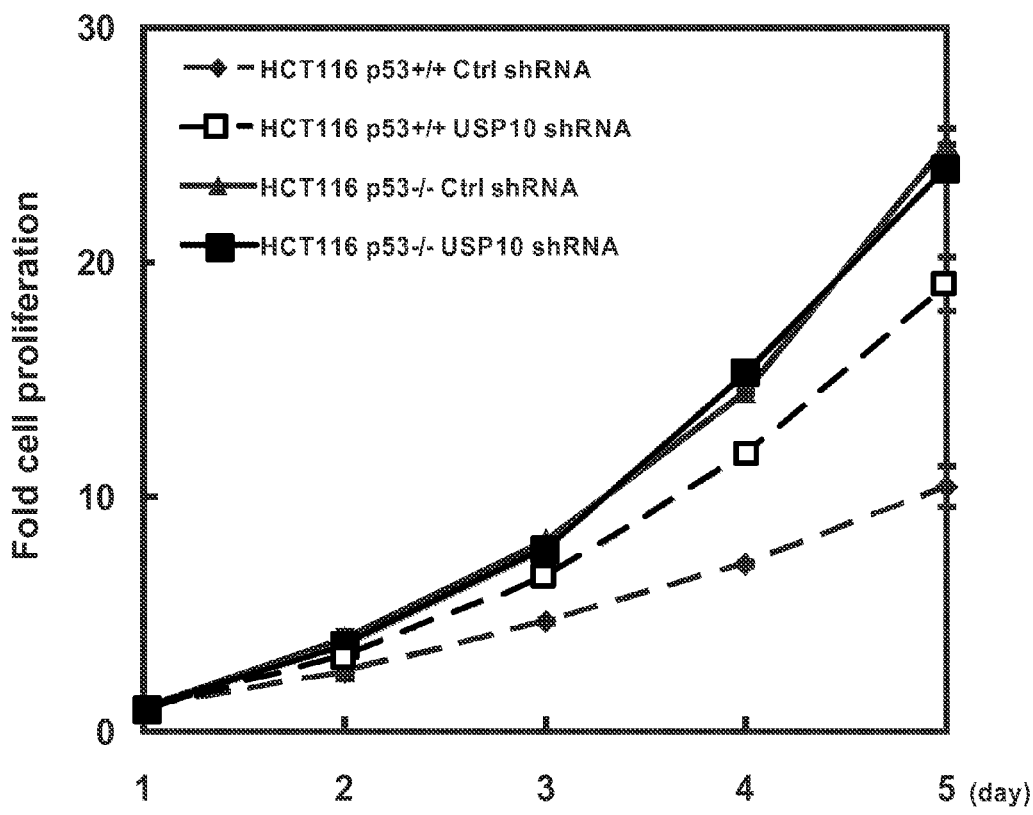
Figure 4E:
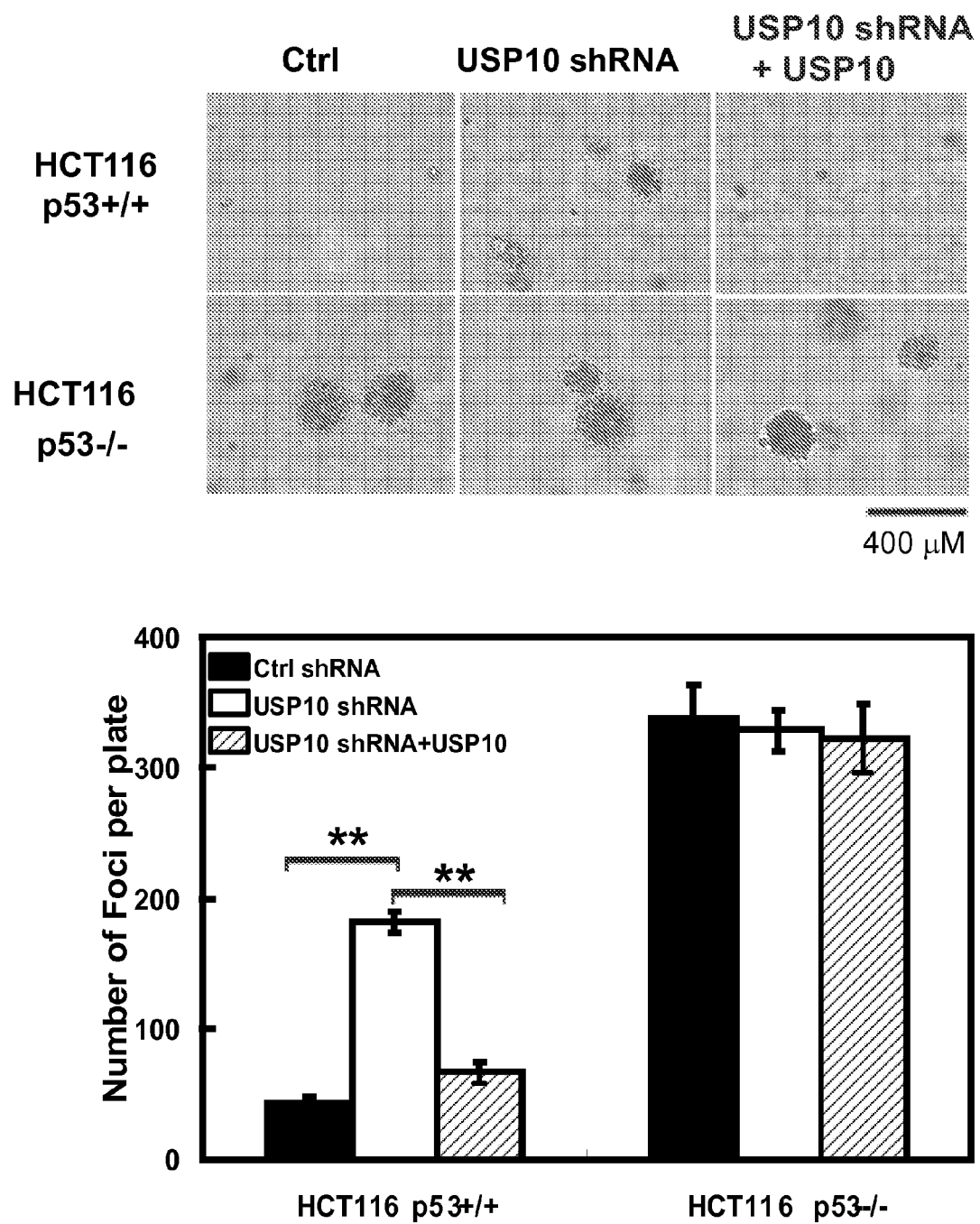

USP10's effects on p53 stabilization and nuclear import raised the possibility that USP10 regulates p53-dependent transcriptional activity, cell transformation, and apoptosis. As shown in FIG. 4A, overexpression of wild-type USP10, but not catalytically inactive USP10 (USP10CA), increased p21 promoter activity in HCT116 p53$^{+/+}$ cells, but not in HCT116 p53$^{-/-}$ cells. Conversely, stable knockdown of USP10 by shRNA inhibited p21 promoter activity in HCT116 p53$^{+/+}$ cells, but had little effect in HCT116 p53$^{-/-}$ cells (FIG. 4B). These results demonstrate that USP10 regulates p53-dependent transcription activity. Furthermore, experiments were performed to test whether USP10 directly affects p53-dependent apoptosis. As shown in FIG. 4C, overexpression of p53 induced apoptosis, while Mdm2 strongly reduced p53-dependent apoptosis. However, coexpression of USP10, but not catalytically inactive USP10, significantly reversed the inhibitory effect of Mdm2 on p53-mediated apoptosis. How USP10 affects cell proliferation was also investigated. As shown in FIG. 4D, downregulation of USP10 increased cancer cell proliferation in p53$^{+/+}$ cells, but not p53$^{-/-}$ cells. A similar effect was observed when cancer cells were culture in soft agar (FIG. 4E). On the other hand, reconstitution of USP10 in cells with USP10 downregulation inhibited cancer cell proliferation (FIG. 4E), suggesting the effect of USP10 knockdown is specific. Overall, these results demonstrate that USP10 potentiates p53 function in cells.

Figure 5A:
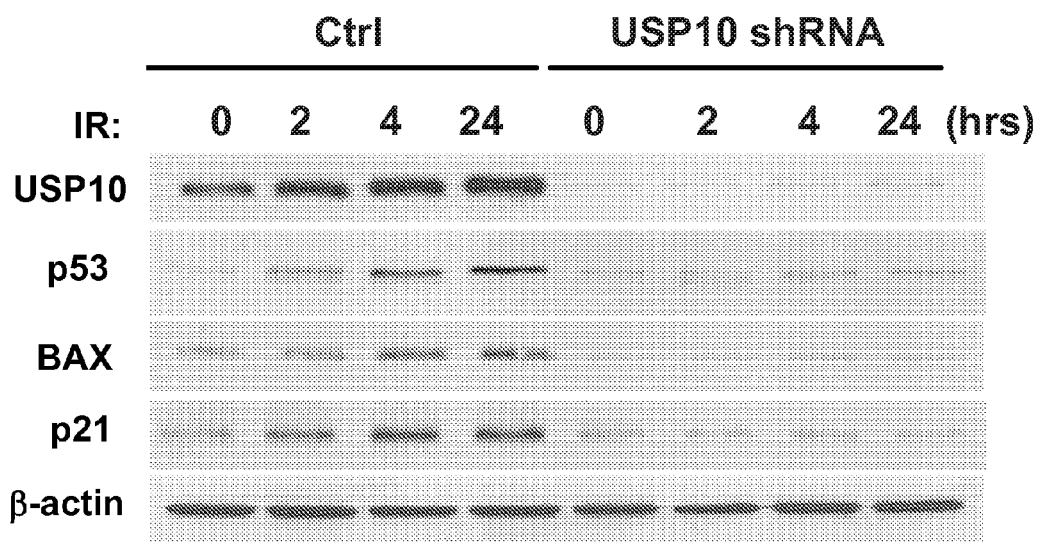
FIG. 5. USP10 translocates into the nucleus and regulates p53 activity following DNA damage. (A) HCT116 cells stably expressing control shRNA or USP10 shRNA were irradiated (10 Gy), and cells were harvested at the indicated time. Cell lysates were then blotted with the indicated antibodies. (B) HCT116 cells were left untreated or treated with 10 Gy radiation. Four hours later cells were stained with anti-USP10 antibody. (C) HCT116 cells were irradiated (10 Gy) or left untreated. After four hours, cells were harvested and fractionated as described herein. Cellular fractions were then blotted with the indicated antibodies. (D) HCT116 p53$^{+/+}$ or p53$^{-/-}$ cells stably expressing control shRNA or USP10 shRNA were left untreated or treated with 10 Gy radiation. After 48 hours, apoptotic cells were determined as described herein. Error bar represents the mean±SEM of triplicate experiments. ** represents P<0.01 two tailed student's t test. (E) The same cells in (D) were treated with 10 Gy radiation, then harvested at the indicated time. Cell cycle progression was examined by FACS.
Figure 5B:
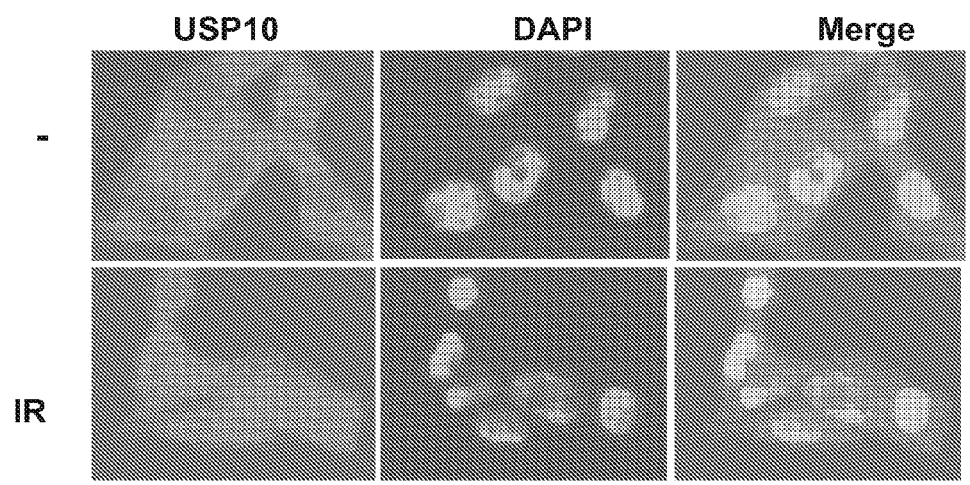
Figure 5C:
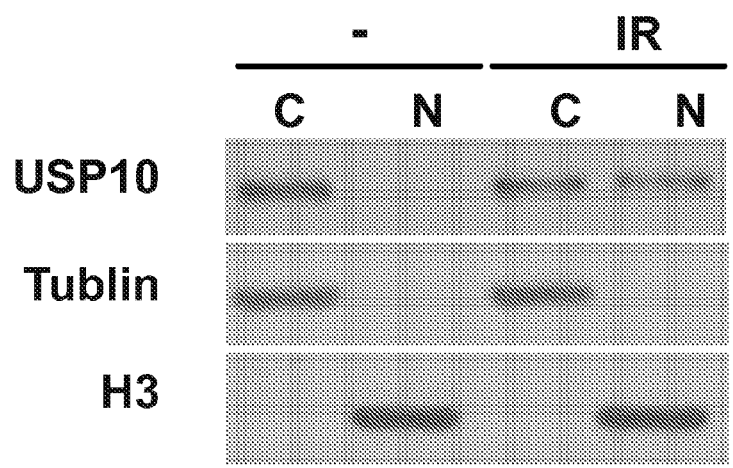

USP10 is Upregulated and Translocates to the Nucleus Following DNA Damage and Regulates p53-Dependent DNA Damage Response The results provided herein reveal that USP10 can regulate p53 homeostasis in unstressed cells. Since p53 plays a role in DNA damage response and becomes stabilized following DNA damage, it was examined whether USP10 is involved in p53 stabilization after DNA damage. Interestingly, downregulation of USP10 significantly decreased p53 stabilization and the expression of p53 target genes p21 and Bax after DNA damage (FIG. 5A), suggesting that USP10 also regulates p53 stabilization after DNA damage. Furthermore, it was observed that the expression of USP10 itself was increased after DNA damage. These results can be rather surprising, since most DNA damage signaling is thought to occur in the nucleus. How does USP10, which is located in the cytoplasm, affect p53 stabilization during DNA damage response? It is possible that p53 is still actively exported out of the nucleus and gets degraded in the cytoplasm during DNA damage response, although there is lack of evidence to support this. Alternatively, USP10 could translocate into the nucleus to participate in DNA damage response. Indeed, USP10 also localized in the nucleus following DNA damage as determined by immunofluorescence (FIG. 5B). To confirm the translocation of USP10, cell fractionation assays were performed. As shown in FIG. 5C, increased amounts of USP10 were detected in the nucleus following DNA damage, confirming a DNA damage-induced translocation of USP10 into the nucleus.

Figure 5D:
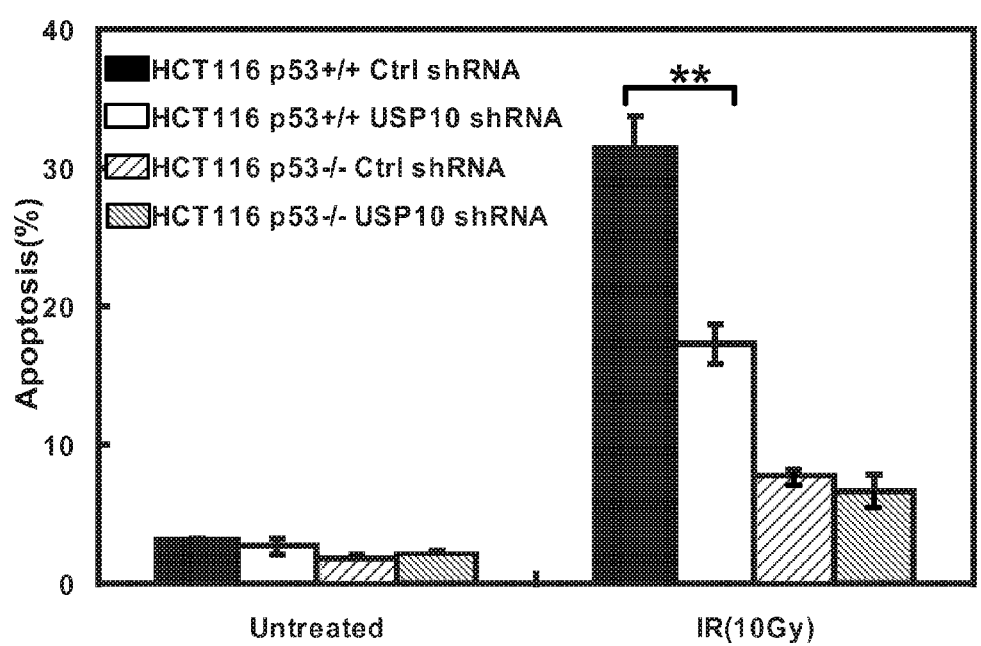
Figure 5E:
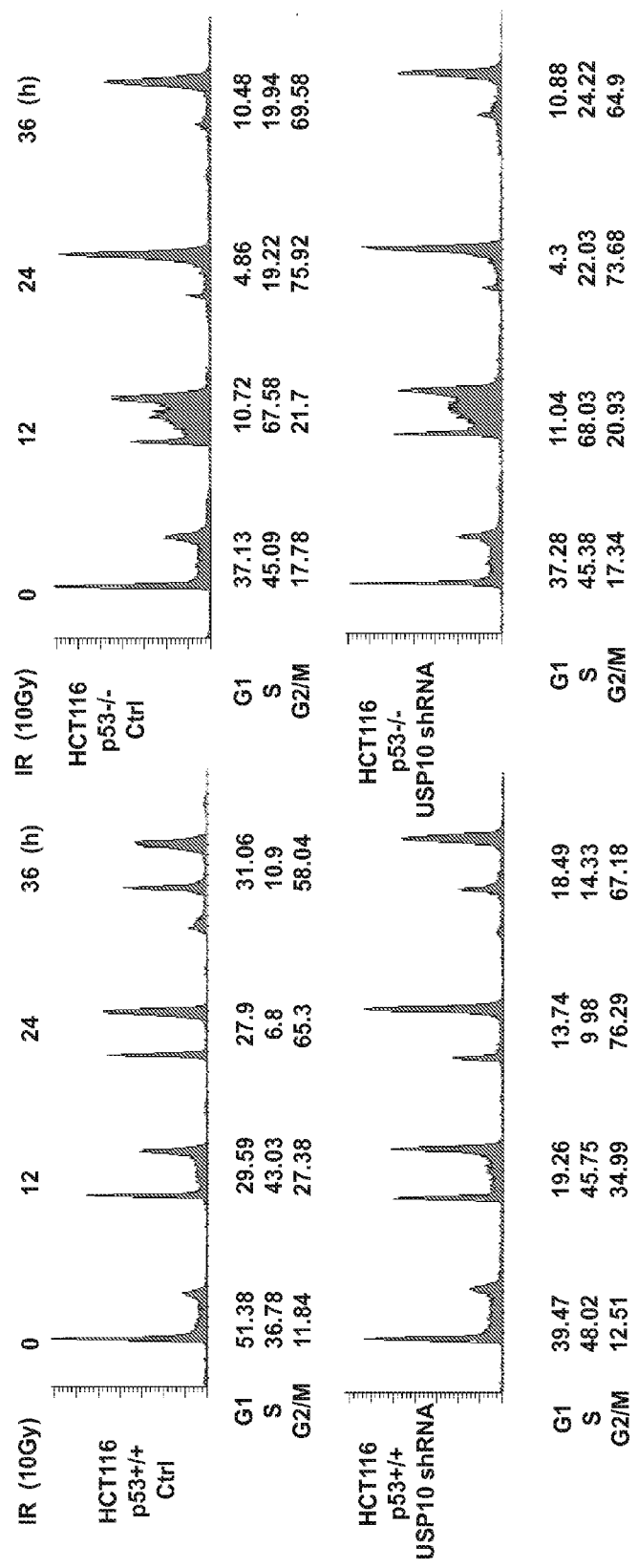

Since USP10 regulates p53 stabilization following DNA damage, whether USP10 is required for p53-dependent function during DNA damage response was examined. As shown in FIG. 5D, downregulation of USP10 inhibited IR-induced apoptosis in HCT116 p53$^{+/+}$ cells. The IR-induced apoptosis in HCT116 p53$^{-/-}$ cells was blunted, however, downregulation of USP10 did not have a further effect. Furthermore, knockdown of USP10 in HCT116 p53$^{+/+}$ cells resulted in defective DNA damage-induced G1 arrest (FIG. 5E). These results are consistent with decreased Bax and p21 expression in cells with USP10 downregulation (FIG. 5A), and suggest that USP10 is required for p53 activation following DNA damage.

USP10 Phosphorylation by ATM is Required for its Stabilization and Translocation Following DNA Damage The following experiments were performed to determine the molecular mechanisms that regulate USP10 upregulation and translocation. Initial experiments indicated that unlike p21, the upregulation of USP10 occurred without any change in USP10 mRNA (FIG. 6A), suggesting it is not regulated at the transcriptional level, and might be regulated at the post-translational levels. To examine whether USP10 polypeptides become stabilized, cells were irradiated, and cells were treated with cycloheximide. As shown in FIG. 6B, USP10 became more stable in irradiated cells, suggesting USP10 accumulation after DNA damage is due to increased stability.

Phosphorylation is a major posttranslational modification of the DNA damage response pathway, and it has been shown to enhance protein stability and activity. For example, p53 is phosphorylated at Ser20 by the checkpoint kinase Chk2 after IR, which results in p53's dissociation from Mdm2 and its subsequent stabilization (Chehab et al., *Genes Dev.*, 14:278-288 (2000); Hirao et al., *Science*, 287:1824-1827 (2000); and Shieh et al., *Genes Dev.*, 14:289-300 (2000)). ATM can also directly phosphorylate p53 at Ser15, so regulating p53 transcriptional activity and localization (Canman et al., *Science*, 281:1677-1679 (1998); Siliciano et al., *Genes Dev.*, 11:3471-3481 (1997); and Zhang and Xiong, *Science*, 292:1910-1915 (2001)). Therefore, it was examined whether USP10 is phosphorylated following DNA damage, which might be responsible for its stabilization and localization. As shown in FIG. 6C, following IR, UV, or etoposide treatment, USP10 became phosphorylated at SQ/TQ motifs (USP10 polypeptide levels were equalized to specifically examine USP10 phosphorylation in experiments of FIG. 6C-E). The SQ/TQ motifs are consensus phosphorylation sites for PI3-kinase like kinases (PIKKS), such as ATM, ATR, and DNA-PK (Abraham, *Genes Dev.*, 15:2177-2196 (2001)), the major upstream kinases of the DNA damage response pathway. Experiments were performed to determine whether PIKKs are required for USP10 phosphorylation using the pan-PIKK inhibitor caffeine (Sarkaria et al., *Cancer Res.*, 59:4375-4382 (1999)). As shown in FIG. 6D, caffeine inhibited USP10 phosphorylation after DNA damage. In addition, a specific ATM inhibitor KU55933 (Hickson et al., *Cancer Res.*, 64:9152-9159 (2004)) also inhibited USP10 phosphorylation after IR. These results suggest that PIKKS, likely ATM, regulate USP10 phosphorylation after DNA damage. The role of ATM in USP10 phosphorylation was further confirmed using ATM$^{+/+}$ or ATM$^{-/-}$ cells. As shown in FIG. 6E, USP10 failed to be phosphorylated at the SQ/TQ motifs in ATM$^{-/-}$ cells. Furthermore, USP10 levels did not increase following DNA damage in ATM$^{-/-}$ cells (FIG. 6F). These results indicate that USP10 is phosphorylated by ATM following DNA damage, which might contribute to its stabilization.

Experiments were performed to determine the ATM phosphorylation sites of USP10. ATM specifically phosphorylates SQ/TQ motifs, of which there are two candidate sites in USP10: T42Q and S337Q. Mutation at either T42 or S337 partially affects USP10 stabilization, and mutating both T42 and S337 (USP10 2SA) abolished USP10 stabilization following DNA damage (FIG. 6G). Mutation of both T42 and S337 (USP10 2SA) also abolished USP10 phosphorylation by ATM (FIG. 6H). In addition, the USP10 2SA mutant failed to translocate into the nucleus following DNA damage (FIG. 6I and FIG. 8B). These results indicate that ATM-mediated phosphorylation of USP10 is required for USP10 translocation and stabilization.

Figure 6J:
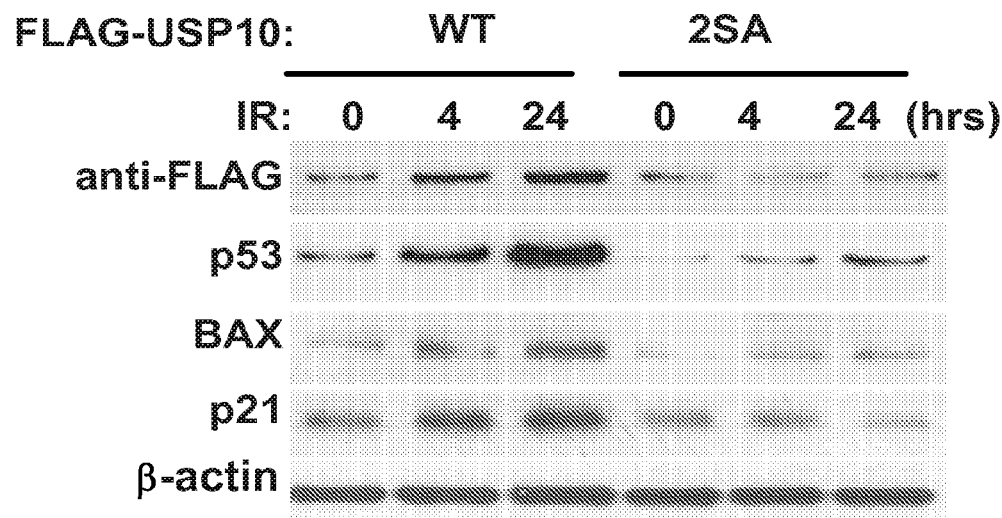
FIG. 6. USP10 phosphorylation by ATM regulates USP10 stabilization, translocation, and p53 activation following DNA damage. (A) HCT116 cells were irradiated (10 Gy) and harvested at the indicated times. Cell lysates and mRNA were then extracted and analyzed by Western blot or RT-PCR, respectively. (B) HCT116 cells were left untreated or irradiated. Cells were then treated with cycloheximide (0.1 mg/mL) and harvested at the indicated times. Cell lysates were then blotted with the indicated antibodies. (C) HCT116 cells were transfected with FLAG-tagged USP10. Forty-eight hours later, the cells were left untreated or treated with 10 Gy radiation, 40 J/m$^2$ UV, or 20 mM etoposide. After an additional 1 hour, the cells were harvested. Cell lysates were subjected to immunoprecipitation with anti-FLAG antibody and immunoblotted with phospho-SQ/TQ (pSQ/TQ) antibody. (D) HCT116 cells were transfected with FLAG-tagged USP10 and pretreated with DMSO, 25 mM Ku55933, or 3 mM caffeine. After 2 hours of incubation, cells were left untreated or treated with 10 Gy radiation. The phosphorylation of USP10 was examined as in (C). (E) ATM$^{+/+}$ or ATM$^{-/-}$ cells were irradiated (10 Gy) or left untreated. After one hour, the cells were harvested, and cell lysates were subjected to immunoprecipitation with anti-USP10 antibody and blotted with pSQ/TQ antibody. (F). ATM$^{+/+}$ or ATM$^{-/-}$ cells were left untreated or irradiated (10 Gy) and were harvested at the indicated time. Cell lysates were then blotted with the indicated antibodies. (G) HCT116 cells stably expressing USP10 shRNA were reconstituted with shRNA resistant FLAG-tagged USP10 WT (wild type), T42A, S337A or 2SA (T42A and S337A double mutation). Cells were left untreated or irradiated (10 Gy) and harvested at the indicated time. Cell lysates were then blotted with the indicated antibodies. (H) HCT116 cells stably expressing USP10 shRNA were reconstituted with shRNA resistant FLAG-tagged USP10 WT or 2SA. Cells were left untreated or treated with 10 Gy radiation. USP10 phosphorylation was examined by pSQ/TQ antibody. (I) Cells the same as (H) were irradiated (10 Gy) or left untreated. After four hours, cells were harvested and fractionated as described herein. (J) Cells the same as (H) were left untreated or irradiated (10 Gy). Cells were harvested at the indicated time, and cell lysates were blotted with the indicated antibodies. (K) Cells the same as (H) were left untreated or irradiated. Apoptotic cells were determined 48 hours later.
Figure 6K:
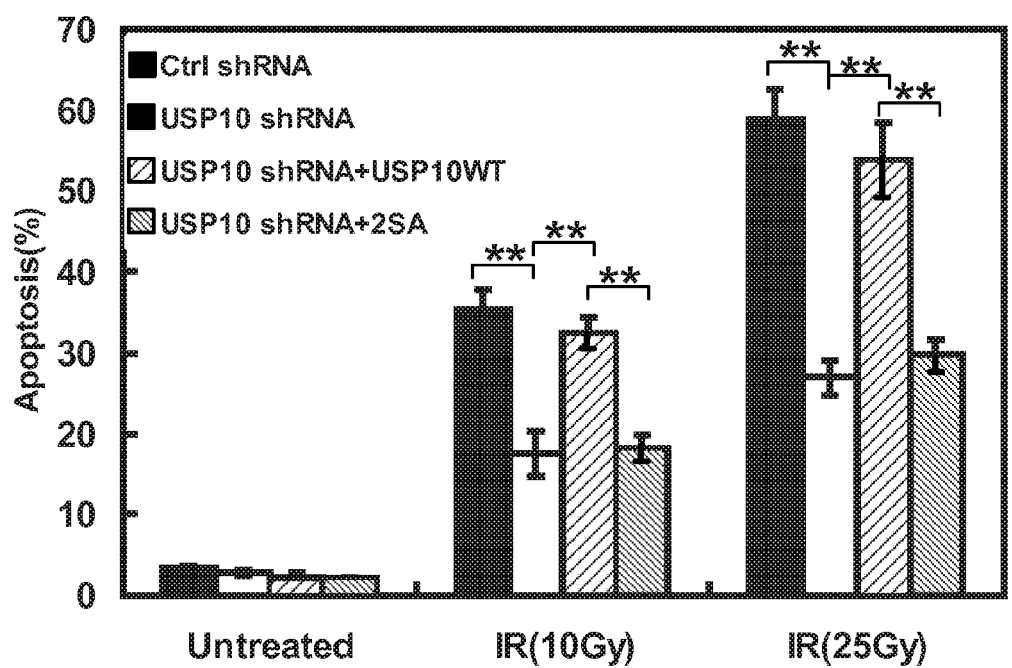

The functional significance of USP10 phosphorylation by ATM was examined. HCT116 cells stably expressing USP10 shRNA were reconstituted with shRNA-resistant wild-type USP10 or USP10 2SA. As shown in FIG. 6J, cells expressing the USP10 2SA mutant exhibited defective p53 stabilization and poor induction of Bax and p21 following DNA damage. In addition, reconstitution with wild-type USP10, but not the USP10 2SA mutant, restored DNA damage-induced apoptosis (FIG. 6K). These results establish the role of USP10 phosphorylation in p53 activation following DNA damage.

USP10 is Downregulated in Renal Cell Carcinoma

Figure 7A:
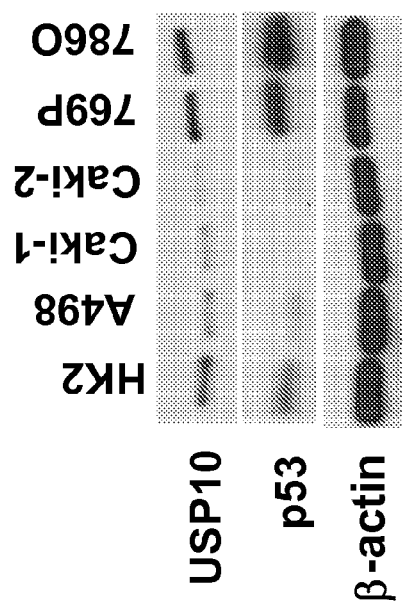
FIG. 7. USP10 is downregulated in renal cell carcinoma. (A) Expression of USP10 and p53 in human renal tubular epithelial cell line (HK-2) and renal cell carcinoma (RCC) cell lines. (B) 11 pairs of fresh frozen RCC tissues and corresponding normal tissues were lysed, and cell lysates were blotted with the indicated antibodies. (N: normal tissue; T: tumor tissue) (C) Immunohistochemical staining of USP10 in normal renal tissues and renal cell carcinoma. Lower table: quantification of USP10-positive or USP10-negative renal cell carcinoma cases. (ccRCC: clear cell Renal Cell Carcinoma). (D-E) Soft agar colony-formation assay was performed using CAKI-1 and CAKI-2 cells stably expressing S/FLAG-USP10 (D) and 786-O cells stably expressing S/FLAG-USP10 or USP10 shRNA (E). Lower panels: quantification of colonies formed in soft agar. Error bar represents the mean±SEM of triplicate experiments. ** represents P<0.01 two tailed student's t test. Bars represent 400 μm. (F) A schematic of a model showing how USP10 regulates p53.
Figure 7B:
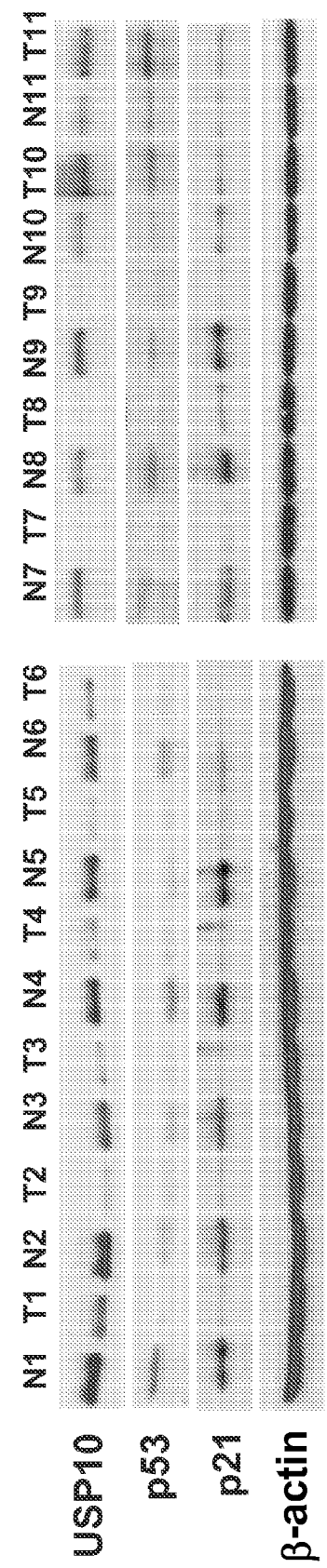

Since p53 is a tumor suppressor that regulates cell proliferation and USP10 potentiates p53 function by deubiquitinating p53, it is possible that USP10 also acts as a tumor suppressor. The results shown in FIGS. 4D and E demonstrate USP10's ability to inhibit cancer cell proliferation and lend support to the hypothesis that USP10 functions as a tumor suppressor in vivo. To further test this hypothesis, the expression of USP10 in a panel of renal cell carcinoma (RCC) cell lines was examined. RCC was selected to study USP10 expression because a very low percentage of RCC cases has been found to have p53 mutations ((Soussi et al., *Hum. Mutat.*, 15:105-113 (2000)). See, also, the p53 database at the International Agency for Research on Cancer. Given the function of p53 in tumor suppression, it is possible that the p53 pathway is compromised in RCC through other mechanisms, such as the downregulation of USP10. Indeed, USP10 expression was found to be significantly decreased in several RCC cell lines including A498, Caki-1, and Caki-2 cells, all of which contain wild-type p53 (FIG. 7A). p53 expression was also lower in these cells than that of normal renal cells. However, in RCC cell lines with mutant p53, USP10 levels were increased. USP10 levels were also decreased in a majority of fresh frozen RCC tissues compared to corresponding normal tissues (FIG. 7B). The RCC samples with USP10 downregulation all contained wild-type p53 gene (T1-T9), although p53 levels were decreased. These results suggest that downregulation of USP10 might be an alternative way to suppress p53 activity in RCC. Interestingly, similar as RCC cell lines, USP10 was overexpressed in some RCC tissues, and these tissues contained mutant p53 (T10, T11). These results suggest that increased USP10 levels in a mutant p53 background might be beneficial to tumor growth.

Figure 7C:
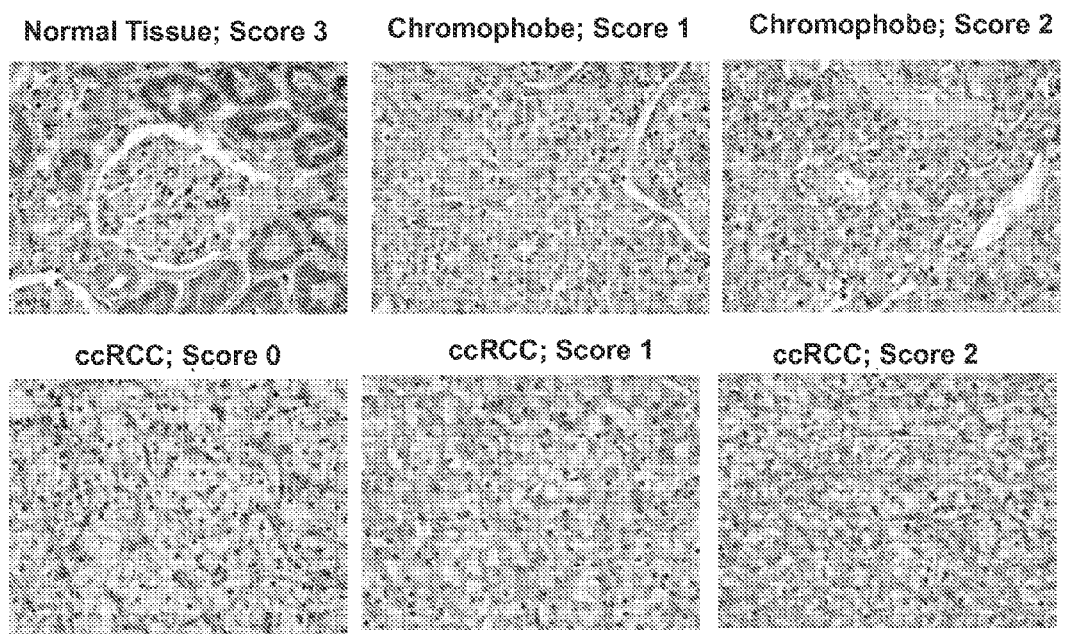

The expression of USP10 was further examined using RCC tissue microarray. The staining of USP10 was scored from 0-3, with a score of 0-1 being negative and a score of 2-3 being positive. Representative staining and scores were shown in FIG. 7C. Strikingly, close to 90% of clear cell carcinoma exhibited negative staining of USP10. About 50% of chromophobe and 20% of papillary RCC exhibited negative USP10 staining. These results suggest that USP10 is downregulated in RCC cases, especially clear cell carcinoma.

Figure 7D:
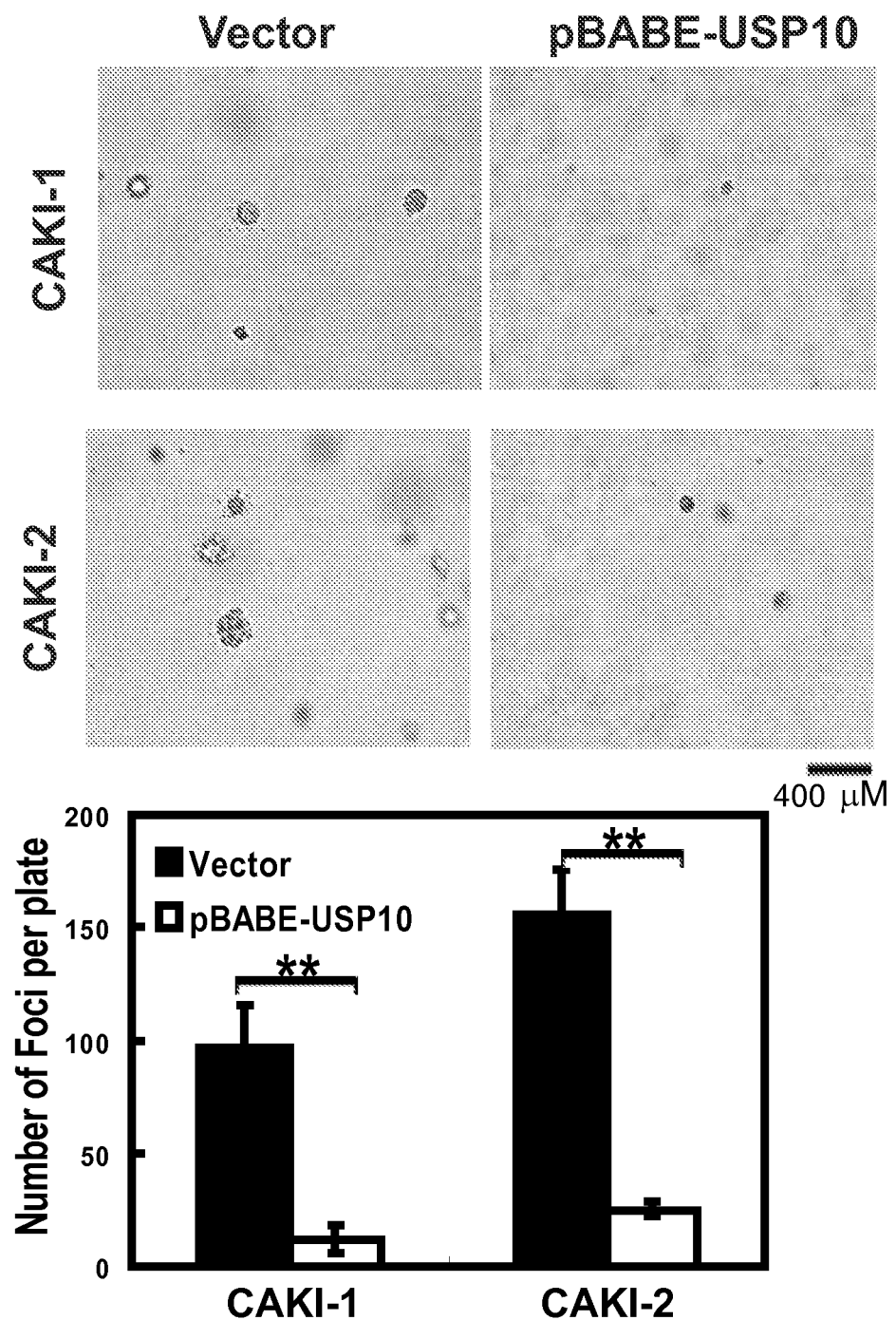
Figure 8C:
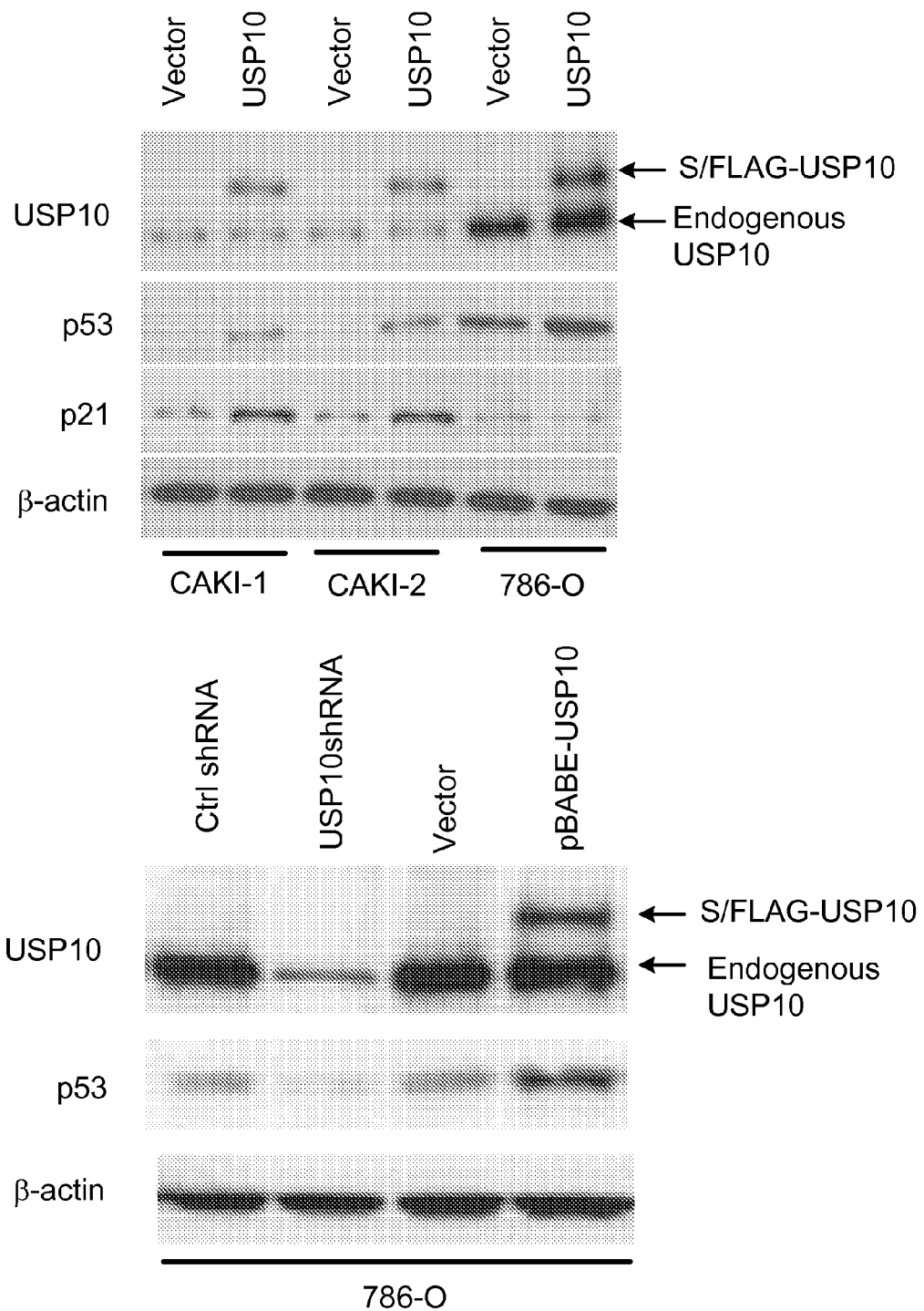

To confirm the role of USP10 in tumor suppression, USP10 was reconstituted in RCC cells with USP10 downregulation, and tumor cell growth was examined using soft agar assay. Reconstitution of USP10 in CAKI-1 and CAKI-2 clear cell carcinoma cell lines, which contain wild-type p53, restored p53 expression and increased p21 expression (FIG. 8C). Furthermore, cell proliferation was inhibited with USP10 reconstitution (FIG. 7D). These results are consistent with the hypothesis that USP10 functions as a tumor suppressor by stabilizing p53.

Figure 7E:
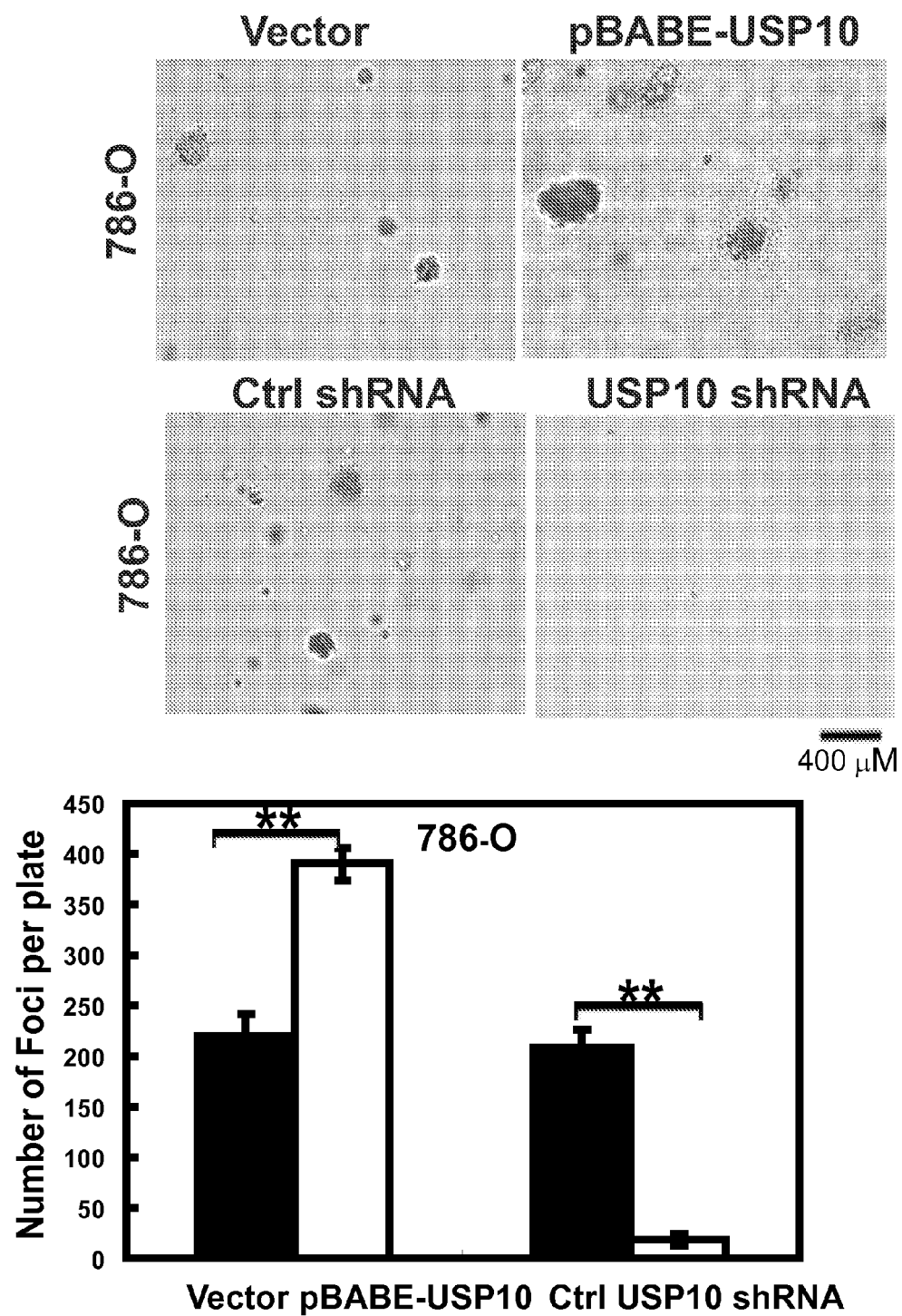

USP10 is overexpressed in RCC cell lines and tissues with mutant p53, correlating with increased p53 levels. This is consistent with a phenomena that mutant p53 is often overexpressed in many cancers. Since mutant p53 is often dominant and displays gain of function, increased p53 levels could be advantageous to cancer. In contrast to cells with wild-type p53, increased expression of USP10 in mutant p53 background could be beneficial to cancer cell proliferation. Indeed, increased expression of USP10 in 786-O cells, which contain mutant p53, resulted in increased cell proliferation, while downregulation of USP10 inhibited cell proliferation (FIG. 7E and FIG. 8C). These results suggest that USP10 regulates p53 and cancer cell proliferation in a context-dependent manner.

Figure 16A:
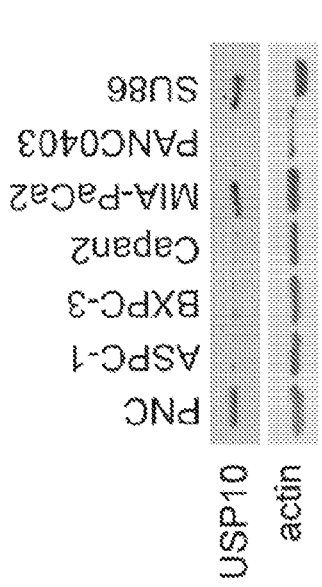
FIG. 16 contains photographs of Western Blots for β-actin and USP10 polypeptides in pancreatic cancer cell lines (A), breast cancer cell lines (B), and pancreatic tissues (C). The N represents normal tissue, while the T represents tumor tissue.
Figure 16B:
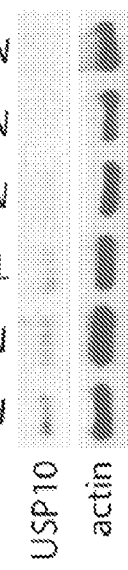
Figure 16C:
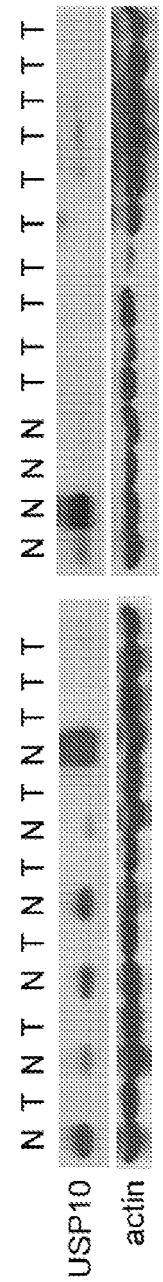

The expression of USP10 in breast and pancreatic cancer cell lines was examined. As shown in FIG. 16A-B, USP10 was downregulated in a subset of breast and pancreatic cancer cell lines. In addition, USP10 expression was lost in many pancreatic cancer tissues (FIG. 16C). These results further confirm that USP10 might function as a tumor suppressor in multiple cancers.

Figure 7F:
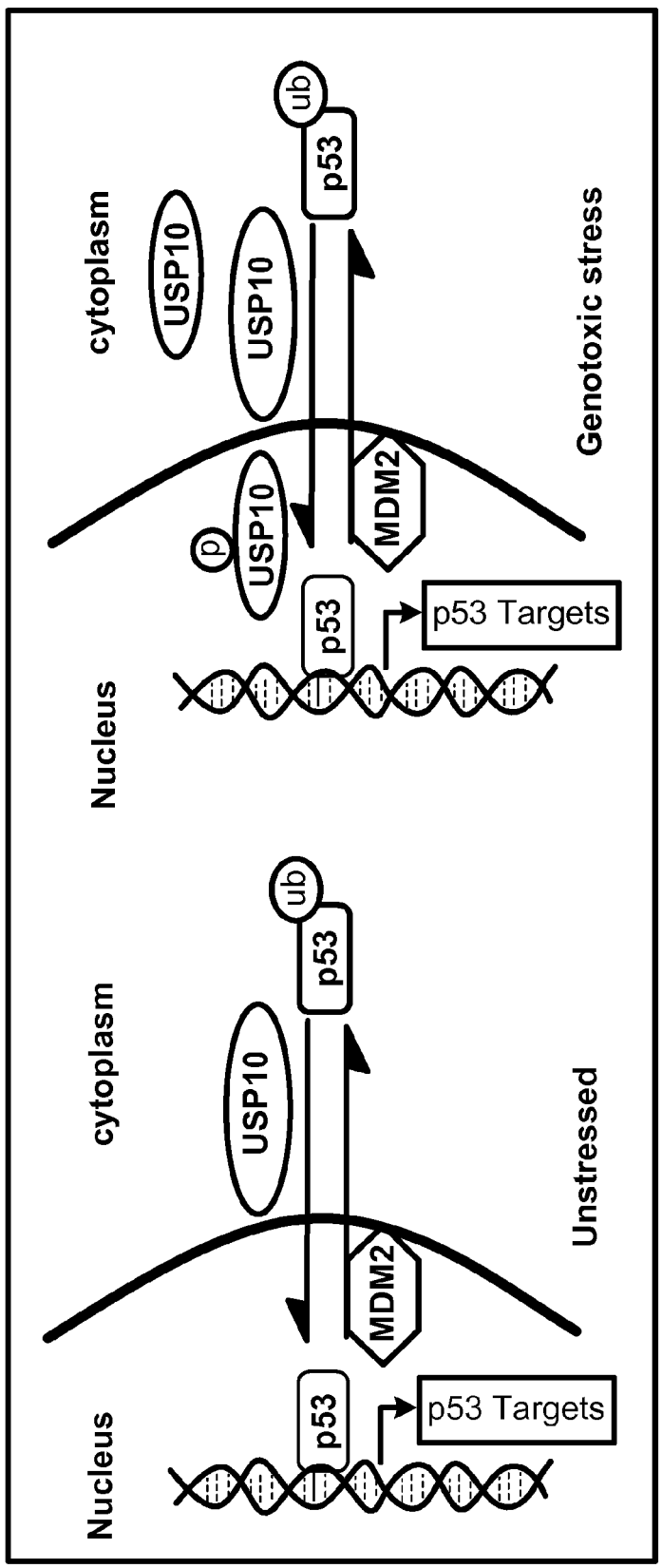

In summary, the results provided herein indicate that in unstressed cells, USP10 localizes in the cytoplasm and regulates p53 homeostasis. Following DNA damage, a fraction of USP10 translocates to the nucleus and contributes to p53 activation (FIG. 7F). USP10, through its regulation of p53, plays a role in tumor suppression.

Example 2

Inhibiting USP10 Polypeptide Activity

Figure 17A:
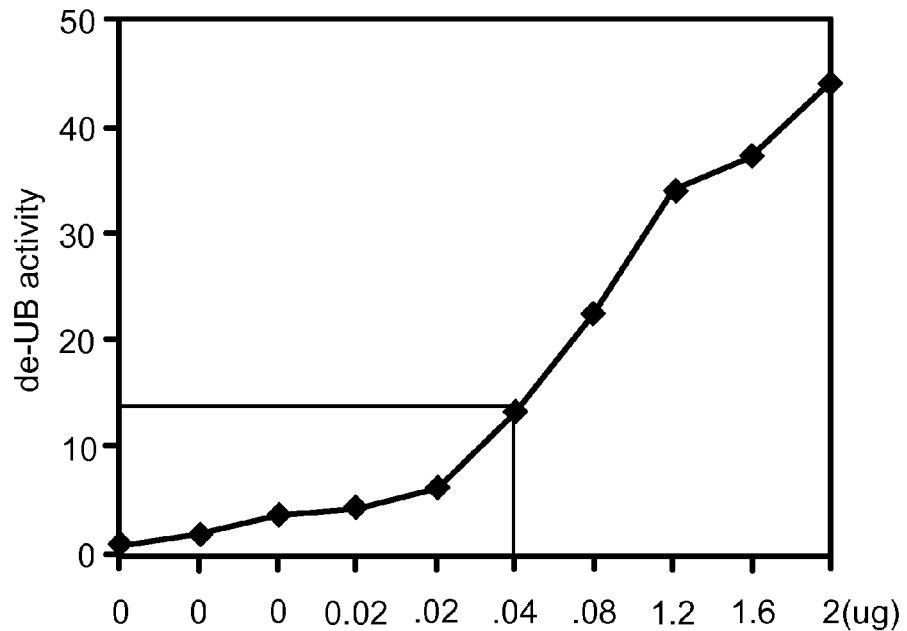
FIG. 17A is a concentration curve graph plotting the level of deubiquitination of Ub-AMC observed following incubation with the indicated amounts of USP10 polypeptide (μg).

Ubiquitin-AMC (Ub-AMC; BIOMOL), which is a fluorogenic substrate for a wide range of deubiquitinylating enzymes (Dang et al., Biochemistry, 37:1868 (1998)), was used as a substrate of USP10 polypeptides to demonstrate that the deubiquitination of Ub-AMC by USP10 polypeptides is dose dependent. Briefly, the amount of Ub-AMC deubiquitination in vitro increased as the concentration of USP10 polypeptides increased (FIG. 17A).

N-ethylmaleimide (1 mM), Z-phe-ala fluoromethyl ketone (80 µM), antipain dihydrochloride (10 µg/mL), E-64 (10 µM), chymostatia (100 µM), phenylmethanesulfonyl fluoride (40 µM), E-64d (0.5 µM), and cystatin (36 µg/mL) were tested for the ability to inhibit USP10 polypeptide activity using USP10 polypeptide (4 µg/mL) and Ub-AMC (300 nmol/L). Briefly, both enzyme (USP10 polypeptide) and substrate (Ub-AMC) were freshly prepared in USP10 reaction buffer (50 mmol/L Tris-HCl (pH 7.6), 0.5 mmol/L EDTA, 5 mmol/L DTT, 0.01% Triton X-100, and 0.05 mg/mL serum albumin) for each run. Each well (except substrate control wells) in a typical assay contained 4 µg/mL of USP10, the compound, or 2% DMSO. The wells were incubated for 30 minutes to attain equilibrium, and the enzymatic reaction was then initiated by adding the substrate (300 nmol/L of Ub-AMC). The reaction mixture was incubated at room temperature for 2 hours, and the reaction was stopped by adding 250 mmol/L acetic acid.

Figure 17B:
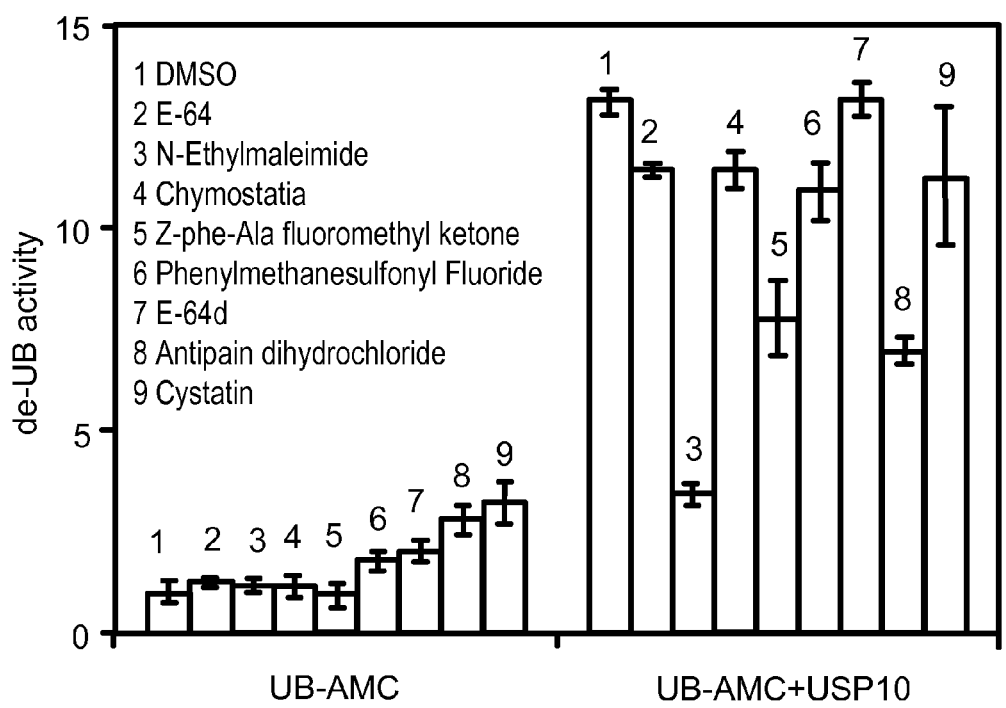
FIG. 17B is a graph plotting the level of deubiquitination of Ub-AMC in the presence (right) or absence (left) of 4 μg/mL of USP10 polypeptides and the indicated compound.

The deubiquitinating activity of USP10 polypeptides was significantly inhibited ($p<0.01$) by N-ethylmaleimide (1 mM), Z-phe-ala fluoromethyl ketone (80 µM), and antipain dihydrochloride (10 µg/mL) as compared to incubation with DMSO (FIG. 17B).

Example 3

G3BP1 Polypeptides Inhibit USP10 Polypeptide Activity

Co-immunoprecipitation assays were performed as follows. Cells were lysed with NETN buffer (20 mM Tris-HCl, pH 8.0, 100 mM NaCl, 1 mM EDTA, 0.5% Nonidet P-40) containing 50 mM β-glycerophosphate, 10 mM NaF, and 1 mg/mL each of pepstatin A and aprotinin. Whole cell lysates obtained by centrifugation were incubated with 2 µg of antibody and protein A or protein G Sepharose beads (Amersham Biosciences) for 2 hours at 4° C. The immunocomplexes were then washed with NETN buffer three times and separated by SDS-PAGE. Immunoblotting was performed following standard procedures.

Cell growth assays were performed as follows. Cell growth was analyzed using MTS reagent (Promega) according to the manufacturer's directions. HCT116 cells stably infected with lentivirus encoding control shRNA or shRNA designed to reduce USP10 polypeptide expression (1,000 cells/well) were transfected with indicated constructs. After 24 hours, the cells were plated on 96-well plates and grown on 10% serum containing media. Cell proliferation was estimated after 1, 2, 3, 4 and 5 days.

Figure 18:
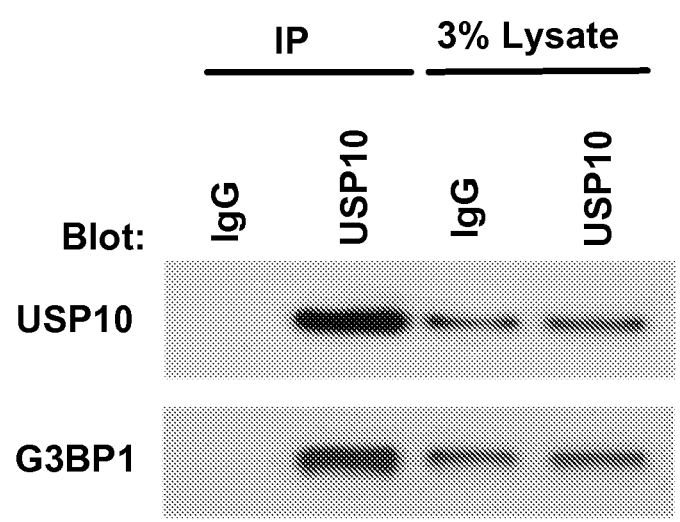
FIG. 18 is a photograph of an immunoprecipitation of HCT116 cell lysates with an anti-USP10 polypeptide antibody (or control antibody, IgG) and immunoblotted with anti-G3BP1 polypeptide antibodies or anti-USP10 polypeptide antibodies.

HCT116 cells were harvested and lysed. The resulting cell lysates were subjected to immunoprecipitation with anti-USP10 polypeptide antibody and immunoblotted with anti-G3BP1 polypeptide antibodies or anti-USP10 polypeptide antibodies (FIG. 18). These results demonstrate that G3BP1 polypeptides interact with USP10 polypeptide in vivo. In addition, experiments using full length and fragments of full length USP10 polypeptides indicated that both G3BP1 polypeptides and p53 polypeptides interact with the N-terminal region (e.g., 1-100 amino acids) of USP10 polypeptides (FIG. 19A).

In one experiment, HCT116 cells were treated with MG132 for 4 hours and were depleted of G3BP1 polypeptide expression using shRNA having the following sequence: 5'-ATGTTTCATTCATTGGAAT-3' (SEQ ID NO:12). MG132 is a specific, potent, reversible, and cell-permeable proteasome inhibitor. In another experiment, HCT116 cells transfected with a vector designed to express a FLAG-G3BP1 polypeptide were treated with MG132 for 4 hours. In both cases, the cells were lysed, and cell lysates were subjected to immunoprecipitation with anti-p53 polypeptide antibodies and immunoblotted with anti-USP10 polypeptide antibodies, anti-p53 polypeptide antibodies, anti-G3BP1 antibodies, and/or anti-FLAG antibodies.

G3BP1 polypeptides competed with p53 polypeptides for USP10 polypeptide binding (FIGS. 19B and 19C). Depletion of G3BP1 polypeptide expression by shRNA significantly increased the binding between USP10 polypeptides and p53 polypeptides (FIG. 19B). Over-expression of G3BP1 polypeptides reduced the binding between USP10 polypeptides and p53 polypeptides (FIG. 19C). These results indicate that G3BP1 polypeptides compete with p53 polypeptides for USP10 polypeptide binding.

Figure 20:
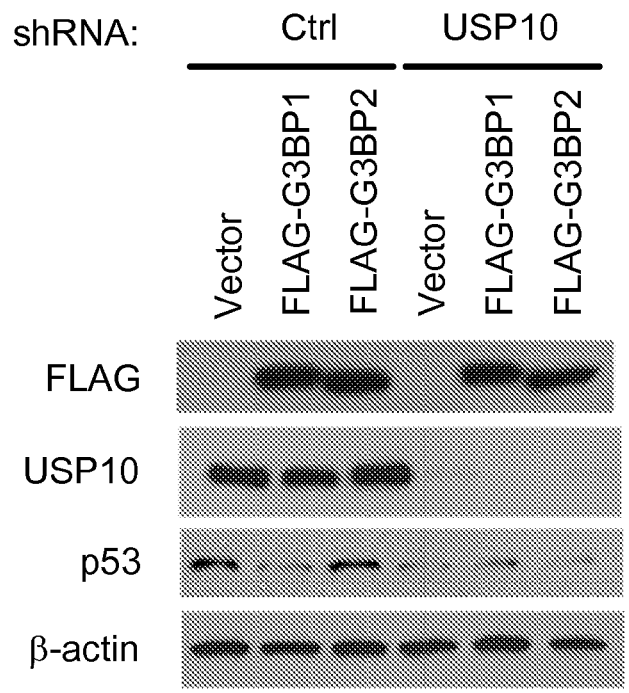
FIG. 20 is a photograph of HCT116 cell lysates immunoblotted with anti-FLAG antibodies, anti-USP10 polypeptide antibodies, anti-p53 polypeptide antibodies, or anti-β-actin antibodies. The HCT116 cell lysates were obtained from cells stably transfected with either a control construct (Ctrl) or an shRNA construct designed to reduce USP10 polypeptide expression (USP10) that were transfected with an empty vector (Vector), a vector designed to over-express G3BP1 polypeptides (FLAG-G3BP1), or a vector designed to overexpress G3BP2 polypeptides (FLAG-G3BP2).

In another experiment, HCT116 cells stably transfected with either a control construct or an shRNA construct designed to reduce USP10 polypeptide expression were transfected with an empty vector, a vector designed to over-express FLAG-tagged G3BP1 polypeptides, or a vector designed to over-express FLAG-tagged G3BP2 polypeptides. The shRNA designed to reduce USP10 polypeptide expression had the following sequence: 5'-GCCTCTCTTTAGTG-GCTCTTT-3' (SEQ ID NO:13). 48 hours later, the cells were lysed, and cell lysates were blotted with anti-FLAG antibodies, anti-USP10 polypeptide antibodies, anti-p53 polypeptide antibodies, or anti-β-actin antibodies. Overexpression of G3BP1 polypeptides, but not G3BP2 polypeptides, decreased the level of p53 polypeptides (FIG. 20). Overexpression of G3BP1 polypeptides did not change the level of p53 polypeptides in cells depleted of USP10 polypeptides (FIG. 20). These results indicate that G3BP1 polypeptides regulate p53 polypeptide through USP10 polypeptides.

Figure 21:
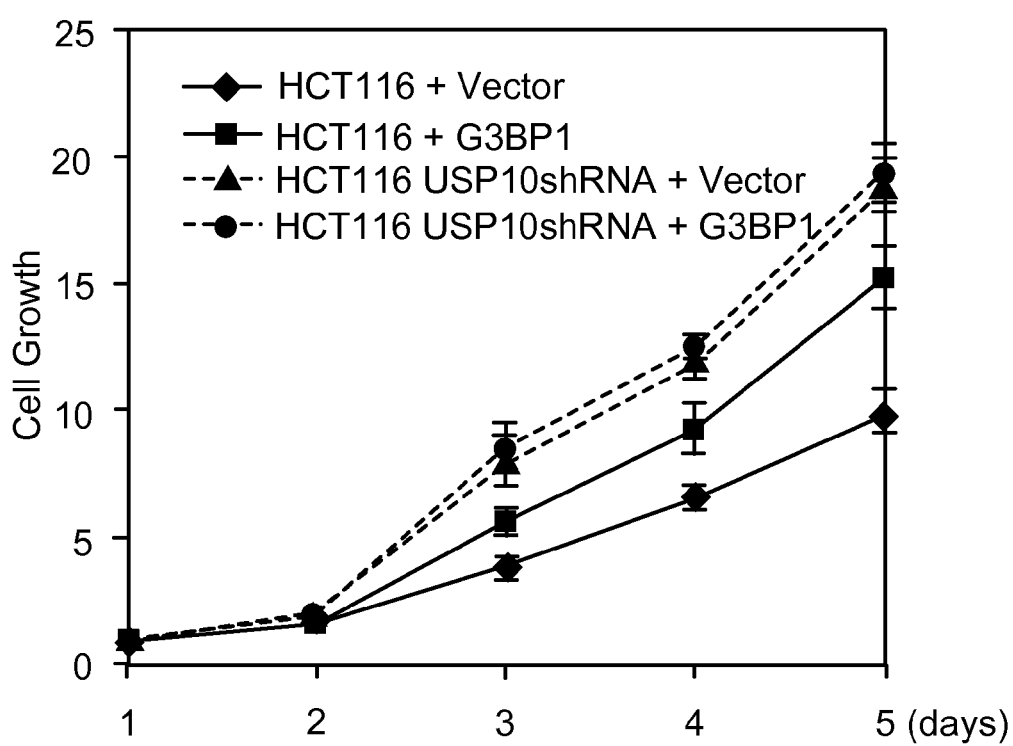
FIG. 21 is a graph plotting cell growth (fold of growth, set cell number at day 1 as 1) versus time (days) for HCT116 cells stably expressing either control or an shRNA construct designed to reduce expression of USP10 polypeptides (USP10shRNA) and transfected with a control vector (Vector) or a FLAG-G3BP1 construct (G3BP1).

In another experiment, HCT116 cells stably expressing either control construct or an shRNA construct designed to reduce expression of USP10 polypeptides (USP10shRNA) were transfected with a control vector or a FLAG-G3BP1 vector. 24 hours later, the cells were plated, and cell growth was measured by MTS assay at days 1, 2, 3, 4, and 5. Over-expression of G3BP1 polypeptides significantly enhanced cell growth in HCT116 cells, but not in HCT116 cells with depleted USP10 polypeptides (FIG. 21). These results demonstrate that G3BP1 polypeptides regulate cancer cell growth through USP10 polypeptides.

Figure 22:
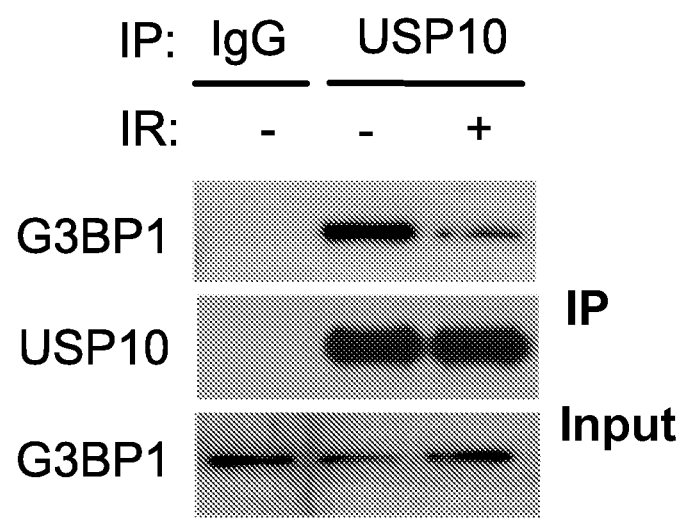
FIG. 22 is a photograph of an immunoprecipitation of HCT116 cell lysates with an anti-USP10 polypeptide antibody (or control antibody, IgG) and immunoblotted with anti-G3BP1 polypeptide antibodies and anti-USP10 polypeptide antibodies. The HCT116 cell lysates were obtained from untreated cells or cells treated with 10 Gy irradiation.

In another experiment, HCT116 cells were left untreated or were treated with 10 Gy irradiation. Two hours later, the cells were lysed. The resulting cell lysates were subjected to immunoprecipitation with an anti-USP10 polypeptide antibody and immunoblotted with anti-G3BP1 polypeptide antibodies and anti-USP10 polypeptide antibodies. X-Ray Irradiation dramatically decreased the interaction between USP10 polypeptides and G3BP1 polypeptides (FIG. 22). These results demonstrate that DNA damage relieves USP10 polypeptides from G3BP1 polypeptide inhibition.

Other Embodiments

It is to be understood that while the invention has been described in conjunction with the detailed description

What is claimed is:

1. A method for treating cancer in a mammal, wherein said method comprises:
   (a) identifying a mammal as having cancer cells that express a mutant p53 polypeptide, and
   (b) administering a composition that decreases USP10 polypeptide expression or activity within said cancer cells.

2. The method of claim 1, wherein said mammal is a human.

3. The method of claim 1, wherein said composition comprises N-ethylmaleimide, Z-phe-ala fluoromethyl ketone, or chymostatin.

4. The method of claim 1, wherein said composition comprises trans-Epoxysuccinyl-L-leucylamido (4-guanidino)butane (E-64), (2S, 3S)-trans-Epoxysuccinyl-L-leuclamido-3-methylbutane ethyl ester (E-64d), or antipain dihydrochloride.

5. The method of claim 1, wherein said composition comprises cystatin or a cyano-indenopyrazine derivative.

6. The method of claim 1, wherein said composition comprises nucleic acid having the ability to induce RNA interference against expression of said USP10 polypeptide.

7. The method of claim 1, wherein said USP10 polypeptide is a human USP10 polypeptide.

* * * * *

UNITED STATES PATENT AND TRADEMARK OFFICE
CERTIFICATE OF CORRECTION

| | | |
|---|---|---|
| PATENT NO. | : 8,853,180 B2 | Page 1 of 1 |
| APPLICATION NO. | : 13/394786 | |
| DATED | : October 7, 2014 | |
| INVENTOR(S) | : Lou et al. | |

It is certified that error appears in the above-identified patent and that said Letters Patent is hereby corrected as shown below:

On Title Page 2, Column 2, Item [56] Other Publications, Line 3-4 delete "p53 and MDM2" and insert -- p53-MDM2 --, therefor.

In the Claims

Column 40, line 14 Claim 4, delete "leuclamido" and insert -- leucylamido --, therefor.

Signed and Sealed this
Tenth Day of February, 2015

Michelle K. Lee
*Deputy Director of the United States Patent and Trademark Office*